US010874438B2

(12) United States Patent
Biester et al.

(10) Patent No.: US 10,874,438 B2
(45) Date of Patent: Dec. 29, 2020

(54) BONE ANCHOR ASSEMBLIES AND RELATED INSTRUMENTATION

(71) Applicant: Medos International Sarl, Le Locle (CH)

(72) Inventors: Eric Biester, Barrington, RI (US); Michael Sorrenti, Middleboro, MA (US); Ellen Wasserbauer, Mendon, MA (US)

(73) Assignee: Medos International Sarl, Le Locle (CH)

( * ) Notice: Subject to any disclaimer, the term of this patent is extended or adjusted under 35 U.S.C. 154(b) by 83 days.

(21) Appl. No.: 16/183,720

(22) Filed: Nov. 7, 2018

(65) Prior Publication Data

US 2019/0150989 A1 May 23, 2019

Related U.S. Application Data

(63) Continuation-in-part of application No. 15/623,444, filed on Jun. 15, 2017, now Pat. No. 10,568,667, (Continued)

(51) Int. Cl.
*A61B 17/70* (2006.01)
*A61B 17/86* (2006.01)
*A61B 90/00* (2016.01)

(52) U.S. Cl.
CPC ...... *A61B 17/7037* (2013.01); *A61B 17/7001* (2013.01); *A61B 17/7007* (2013.01);
(Continued)

(58) Field of Classification Search
CPC ............ A61B 17/7032; A61B 17/7034; A61B 17/7035; A61B 17/7037
See application file for complete search history.

(56) References Cited

U.S. PATENT DOCUMENTS 5,879,350 A * 3/1999 Sherman ............ A61B 17/7037
606/266
6,010,503 A 1/2000 Richelsoph et al.
(Continued)

FOREIGN PATENT DOCUMENTS

EP 2170192 B1 2/2011
EP 2335625 A1 6/2011
(Continued)

OTHER PUBLICATIONS

[No Author Listed] Globus Medical, Creo Amp® Modular Stabilization System, 2015, 60 pages.
(Continued)

*Primary Examiner* — Julianna N Harvey
(74) *Attorney, Agent, or Firm* — Nutter McClennen & Fish LLP

(57) ABSTRACT

Bone anchor assemblies and related instrumentation are disclosed herein. In some embodiments, a modular bone anchor assembly allows for a bone anchor to be driven into bone and a head or receiver member to be attached thereto at some later point in time. The bone anchor can have a smaller footprint than the complete assembly, which can improve visualization and anatomical spatial awareness during insertion of the bone anchor and during other surgical steps performed prior to attaching the head or receiver member to the bone anchor. A variety of modular head types are disclosed, as are various instruments for driving a bone anchor, attaching a head to a bone anchor, removing a head from a bone anchor, and making a unilateral attachment to a head of a bone anchor assembly. Drive interfaces for driving a bone anchor are disclosed, as are features that allow a bone anchor to act as a fixation point for soft tissue retraction, disc space distraction, derotation, and the like.

22 Claims, 54 Drawing Sheets

Related U.S. Application Data which is a continuation-in-part of application No. 15/208,847, filed on Jul. 13, 2016, now Pat. No. 10,363,073, and a continuation-in-part of application No. 15/208,872, filed on Jul. 13, 2016, now Pat. No. 10,463,402.

(52) U.S. Cl.
CPC ........ *A61B 17/708* (2013.01); *A61B 17/7032* (2013.01); *A61B 17/7082* (2013.01); *A61B 17/7083* (2013.01); *A61B 17/863* (2013.01); *A61B 17/8615* (2013.01); *A61B 17/8625* (2013.01); *A61B 17/7041* (2013.01); *A61B 17/7076* (2013.01); *A61B 17/864* (2013.01); *A61B 2090/031* (2016.02); *A61B 2090/037* (2016.02)

(56) References Cited

U.S. PATENT DOCUMENTS

| | | |
|---|---|---|
| 6,017,177 A | 1/2000 | Lanham |
| 7,338,491 B2 | 3/2008 | Baker et al. |
| 7,479,156 B2 | 1/2009 | Lourdel et al. |
| 7,695,497 B2 | 4/2010 | Cordaro et al. |
| 7,896,902 B2 | 3/2011 | Jeon et al. |
| 8,012,186 B2 | 9/2011 | Pham et al. |
| 8,083,776 B2 | 12/2011 | Alvarez |
| 8,100,948 B2 | 1/2012 | Ensign et al. |
| 8,167,910 B2 | 5/2012 | Nilsson |
| 8,236,035 B1 | 8/2012 | Bedor |
| 8,262,701 B2 | 9/2012 | Rathbun et al. |
| 8,343,165 B2 | 1/2013 | Berrevoets |
| 8,394,109 B2 | 3/2013 | Hutton et al. |
| 8,439,922 B1 | 5/2013 | Arnold et al. |
| 8,454,661 B2 | 6/2013 | Rathbun et al. |
| 8,460,308 B2 | 6/2013 | Marino et al. |
| 8,491,641 B2 | 7/2013 | Nihalani |
| 8,506,601 B2 | 8/2013 | Gephart et al. |
| 8,506,610 B2 | 8/2013 | Biedermann et al. |
| 8,535,318 B2 | 9/2013 | Peterson et al. |
| 8,603,145 B2 | 12/2013 | Forton et al. |
| 8,663,298 B2 | 3/2014 | Keyer et al. |
| 8,690,924 B2 | 4/2014 | Chin et al. |
| 8,696,717 B2 | 4/2014 | Rock et al. |
| 8,696,718 B2 | 4/2014 | Barrus et al. |
| 8,764,805 B2 | 7/2014 | Biedermann et al. |
| 8,795,283 B2 | 8/2014 | Petit |
| 8,814,919 B2 | 8/2014 | Barrus et al. |
| 8,845,640 B2 | 9/2014 | McLean et al. |
| 8,852,239 B2 | 10/2014 | Jackson et al. |
| 8,876,869 B1 | 11/2014 | Schafer et al. |
| 8,888,827 B2 | 11/2014 | Harper et al. |
| 8,940,020 B2 | 1/2015 | Rathbun |
| 8,956,362 B2 | 2/2015 | Landry et al. |
| 8,979,898 B2 | 3/2015 | Ark et al. |
| 8,986,349 B1 | 3/2015 | German et al. |
| 9,017,390 B2 | 4/2015 | Biedermann et al. |
| 9,023,086 B2 | 5/2015 | Biedermann et al. |
| 9,044,272 B2 | 6/2015 | Shaffrey et al. |
| 9,044,274 B2 | 6/2015 | Gunn et al. |
| 9,066,759 B2 | 6/2015 | Biedermann et al. |
| 9,078,705 B2 | 7/2015 | Matthis et al. |
| 9,084,634 B1 | 7/2015 | Lab et al. |
| 9,119,674 B2 | 9/2015 | Matthis et al. |
| 9,131,971 B2 | 9/2015 | Biedermann et al. |
| 9,144,444 B2 | 9/2015 | Jackson |
| 9,155,567 B2 | 10/2015 | Auerbach et al. |
| 9,168,069 B2 | 10/2015 | Jackson et al. |
| 9,277,938 B2 | 3/2016 | Biedermann et al. |
| 9,333,016 B2 | 5/2016 | Biedermann et al. |
| 9,504,497 B2 | 11/2016 | Ark et al. |
| 10,363,073 B2 | 7/2019 | Raina et al. |
| 10,463,402 B2 | 11/2019 | Biester et al. |
| 10,568,667 B2 | 2/2020 | Biester et al. |
| 2004/0097933 A1* | 5/2004 | Lourdel ............ A61B 17/7037 606/266 |
| 2005/0228400 A1 | 10/2005 | Chao et al. |
| 2006/0149235 A1* | 7/2006 | Jackson ............ A61B 17/7032 606/328 |
| 2006/0161153 A1 | 7/2006 | Hawkes et al. |
| 2007/0123870 A1 | 5/2007 | Jeon et al. |
| 2007/0161998 A1 | 7/2007 | Whipple |
| 2007/0208344 A1* | 9/2007 | Young ............... A61B 17/7032 623/17.16 |
| 2008/0004625 A1* | 1/2008 | Runco ............... A61B 17/7037 606/273 |
| 2008/0045955 A1 | 2/2008 | Berrevoets et al. |
| 2008/0195155 A1 | 8/2008 | Hoffman et al. |
| 2008/0228233 A1 | 9/2008 | Hoffman et al. |
| 2008/0262556 A1 | 10/2008 | Jacofsky et al. |
| 2009/0240291 A1* | 9/2009 | Gorek ............... A61B 17/863 606/316 |
| 2009/0312804 A1 | 12/2009 | Gamache et al. |
| 2010/0094353 A1* | 4/2010 | Shim ................. A61B 17/7037 606/301 |
| 2010/0114174 A1 | 5/2010 | Jones et al. |
| 2010/0152787 A1 | 6/2010 | Walsh et al. |
| 2010/0160978 A1* | 6/2010 | Carbone ............ A61B 17/7037 606/305 |
| 2011/0046683 A1 | 2/2011 | Biedermann et al. |
| 2011/0106166 A1 | 5/2011 | Keyer et al. |
| 2011/0152949 A1 | 6/2011 | Biedermann et al. |
| 2011/0270325 A1 | 11/2011 | Keyer et al. |
| 2011/0288599 A1 | 11/2011 | Michielli et al. |
| 2012/0089150 A1 | 4/2012 | Smith |
| 2012/0130373 A1* | 5/2012 | Larroque-Lahitette ...... A61B 17/7022 606/74 |
| 2012/0143265 A1 | 6/2012 | Biedermann et al. |
| 2012/0197297 A1 | 8/2012 | Bootwala et al. |
| 2012/0203288 A1 | 8/2012 | Lange et al. |
| 2012/0277805 A1 | 11/2012 | Farris |
| 2013/0053901 A1 | 2/2013 | Cormier et al. |
| 2013/0060293 A1 | 3/2013 | Jackson et al. |
| 2013/0096623 A1 | 4/2013 | Biedermann et al. |
| 2013/0253586 A1 | 9/2013 | Rathbun et al. |
| 2013/0261679 A1 | 10/2013 | McBride et al. |
| 2013/0331892 A1 | 12/2013 | Peterson et al. |
| 2014/0012337 A1 | 1/2014 | Biedermann et al. |
| 2014/0058458 A1* | 2/2014 | Barrus ............... A61B 17/7032 606/308 |
| 2014/0121703 A1* | 5/2014 | Jackson ............ A61B 17/7032 606/246 |
| 2014/0142632 A1 | 5/2014 | Keyer et al. |
| 2014/0188172 A1 | 7/2014 | Nichols et al. |
| 2014/0188173 A1 | 7/2014 | Mishra et al. |
| 2014/0236238 A1* | 8/2014 | Ark .................... A61B 17/7032 606/278 |
| 2014/0257411 A1* | 9/2014 | Rezach ............. A61B 17/7037 606/305 |
| 2015/0012042 A1 | 1/2015 | Black |
| 2015/0112397 A1 | 4/2015 | Petit |
| 2015/0148848 A1 | 5/2015 | Doubler et al. |
| 2015/0182265 A1 | 7/2015 | Biedermann et al. |
| 2015/0196337 A1 | 7/2015 | Biedermann et al. |
| 2015/0257798 A1 | 9/2015 | Biedermann et al. |
| 2016/0331413 A1* | 11/2016 | Daniels ............. A61B 17/7035 |
| 2018/0014858 A1 | 1/2018 | Biester et al. |
| 2018/0014862 A1 | 1/2018 | Raina et al. |
| 2018/0014863 A1 | 1/2018 | Biester et al. |
| 2018/0193062 A1* | 7/2018 | May .................. A61B 17/7035 |
| 2018/0193063 A1* | 7/2018 | May .................. A61B 17/70 |

FOREIGN PATENT DOCUMENTS

| | | |
|---|---|---|
| EP | 2277466 B1 | 2/2012 |
| EP | 2719347 A1 | 4/2014 |
| WO | 2011/077511 A1 | 6/2011 |
| WO | 2011/109009 A1 | 9/2011 |
| WO | 2015/192057 A1 | 12/2015 |
| WO | 2016/065033 A1 | 4/2016 |

(56) References Cited

FOREIGN PATENT DOCUMENTS

OTHER PUBLICATIONS

[No Author Listed] Synthes® Spine, Universal Spinal System (USS) Polyaxial and Iliosacral Spine Fixation, A versatile system for posterior stabilization of spinal segements, 2009, Synthes, Inc., 61 pages.

International Search Report and Written Opinion for Application No. PCT/US2017/041588, dated Dec. 12, 2017 (17 pages).

International Search Report and Written Opinion for Application No. PCT/US2017/041592, dated Oct. 20, 2017 19 pages).

* cited by examiner

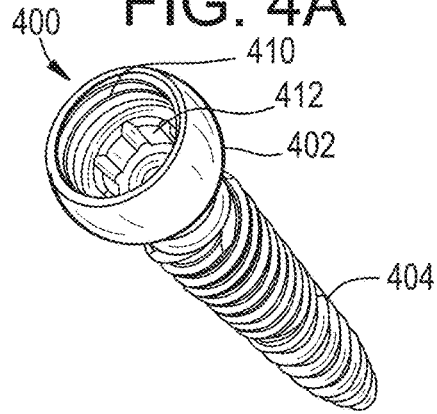
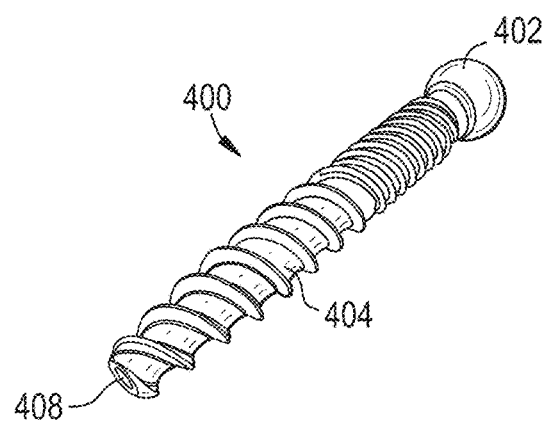
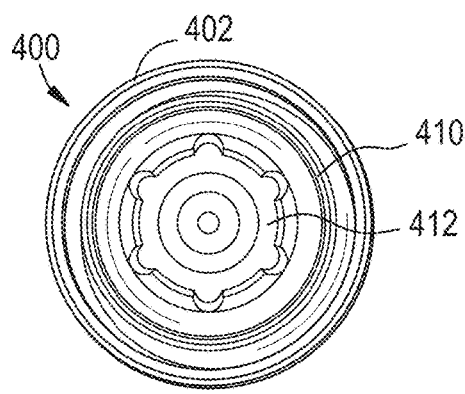
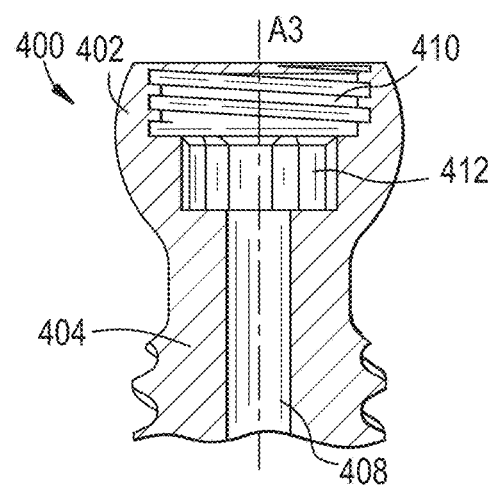
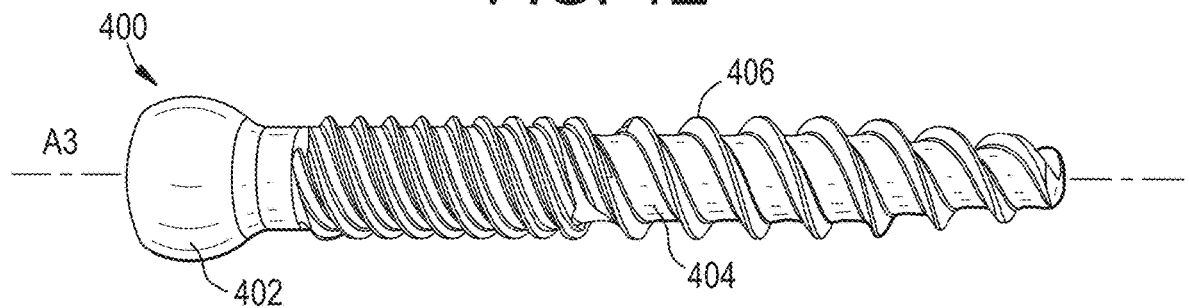

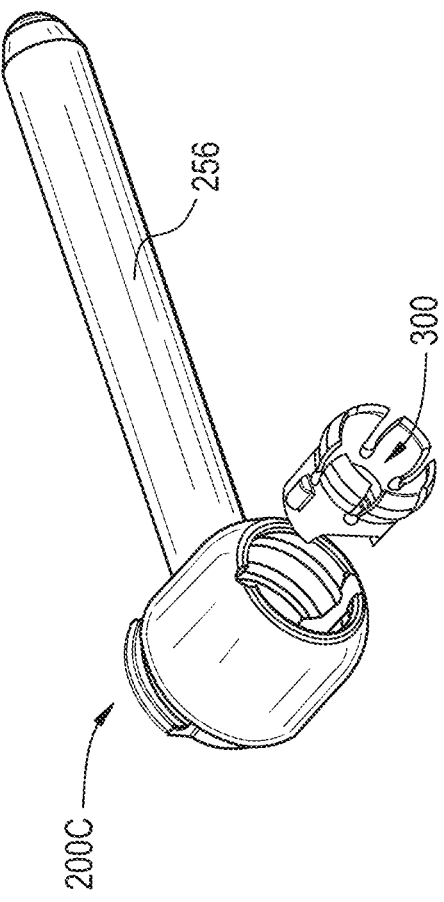
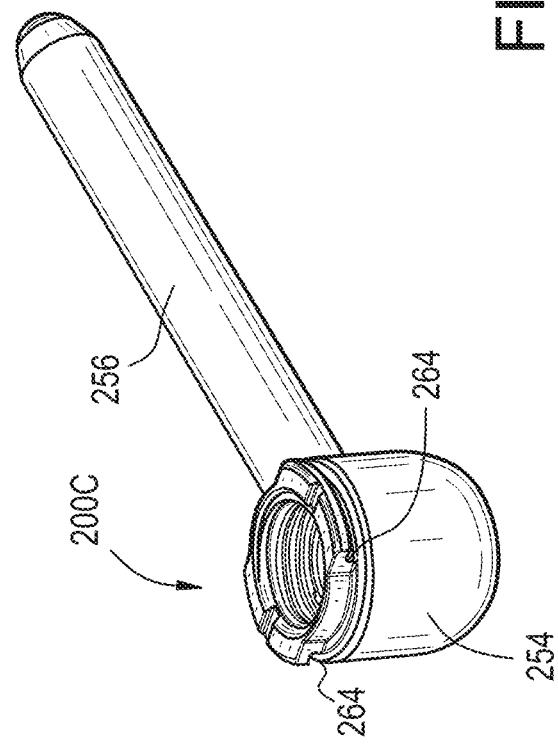
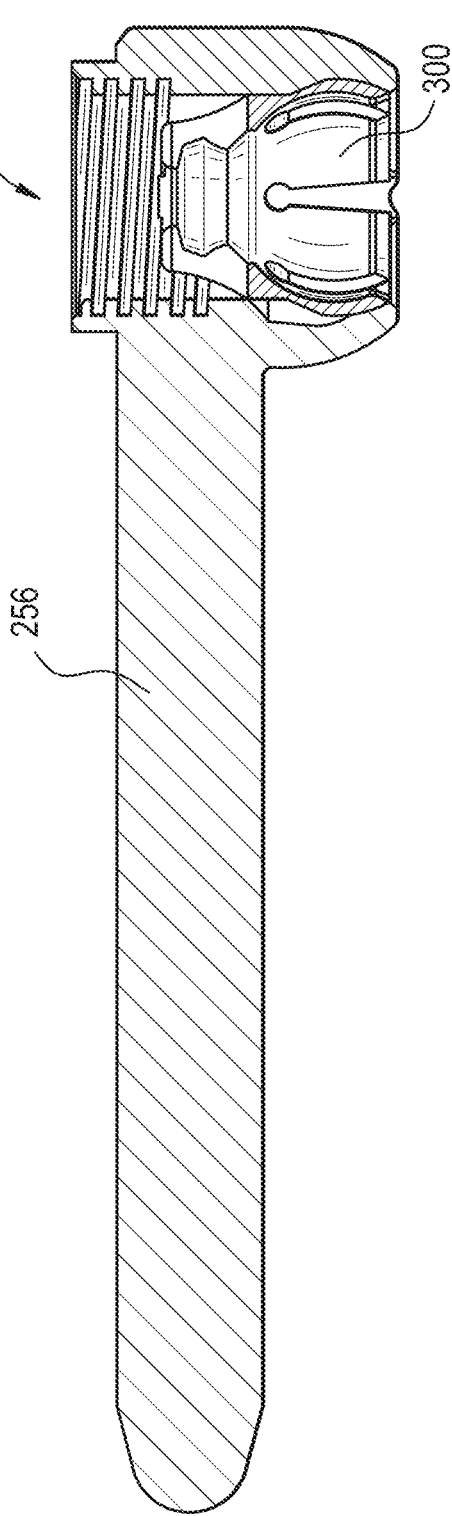

FIG. 5I
FIG. 5J
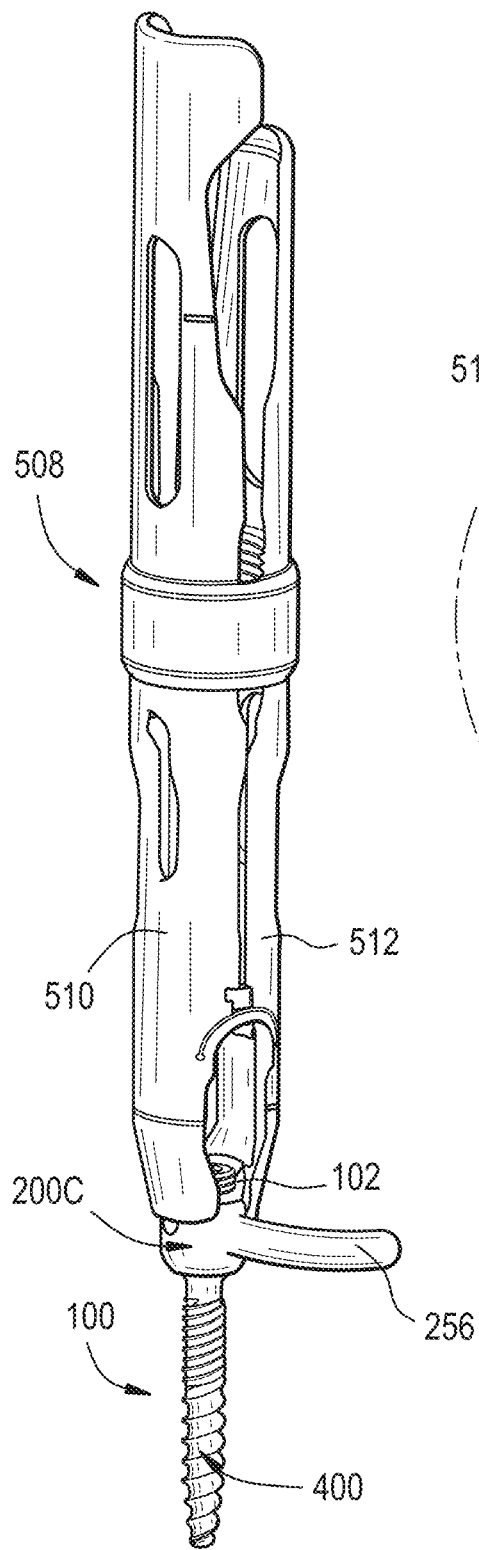
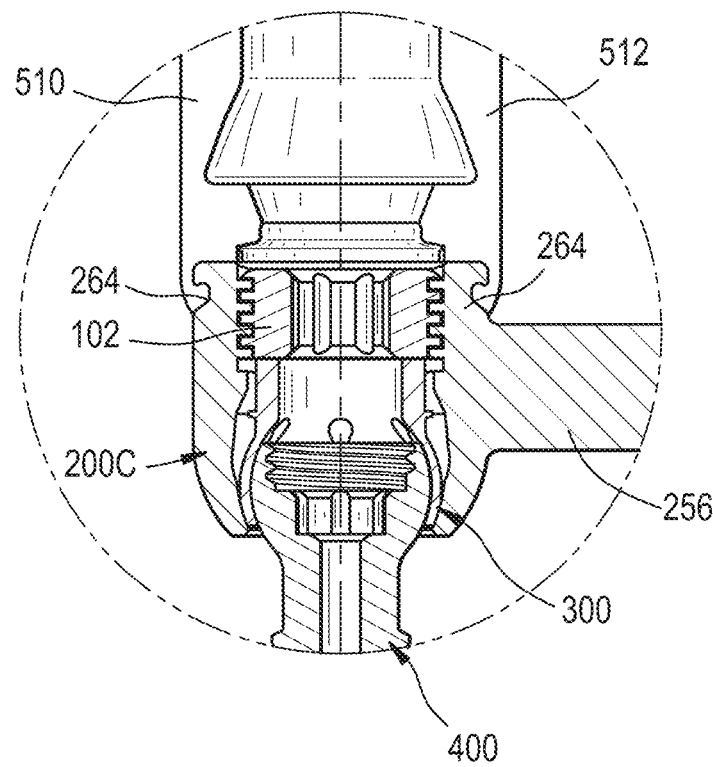

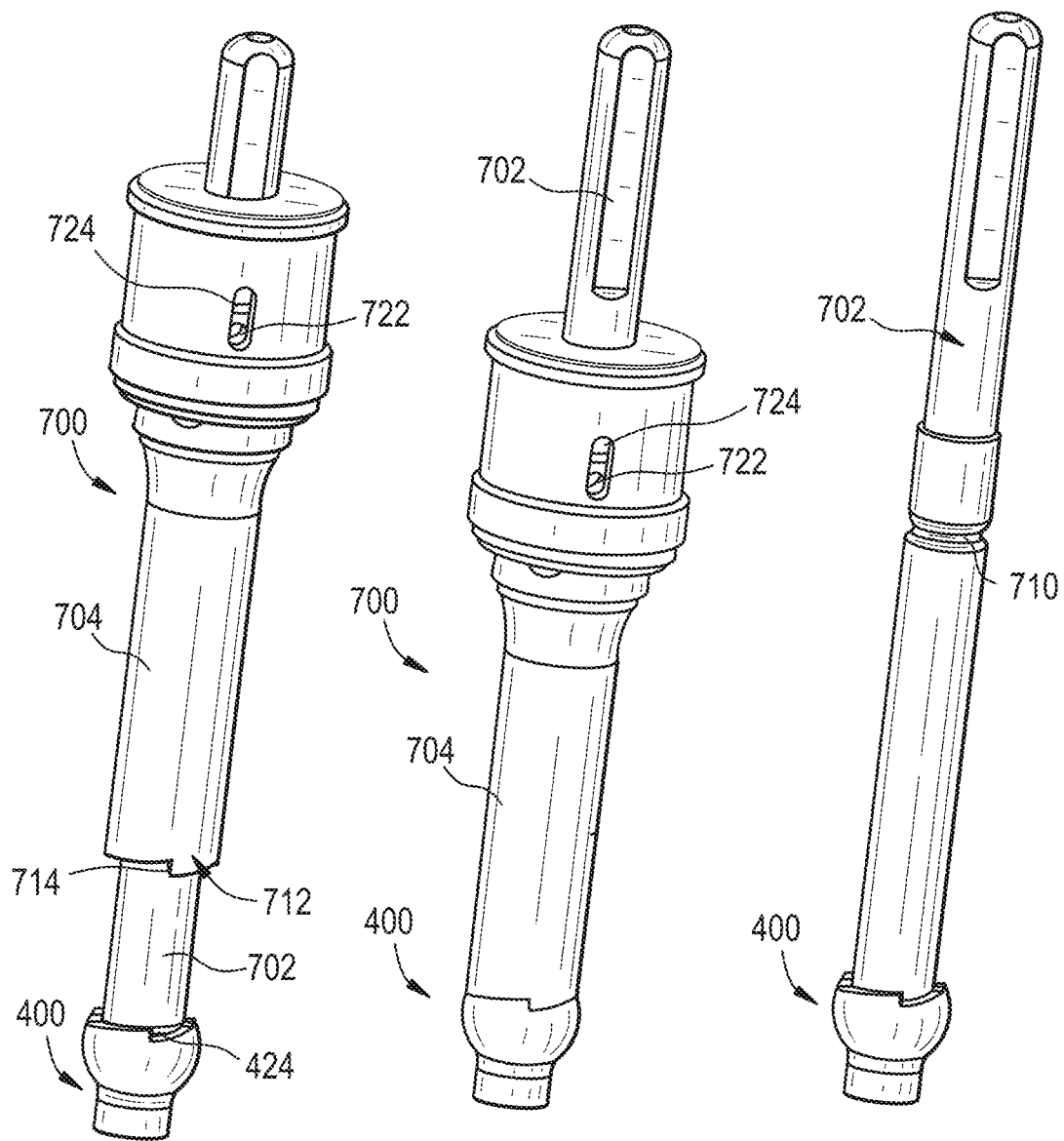

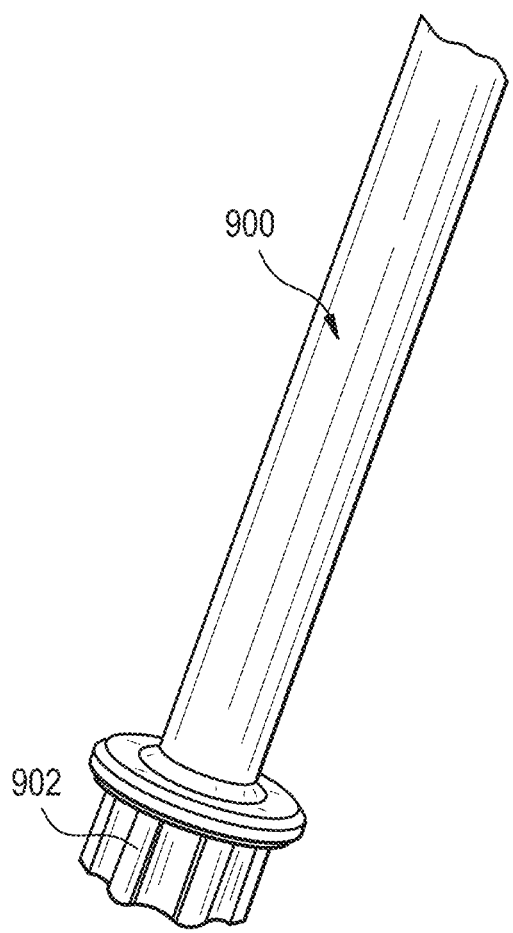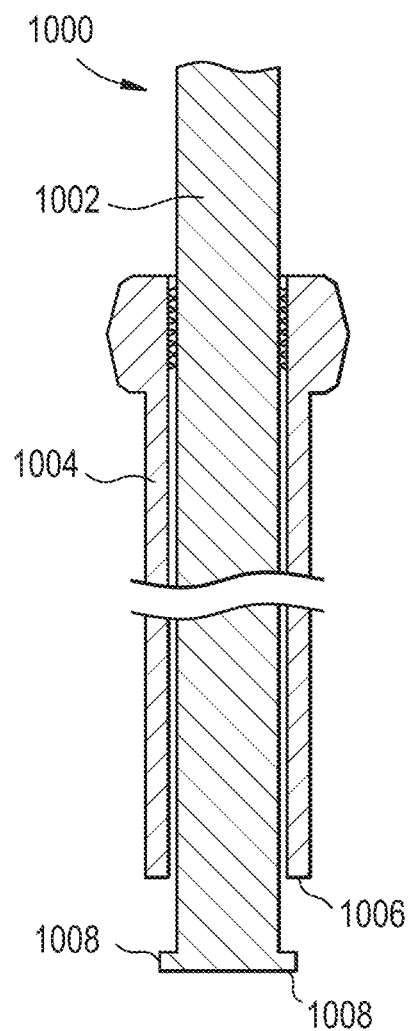

FIG. 11E
FIG. 11F
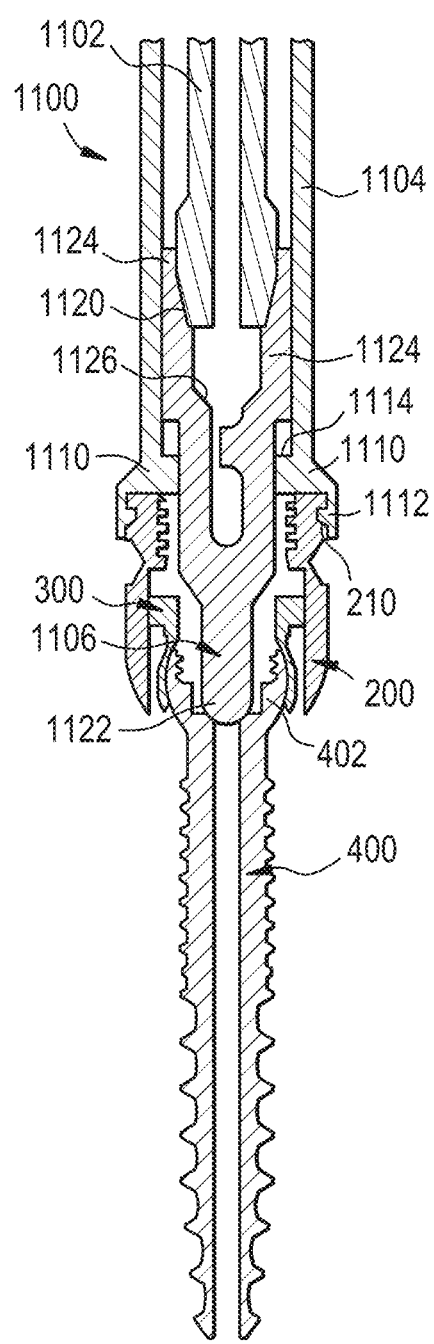
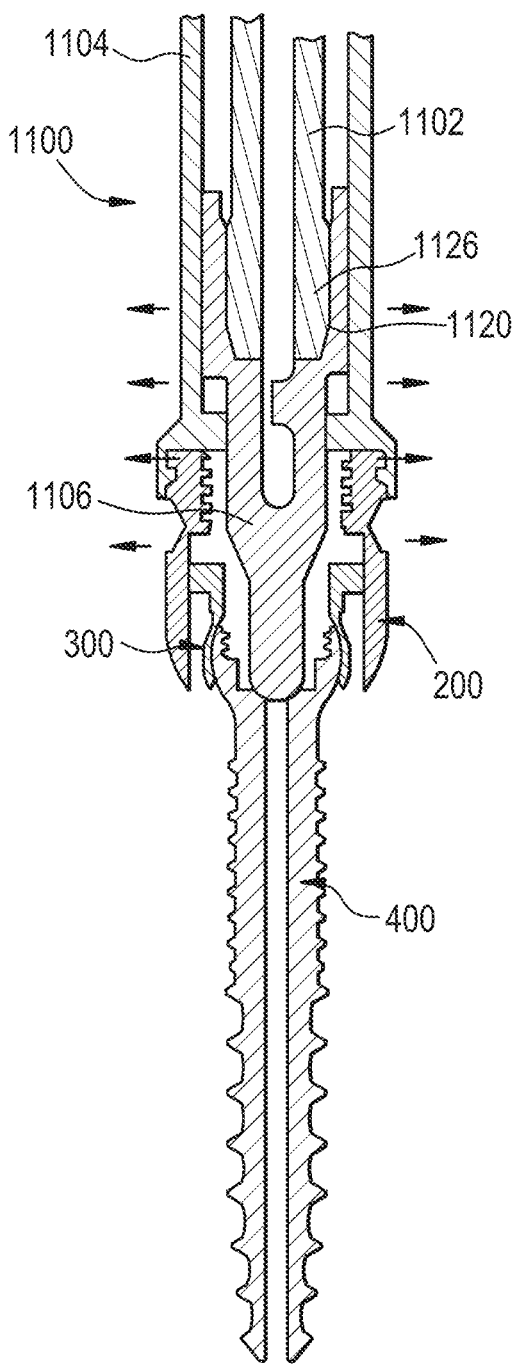

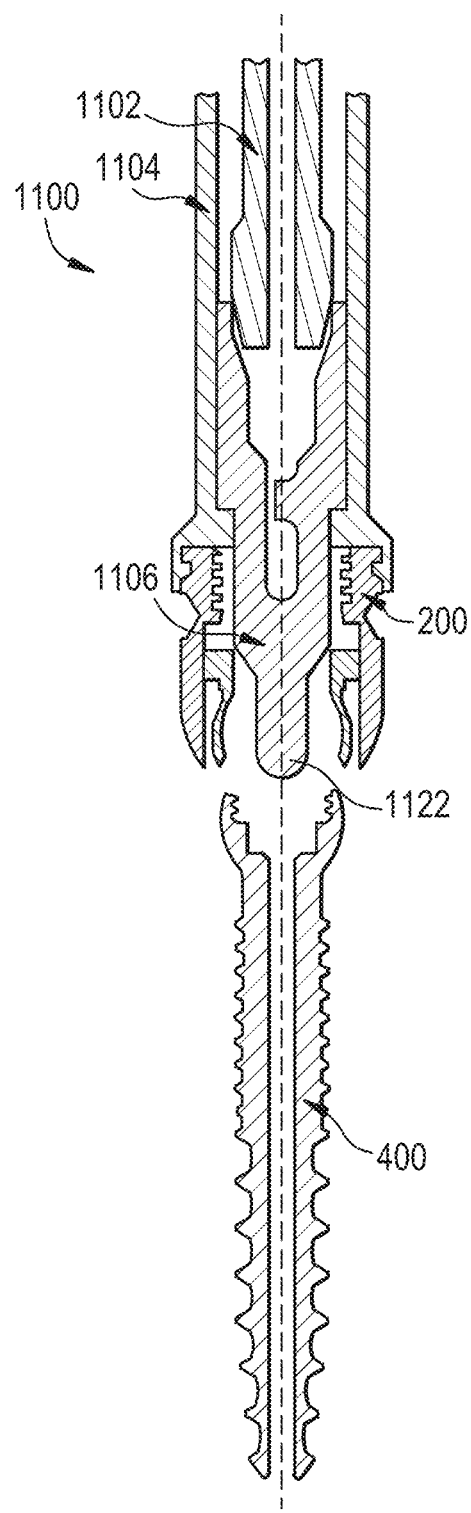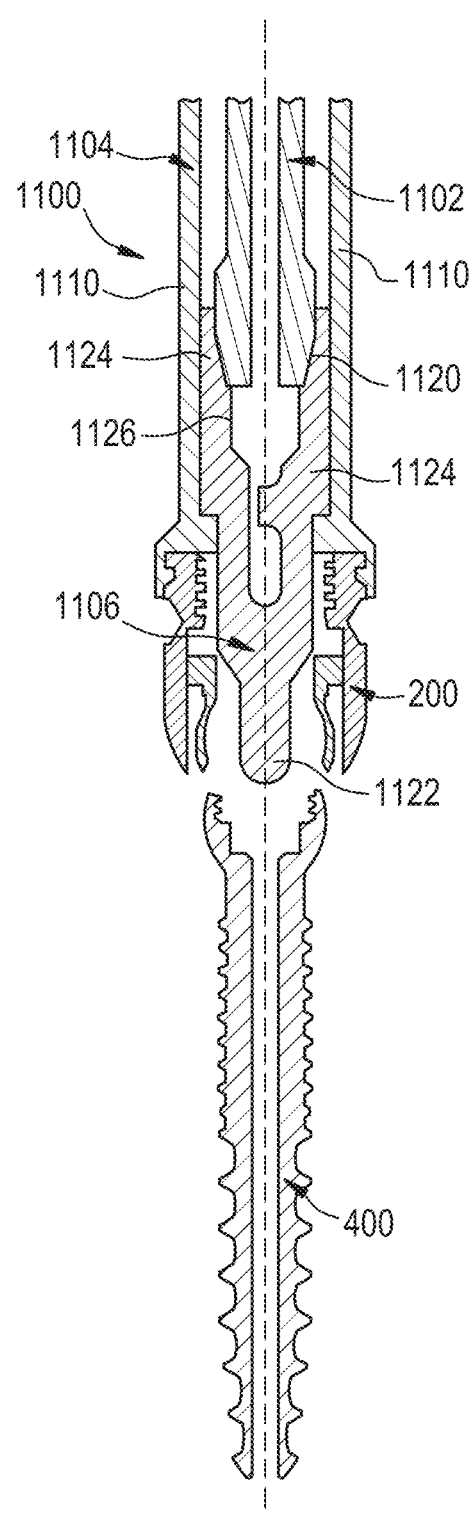

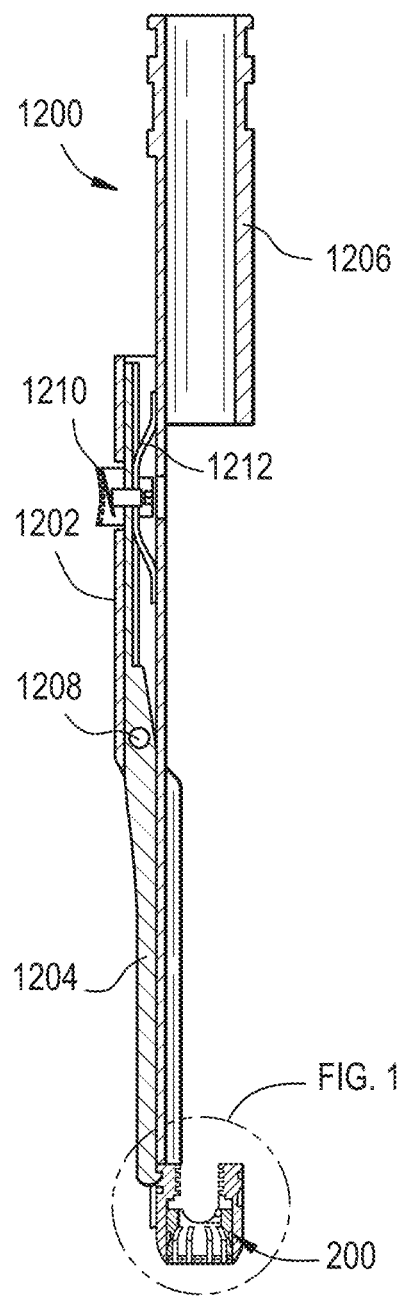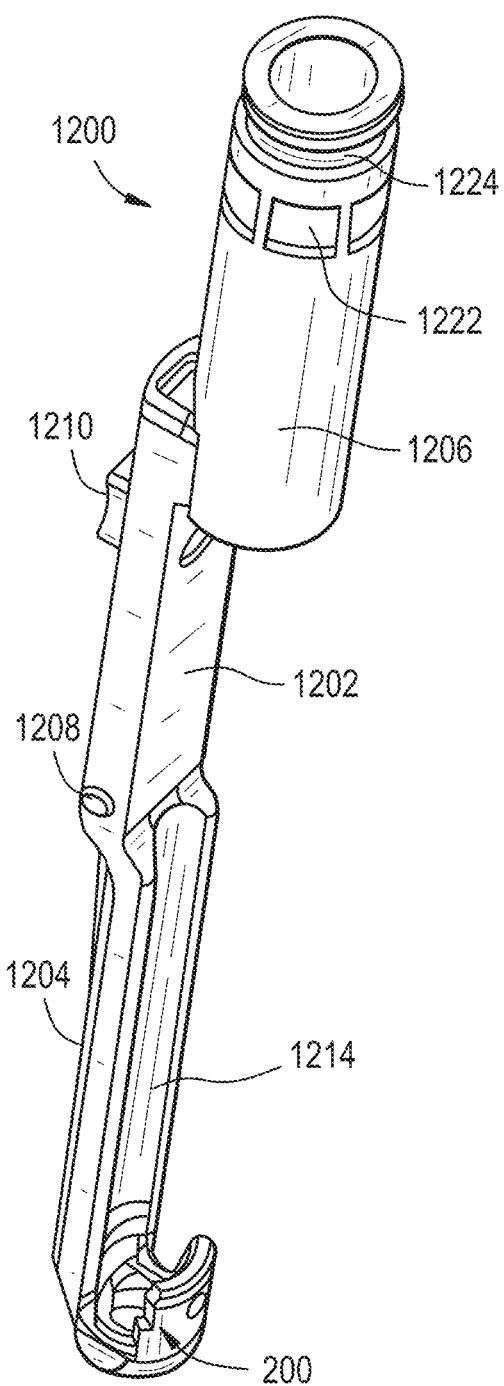

FIG. 13A
FIG. 13B
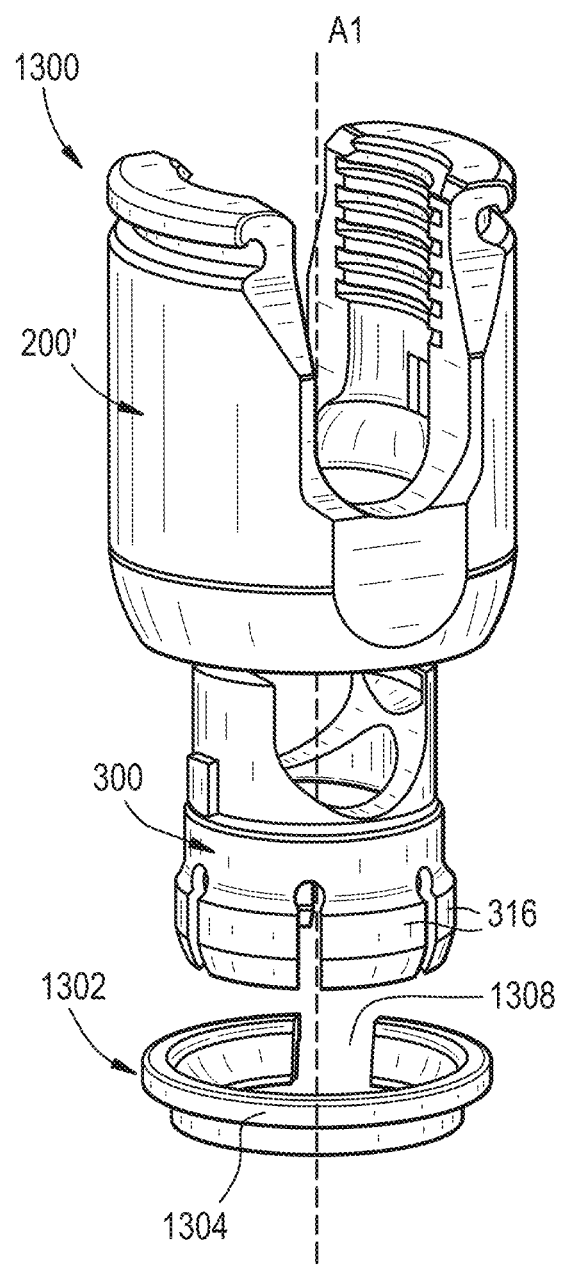
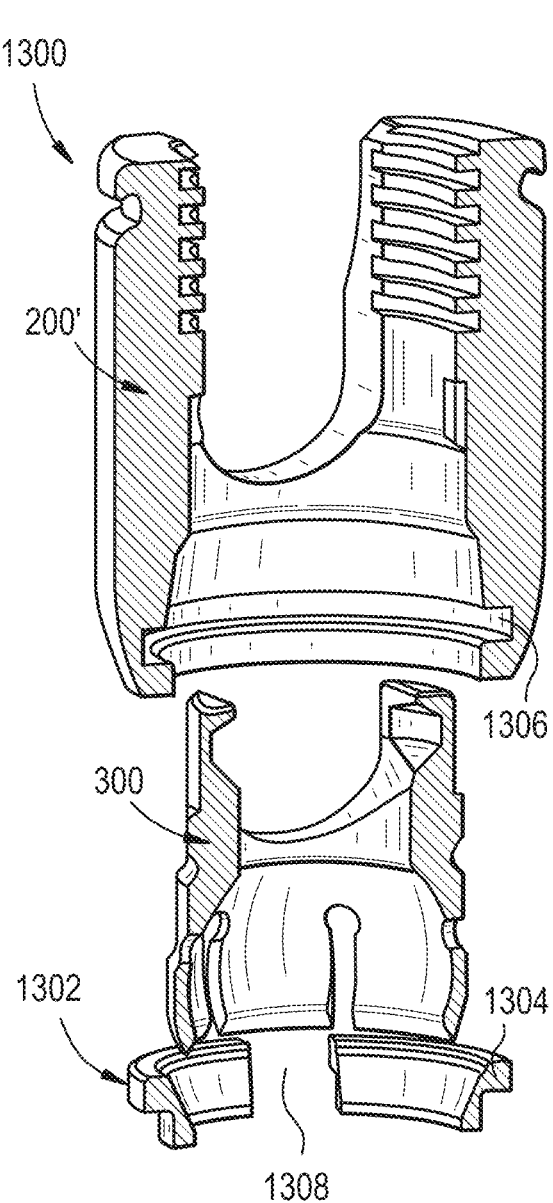

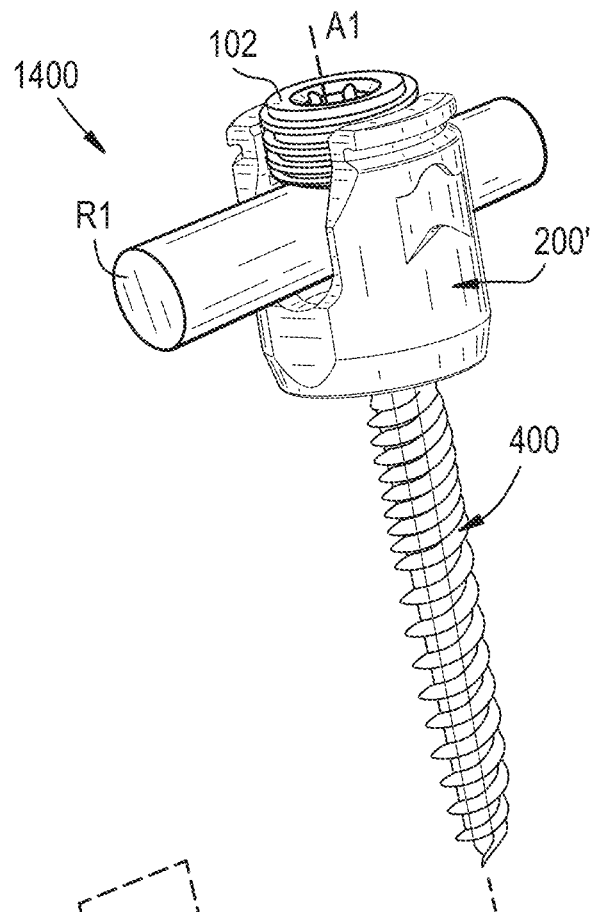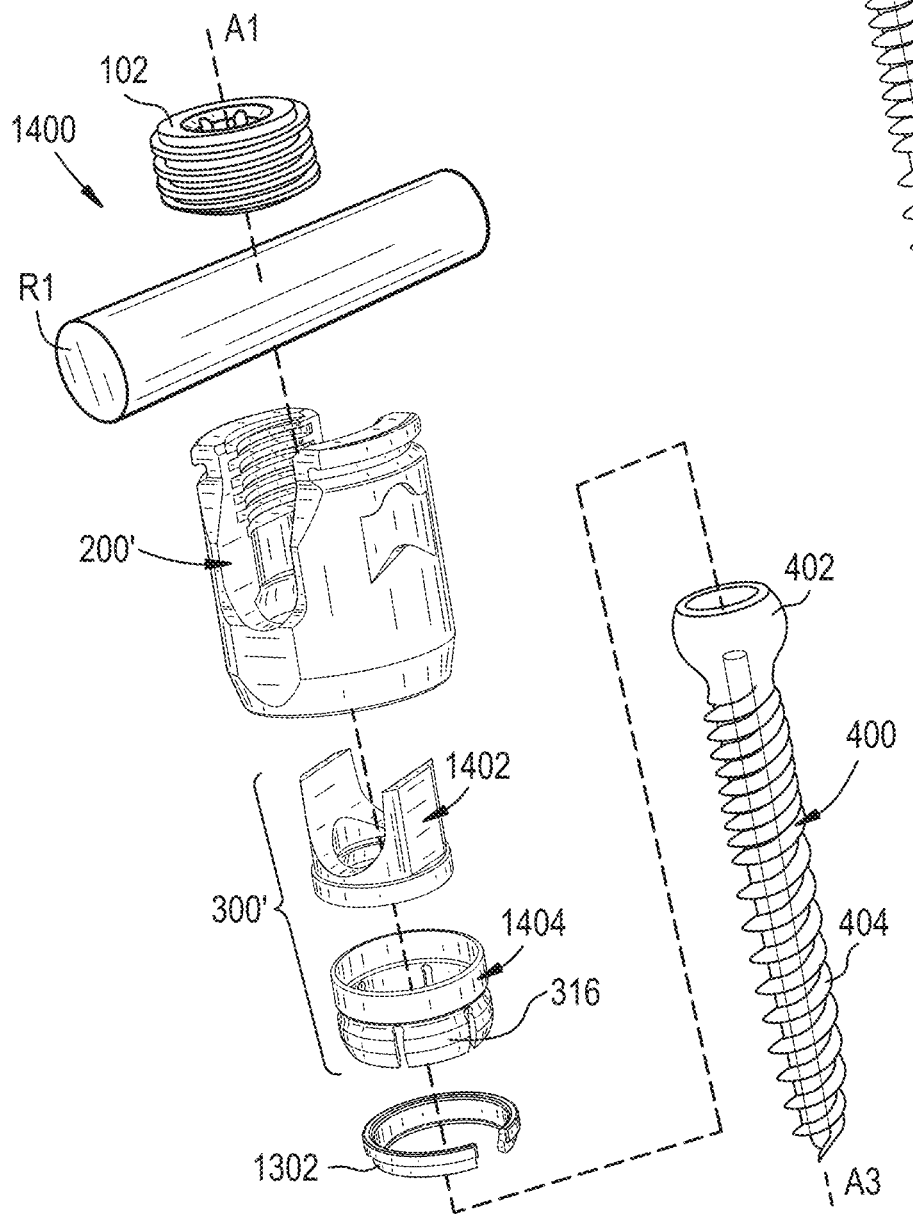

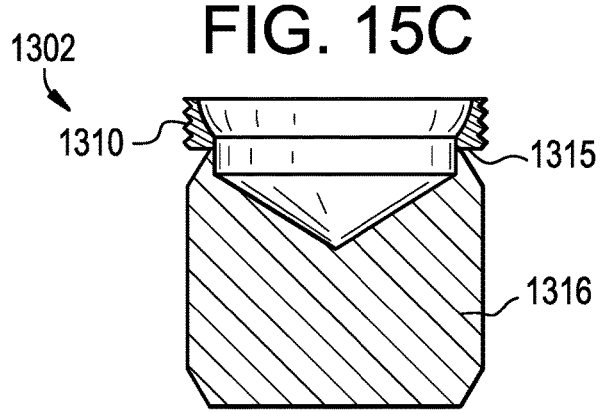
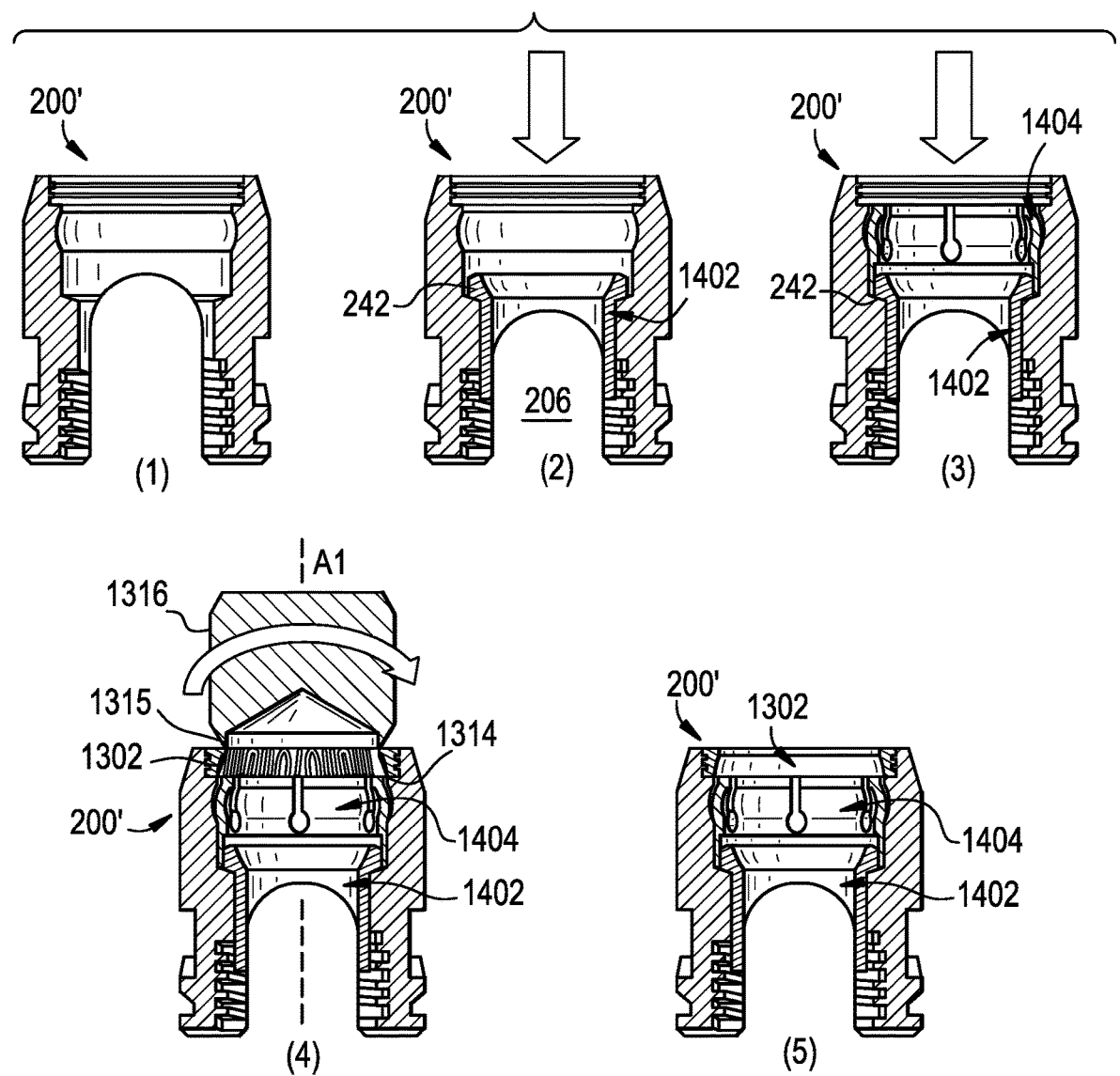

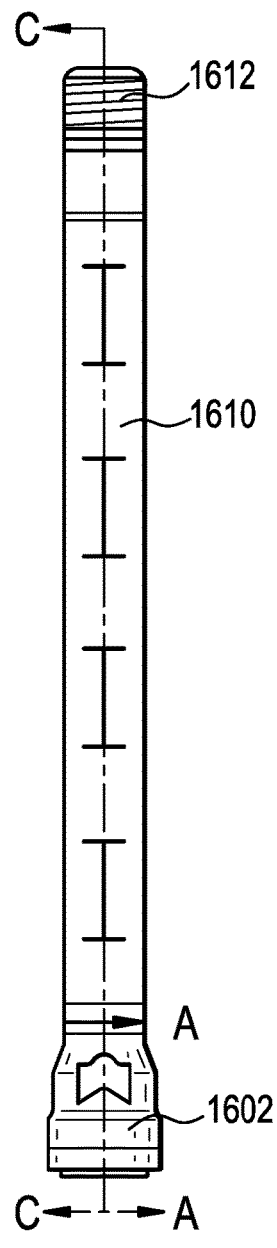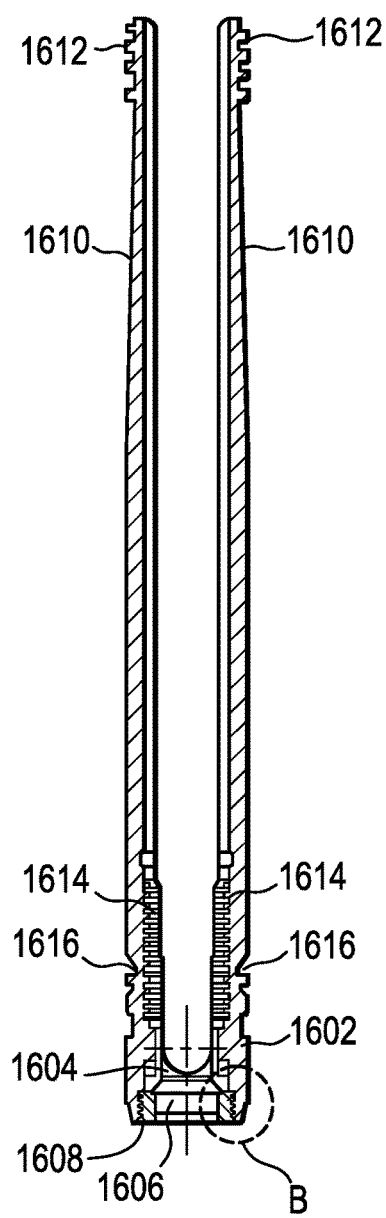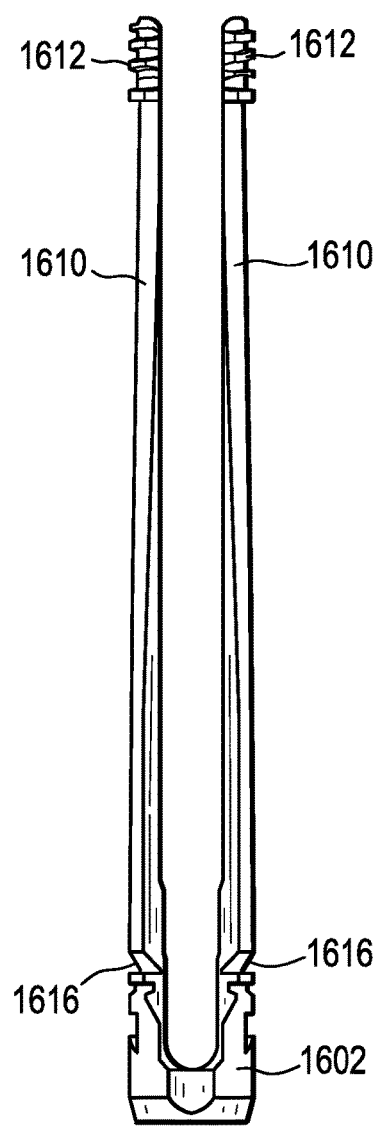

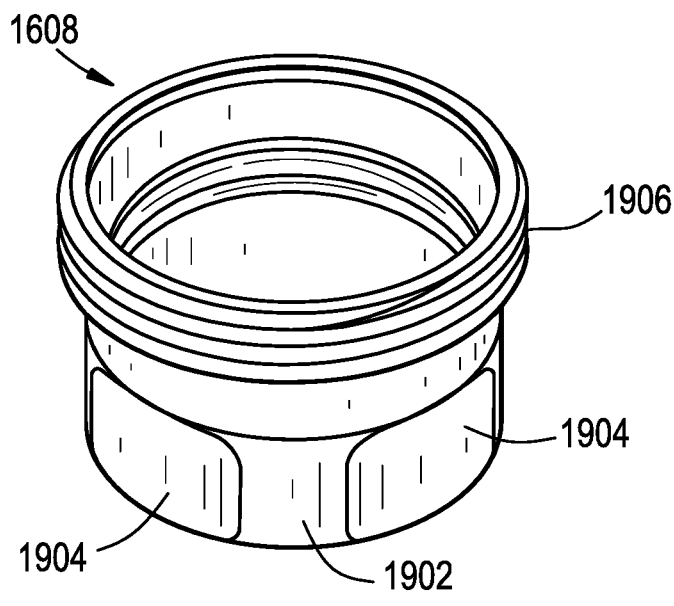
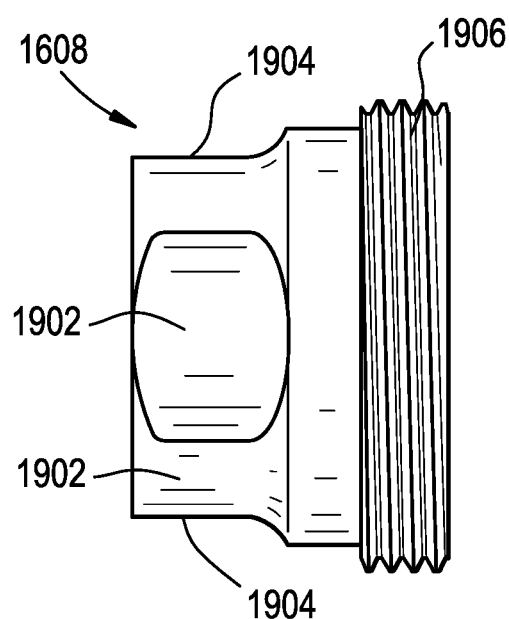
FIG. 19A
FIG. 19B
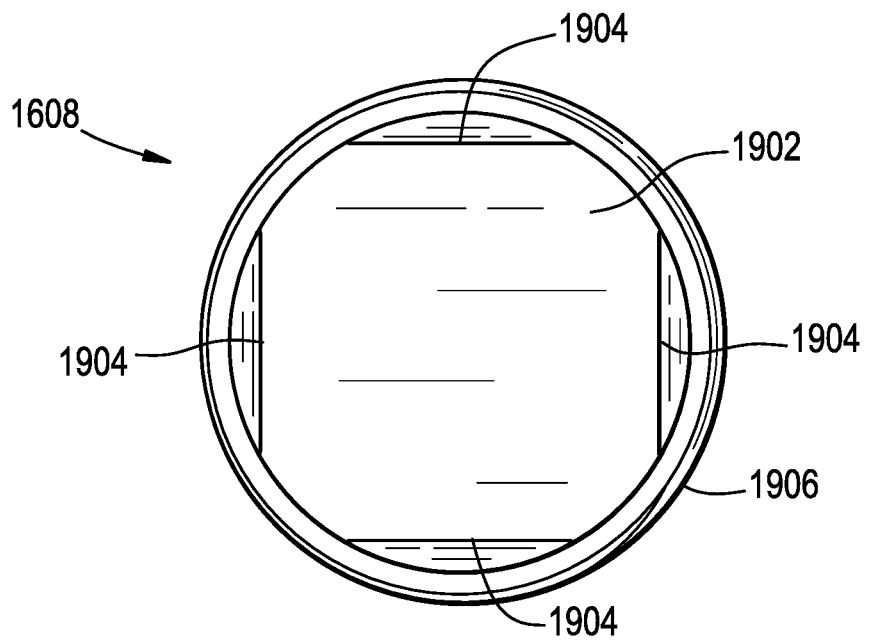
FIG. 19C

BONE ANCHOR ASSEMBLIES AND RELATED INSTRUMENTATION

CROSS-REFERENCE TO RELATED APPLICATIONS

This application is a continuation-in-part of U.S. application Ser. No. 15/623,444, filed on Jun. 15, 2017. U.S. application Ser. No. 15/623,444 is a continuation-in-part of U.S. application Ser. No. 15/208,847, filed on Jul. 13, 2016. U.S. application Ser. No. 15/623,444 is also a continuation-in-part of U.S. application Ser. No. 15/208,872, filed on Jul. 13, 2016. The entire contents of each of these applications is hereby incorporated by reference herein.

FIELD

Bone anchor assemblies and related instrumentation are disclosed herein.

BACKGROUND

Bone anchor assemblies can be used in orthopedic surgery to fix bone during healing, fusion, or other processes. In spinal surgery, for example, bone anchor assemblies can be used to secure a spinal fixation element to one or more vertebrae to rigidly or dynamically stabilize the spine. Bone anchor assemblies can also be used as an engagement point for manipulating bone (e.g., distracting, compressing, or rotating one vertebra with respect to another vertebra, reducing vertebral or long bone fractures, and so forth).

When performing various surgeries, such as spinal decompression, deconstruction, and fusion procedures, spatial anatomical awareness and direct visualization can be challenging for the surgeon. For example, these procedures can be disruptive to local native anatomy, implant and instrument geometry and configuration can obscure visualization, and trends in less-invasive surgery demand smaller working channels. In view of these and other challenges, there is a continual need for improved bone anchor assemblies and related instrumentation.

SUMMARY

Bone anchor assemblies and related instrumentation are disclosed herein. In some embodiments, a modular bone anchor assembly allows for a bone anchor to be driven into bone and a head or receiver member to be attached thereto at some later point in time. The bone anchor can have a smaller footprint than the complete assembly, which can improve visualization and anatomical spatial awareness during insertion of the bone anchor and during other surgical steps performed prior to attaching the head or receiver member to the bone anchor. A variety of modular head types are disclosed, as are various instruments for driving a bone anchor, attaching a head to a bone anchor, removing a head from a bone anchor, and making a unilateral attachment to a head of a bone anchor assembly. Drive interfaces for driving a bone anchor are disclosed, as are features that allow a bone anchor to act as a fixation point for soft tissue retraction, disc space distraction, derotation, and the like.

In some embodiments, a bone anchor assembly can include a head that defines a cavity, the head including proximal and distal ends that define a central proximal-distal axis; a collet disposed in the cavity, the collet comprising a plurality of fingers configured to expand radially-outward to retain the collet within the cavity; and a shank having a head portion retained within the collet.

The head can include first and second opposed arms that define a rod-receiving recess therebetween. Each arm can include a cross-section that facilitates a dovetail unilateral mating with an attachment instrument. Each arm can include a cross section defined by an outer surface, an inner surface, and first and second engagement surfaces extending between the inner and outer surfaces. The first and second engagement surfaces can extend at an oblique angle with respect to a plane defined by the central proximal-distal axis of the head and a central axis of the rod-receiving recess. The first and second engagement surfaces can be angled towards each other as the surfaces approach the central proximal-distal axis of the head. The cavity can include one or more keyways in which the collet is slidably received to restrict rotation of the collet relative to the head while allowing longitudinal translation of the collet relative to the head. The head can include opposed first and second arms, each of the arms having a reduction tab that extends proximally therefrom. The head can include opposed first and second arms that define a first rod-receiving recess therebetween and a lateral wing portion that defines a second rod-receiving recess therein. The head can include an integral rod portion. The collet can be insertable into a distal end of the head. The collet can be longitudinally translatable within the cavity. The collet can include one or more wings slidably received within keyways formed in the head. The collet can include first and second opposed arms that define a rod-receiving recess therebetween. Each arm of the collet can include a recess formed on an interior surface thereof for engagement with a removal or assembly instrument. The recess can be open to both lateral ends of the arm. The recess can include a proximal-facing surface, a distal-facing surface, a radially-inward facing surface, and an abutment surface that connects the proximal-facing, distal-facing, and inward-facing surfaces such that the recess is open to only one lateral end of the arm. The collet can be retained in the head without swaging. The fingers of the collet can be configured to deform from a resting position as the collet is loaded into a distal end of the cavity. The cavity can include: a proximal portion that defines a seat that faces in a proximal direction; a middle portion that defines a spherical seat that faces in a proximal direction; and a first shelf that projects radially-inward into the cavity, the first shelf being defined at the transition between the proximal and middle portions of the cavity. The cavity can include: a distal portion that defines a seat that faces in a distal direction; and a second shelf that projects radially-inward into the cavity, the second shelf being defined at the transition between the middle and distal portions of the cavity. The first shelf can bear against the exterior surfaces of the fingers to deform the fingers radially-inward from the resting position as the collet is inserted into the cavity. The fingers can be configured to expand radially-outward within the proximal portion of the cavity to retain the collet in the cavity. The fingers of the collet can be configured to deform from a resting position as the head portion of the shank is loaded into a distal end of the collet and, once the head portion is advanced into the collet, the fingers can be configured to return towards their resting position to capture the head portion within the collet. The shank can be free to pivot relative to the collet when the head portion is received within the fingers of the collet before the collet is locked to the head. Proximal advancement of the head with respect to the collet can wedge the collet fingers between the head portion of the shank and the interior of the cavity, thereby locking movement of the shank with respect to the head. The head portion of the shank can include a drive interface for applying torque to the shank or for attaching instruments to the shank. The drive interface can include a cavity with an internal thread, the internal thread being interrupted by a plurality of longitudinal channels. A proximal-facing surface of the shank can include a plurality of proximally-extending projections for applying counter-torque to the shank. Each projection can include a ramped surface that extends obliquely from a plane transverse to a central longitudinal axis of the shank and an abutment surface that extends parallel to the central longitudinal axis of the shank. Each projection can include a first abutment surface that extends parallel to a central longitudinal axis of the shank and a second abutment surface that extends parallel to the central longitudinal axis of the shank.

In some embodiments, a method of assembling a bone anchor assembly includes inserting a collet into a cavity formed in a head of the bone anchor assembly by: deforming a plurality of fingers of the collet radially-inward to allow the collet to pass through a distal opening of the cavity; and expanding the plurality of fingers radially-outward once the collet is disposed in the cavity to retain the collet within the cavity; and after inserting the collet into the cavity, inserting a head portion of a bone anchor into the collet by: deforming the fingers of the collet radially-outward to allow the head portion of the bone anchor to pass through a distal opening defined by the fingers; and collapsing the plurality of fingers radially-inward once the head portion is disposed within the collet to retain the head portion within the collet.

The method can include translating the collet distally within the cavity to wedge the fingers of the collet between the head portion of the bone anchor and an interior surface of the cavity. Translating the collet distally can include tightening a set screw to the head of the bone anchor assembly to urge a rod disposed in the head into contact with the collet to move the head proximally. The method can include driving the bone anchor into bone prior to attaching the collet and the head to the bone anchor.

In some embodiments, a head insertion instrument includes a sleeve having opposed arms movable towards and away from one another to selectively couple the sleeve to a head of a bone anchor assembly; a push rod disposed within the sleeve and configured to translate axially with respect to the sleeve, the push rod having a first bearing surface; and a release element disposed within the sleeve and configured to translate axially with respect to the sleeve, the release element including a second bearing surface and opposed arms aligned with the opposed arms of the sleeve; wherein the instrument prevents separation of a head of a bone anchor assembly from the sleeve when the head is not fully seated on a bone anchor.

When a head coupled to the sleeve is not fully seated on a bone anchor, advancement of the push rod can advance the release element without spreading the arms of the release element or the arms of the sleeve, thereby preventing separation of the head from the instrument. When a head coupled to the sleeve is fully seated on a bone anchor, advancement of the push rod can cause the first bearing surface to cam over the second bearing surface to spread the arms of the release element and the arms of the sleeve, thereby separating the head from the instrument. The arms of the sleeve can include arcuate shelves that extend radially-inward from the arms, the shelves being configured to be received within corresponding grooves formed in a head of a bone anchor assembly. The arms of the sleeve can include a shoulder to limit distal travel of the release element relative to the sleeve. A proximal end of the push rod can be coupled to a button or lever that can be depressed to translate the push rod longitudinally with respect to the sleeve. The push rod can be biased proximally with respect to the sleeve. The first and second bearing surfaces can be ramped. The first bearing surface can be formed on an exterior of the push rod and the second bearing surface can be formed on an interior of the arms of the release element. The release element can include a distal projection configured to protrude from a distal end of the sleeve to contact a bone anchor. The release element can include opposed tabs that slide within corresponding channels formed in the sleeve to restrict rotation of the release element relative to the sleeve.

In some embodiments, a method of assembling a bone anchor assembly includes driving a bone anchor of the bone anchor assembly into a bone; engaging opposed arms of a sleeve of an inserter instrument with a head of the bone anchor assembly to couple the head to the sleeve; with the head coupled to the sleeve, inserting a proximal end of the bone anchor into a distal end of the head; and advancing a push rod distally within the sleeve, wherein advancing the push rod separates the head from the sleeve only when the head is fully seated on the bone anchor.

When the head is not fully seated on the bone anchor, advancement of the push rod can advance a release element within the sleeve without spreading the arms of the sleeve, thereby preventing separation of the head from the instrument. When the head is fully seated on the bone anchor, advancement of the push rod can cause a first bearing surface of the push rod to cam over a second bearing surface of a release element disposed within the sleeve to spread the arms of sleeve, thereby separating the head from the instrument. The method can include ejecting the bone anchor from the head when the push rod is advanced distally while the head is not fully seated on the bone anchor. The head can be ejected by a distal projection of a release element slidably disposed in the sleeve.

In some embodiments, a driver instrument includes a sleeve having an engagement feature for engaging a corresponding engagement feature of a bone anchor, the sleeve including a throughbore in which a ball bearing is disposed; a driver shaft rotatably disposed within the sleeve, a distal end of the driver shaft being configured to engage a bone anchor to drive the bone anchor into bone, the driver shaft having a first groove formed therein; a collar defining a cavity in which a proximal portion of the sleeve is received and having a second groove formed therein; wherein the collar is slidable between a locked position in which the driver shaft is maintained at a fixed longitudinal position with respect to the sleeve and is free to rotate with respect to the sleeve, and an unlocked position in which the driver shaft is free to translate longitudinally with respect to the sleeve and is free to rotate with respect to the sleeve.

In the locked position the second groove of the collar can be offset from the throughbore of the sleeve such that the collar holds the ball bearing in a position in which the ball bearing is partially disposed in the first groove formed in the driver shaft. In the unlocked position the second groove of the collar can be aligned with the throughbore of the sleeve, allowing the ball bearing to move in a radially-outward direction, out of engagement with the first groove formed in the driver shaft. The instrument can include a bias element configured to bias the sleeve distally relative to the collar. The engagement feature of the sleeve can include a plurality of ramped projections that extend distally from the distal-facing surface of the sleeve, each projection having a ramped surface that extends obliquely from a plane transverse to a central longitudinal axis of the sleeve and an abutment surface that extends parallel to the central longitudinal axis of the sleeve.

In some embodiments, a driver instrument can include a sleeve having an engagement feature for engaging a corresponding engagement feature of a bone anchor; a driver shaft rotatably disposed within the sleeve, a distal end of the driver shaft being configured to engage a bone anchor to drive the bone anchor into bone, the driver shaft having a thread formed on an exterior surface thereof; a collar defining a cavity in which a proximal portion of the sleeve is received and having an interior thread formed therein such that the collar threadably engages the driver shaft; wherein the collar is rotatable with respect to the driver shaft to advance the sleeve longitudinally with respect to the driver shaft without rotating the sleeve relative to the driver shaft.

The collar can include a hole formed therein that is aligned with a groove formed in the sleeve. The instrument can include a pin inserted through the hole and into the groove to maintain the sleeve at a fixed longitudinal position relative to the collar while allowing the sleeve to rotate relative to the collar. The engagement feature of the sleeve can prevent rotation of the sleeve relative to a bone anchor in both clockwise and counterclockwise directions. The engagement feature of the sleeve can include a plurality of projections that extend distally from the distal-facing surface of the sleeve, each of the projections including a first abutment surface that extends parallel to a central longitudinal axis of the sleeve and a second abutment surface that extends parallel to the central longitudinal axis of the sleeve. The engagement feature of the sleeve can include a plurality of angled teeth.

In some embodiments, a unilateral attachment instrument includes a body that defines a recess configured to receive an arm of a receiver member of a bone anchor assembly therein, thereby preventing lateral translation and axial rotation of the receiver member relative to the body, the body defining a central longitudinal axis; and a lock arm pivotally coupled to the body and configured to engage an arm of a receiver member of a bone anchor assembly to prevent axial translation of the receiver member relative to the body.

The central longitudinal axis of the body can be offset from a central longitudinal axis of a receiver member when an arm of the receiver member is disposed in the recess. The body can include a tube portion having a central longitudinal axis that is offset from the central longitudinal axis of the body. The central longitudinal axis of the tube portion can be coaxial with a central longitudinal axis of a receiver member when an arm of the receiver member is disposed in the recess. An interior of the tube portion can be threaded. An exterior of the tube portion can include at least one of a flat and an annular groove. The instrument can include a release button configured to pivot the lock arm relative to the body. The recess can be configured to grip multiple sides of an arm of a receiver member. The recess can be configured to mate with a receiver member by a dovetail connection. The recess can include a curved face and first and second planar faces that extend from the curved face. When coupled to a receiver member having a rod-receiving recess, the first and second planar faces can extend at an oblique angle with respect to a plane defined by a central longitudinal axis of the receiver member and a central axis of the rod-receiving recess. The first and second planar faces can be angled towards each other as the faces approach the central longitudinal axis of a receiver member received in the recess. The lock arm can include a ridge that projects radially-inward from the arm to engage a corresponding groove formed in a receiver member received in the recess.

In some embodiments, a bone anchor assembly can include a receiver member having proximal and distal ends that define a central proximal-distal axis; an insert attached to the receiver member, the insert and the receiver member defining a cavity; a collet disposed in the cavity and retained within the cavity by the insert, the collet including a plurality of fingers; and a shank that extends through the insert, the shank having a head portion retained within the fingers of the collet.

The insert can include a ridge received within a groove formed in the receiver member to attach the insert to the receiver member. The insert can be radially collapsible and expandable to facilitate insertion of the insert into the receiver member. The insert can be threaded into an open distal end of the receiver member. The collet can be insertable into the distal end of the receiver member without deforming the collet. The receiver member can include first and second opposed arms that define a rod-receiving recess therebetween. The fingers of the collet can be configured to deform from a resting position as the head portion of the shank is loaded into a distal end of the collet and, once the head portion is advanced into the collet, the fingers can be configured to return towards their resting position to capture the head portion within the collet. The shank can be free to pivot relative to the collet when the head portion is received within the fingers of the collet before the collet is locked to the receiver member. Proximal advancement of the receiver member with respect to the collet can wedge the collet fingers between the head portion of the shank and the interior of the insert, thereby locking movement of the shank with respect to the receiver member. The collet can include a compression cap and a collet ring. The compression cap and the collet ring can be independently longitudinally-translatable relative to the receiver member when disposed within the cavity. The compression cap can be slidably received within an opening formed in the collet ring. The collet ring can include a proximal opening in which the compression cap is slidably received and the fingers of the collet can extend distally from the collet ring. The compression cap can include one or more flats that interact with respective one or more flats of the receiver member to limit rotation of the compression cap relative to the receiver member about the central proximal-distal axis. The cavity can include an upper portion having a cylindrical inner sidewall that constrains a cylindrical outer sidewall of the collet ring when the collet ring is received therein. Tightening a closure element to the receiver member can (i) urge a bearing surface of the compression cap against a proximal portion of the head of the shank and (ii) urge the collet fingers against a distal portion of the head of the shank.

In some embodiments, a method of assembling a bone anchor assembly can include inserting a collet into a cavity formed in a receiver member of the bone anchor assembly by passing the collet through a distal opening of the cavity without deforming the collet; after inserting the collet into the cavity, attaching an insert to the receiver member of the bone anchor assembly to prevent the collet from moving distally through the distal opening of the cavity; and after attaching the insert to the receiver member, inserting a head portion of a bone anchor through a central opening of the insert and into the collet by: deforming the fingers of the collet radially-outward to allow the head portion of the bone anchor to pass through a distal opening defined by the fingers; and collapsing the plurality of fingers radially-inward once the head portion is disposed within the collet to retain the head portion within the collet.

The method can include translating the receiver member proximally relative to the collet to wedge the fingers of the collet between the head portion of the bone anchor and an interior surface of the insert. Translating the receiver member proximally can include tightening a set screw to the receiver member to urge a rod disposed in the receiver member into contact with the collet to move the receiver member proximally. The method can include driving the bone anchor into bone prior to attaching the collet and the receiver member to the bone anchor. The collet can include a compression cap and a collet ring, the fingers extending distally from the collet ring. The method can include independently longitudinally translating the compression cap and the collet ring within the cavity. The method can include sliding the compression cap axially within an opening formed in the collet ring. The compression cap can include one or more flats that interact with respective one or more flats of the receiver member to limit rotation of the compression cap relative to the receiver member about a central proximal-distal axis of the receiver member. The method can include tightening a closure element to the receiver member to (i) urge a bearing surface of the compression cap against a proximal portion of the head of the bone anchor and (ii) urge the collet fingers against a distal portion of the head of the bone anchor.

In certain embodiments, a method of assembling a bone anchor assembly can include inserting a component into a cavity formed in a receiver member of the bone anchor assembly by passing the component through a distal opening of the cavity, and, after inserting the component into the cavity, attaching an insert to the receiver member to prevent the component from moving distally through the distal opening of the cavity. Further, attaching the insert can include applying torque to a drive feature of the insert to advance the insert proximally relative to the receiver member until the insert bottoms out in the cavity and applying further torque to separate the drive feature from the insert at a shear portion.

In some embodiments, the drive feature can include a plug extending distally from a threaded portion of the insert, and the plug can have one or more flats for applying torque thereto. Further, the shear portion can be disposed between the plug and the threaded portion of the insert. In some embodiments, the shear portion can include a thin-walled annular section of material. In certain embodiments, the plug can be at least partially hollow to define an annulus of material to serve as the shear portion.

In some embodiments, the insert can bottom out against a distal-facing shoulder formed in the cavity. The distal facing shoulder can be flat, e.g., perpendicular to a longitudinal axis of the receiver member, or angled, e.g., oblique to the longitudinal axis of the receiver member.

In certain embodiments, the component can include a collet. In some embodiments, the component can include a compression cap. In some embodiments, the component can include a compression cap and a collet ring. In certain embodiments, the collet ring can include a plurality of fingers and the collet ring can be passed through the distal opening of the cavity without deflecting said fingers. In some embodiments, the method can further include, after attaching the insert to the receiver member, inserting a head portion of a bone anchor through a central opening of the insert and into the collet by deflecting the fingers of the collet radially-outward to allow the head portion of the bone anchor to pass through a distal opening defined by the fingers, and collapsing the plurality of fingers radially-inward once the head portion is disposed within the collet to retain the head portion within the collet.

Moreover, in some embodiments collapsing the plurality of fingers of the collet can apply a drag force to the head portion of the bone anchor to prevent unintended movement (e.g., articulation) between the receiver member and the bone anchor. And in some embodiments the method can further include inserting a spinal fixation element and a set screw into the receiver member to drive the receiver member proximally with respect to the collet, wedge the plurality of fingers of the collet between the head portion of the bone anchor and the receiver member, and lock movement of the bone anchor relative to the receiver member.

In some embodiments, a bone anchor assembly can include a receiver member having proximal and distal ends that define a central proximal-distal axis, the receiver member having a cavity formed therein, the cavity being open to the distal end of the receiver member. The assembly can further include a component disposed in the cavity, and an insert attached to the receiver member to retain the component within the receiver member. The insert can have a drive feature configured to shear off from the insert when the insert is bottomed out within the cavity and when sufficient torque is applied to the drive feature. Further, the drive feature can include a plug having one or more flats for applying torque thereto and the plug can be connected to the insert by a reduced thickness annular section of material.

In certain embodiments, the insert can include an exterior thread mated to an interior thread of the receiver member. In some embodiments, the component can include at least one of a collet ring and a compression cap. And in some embodiments the assembly can further include a shank that extends through the insert, where the shank can have a head portion retained between a plurality of fingers of the component.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

FIG. 4A is a perspective top view of the bone anchor of the bone anchor assembly of FIG. 1A;

FIG. 4B is a perspective bottom view of the bone anchor of FIG. 4A;

FIG. 4C is a top view of the bone anchor of FIG. 4A;

FIG. 4D is a sectional side view of the bone anchor of FIG. 4A;

FIG. 4E is a side view of the bone anchor of FIG. 4A;

FIG. 5F is a perspective view of a head having a built-in rod that can be used in the bone anchor assembly of FIG. 1A;

FIG. 5G is an exploded perspective view of the head of FIG. 5F shown with the collet of the bone anchor assembly of FIG. 1A;

FIG. 5H is a sectional side view of the head and collet of FIG. 5G;

FIG. 5I is a perspective view of a rod introducer instrument attached to the bone anchor assembly of FIG. 5F;

FIG. 5J is a sectional side view of the rod introducer instrument and bone anchor assembly of FIG. 5I;

FIG. 7E is a perspective view of a step in a method of driving a bone anchor using the driver instrument of FIG. 7A;

FIG. 7F is a perspective view of another step in a method of driving a bone anchor using the driver instrument of FIG. 7A;

FIG. 7G is a perspective view of another step in a method of driving a bone anchor using the driver instrument of FIG. 7A;

FIG. 9 is a perspective view of a driver instrument;

FIG. 10 is a sectional side view of a head removal instrument;

FIG. 11E is a sectional side view of the instrument of FIG. 11A attaching a head to a bone anchor;

FIG. 11F is a sectional side view of the instrument of FIG. 11A releasing from a head after the head is attached to a bone anchor;

FIG. 11G is a sectional side view of the instrument of FIG. 11A attempting to attach a head to a bone anchor;

FIG. 11H is a sectional side view of the instrument of FIG. 11A preventing release of a head due to insufficient attachment of the head to a bone anchor;

FIG. 12C is a sectional view of the instrument of FIG. 12A;

FIG. 12D is a perspective view of the instrument of FIG. 12A;

FIG. 13A is an exploded perspective view of a receiver member, collet, and insert of a bone anchor assembly;

FIG. 13B is a sectional exploded perspective view of the bone anchor assembly of FIG. 13A;

FIG. 14A is a perspective view of a bone anchor assembly and a spinal rod;

FIG. 14B is an exploded perspective view of the bone anchor assembly and spinal rod of FIG. 14A;

FIG. 15C is a sectional side view of a retaining insert of the bone anchor assembly of FIG. 15A;

FIG. 15D schematically illustrates a method of assembling the bone anchor assembly of FIG. 15A;

FIG. 16B is a side view of the bone anchor assembly of FIG. 16A;

FIG. 16C is a cross-sectional view of the bone anchor assembly of FIG. 16A taken along the line C-C in FIG. 16B;

FIG. 16D is a front view of the bone anchor assembly of FIG. 16A;

FIG. 16E is a detail view of the portion of the bone anchor assembly of FIG. 16A shown in circle B in FIG. 16C;

FIG. 17 is a detail view of a portion of another embodiment of a bone anchor assembly;

FIG. 18 is a detail view of a portion of another embodiment of a bone anchor assembly;

FIG. 19A is a perspective view of another embodiment of a retaining ring or insert;

FIG. 19B is a side view of the retaining ring or insert of FIG. 19A;

FIG. 19C is a bottom view of the retaining ring or insert of FIG. 19A;

FIG. 19D is a top view of the retaining ring or insert of FIG. 19A; and

FIG. 19E is a cross-sectional view of the retaining ring or insert of FIG. 19A taken along the ling H-H in FIG. 19D.

DETAILED DESCRIPTION

Figure 1A:
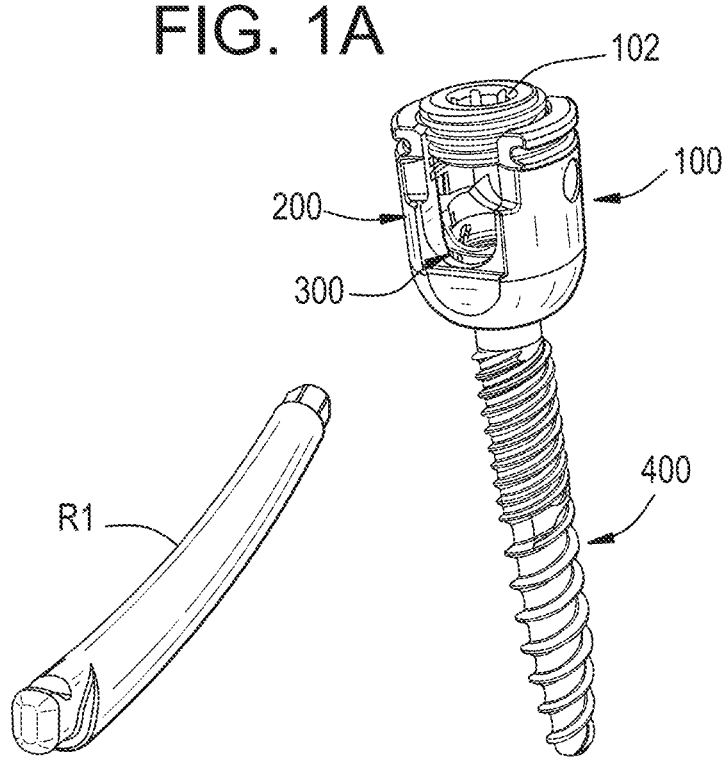
FIG. 1A is a perspective view of a bone anchor assembly and a spinal rod.
Figure 1B:
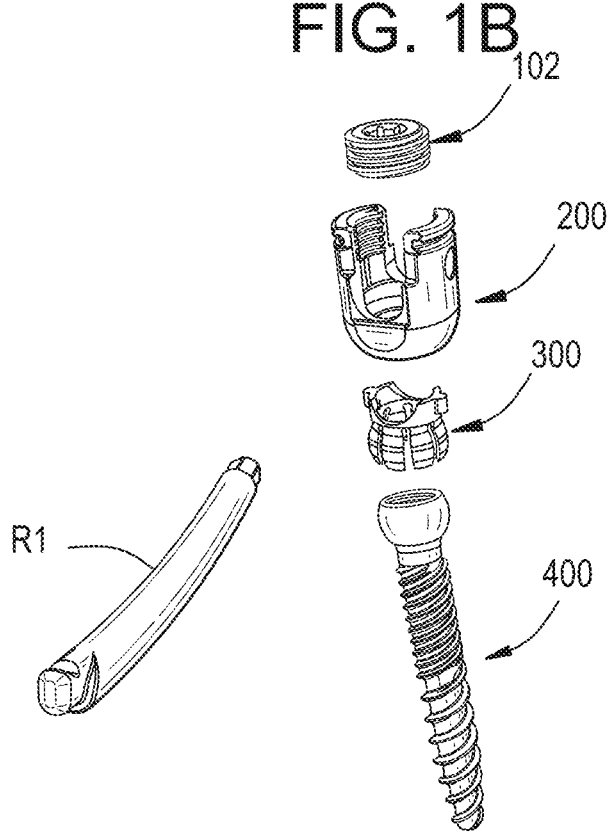
FIG. 1B is an exploded perspective view of the bone anchor assembly of FIG. 1A.
Figure 1C:
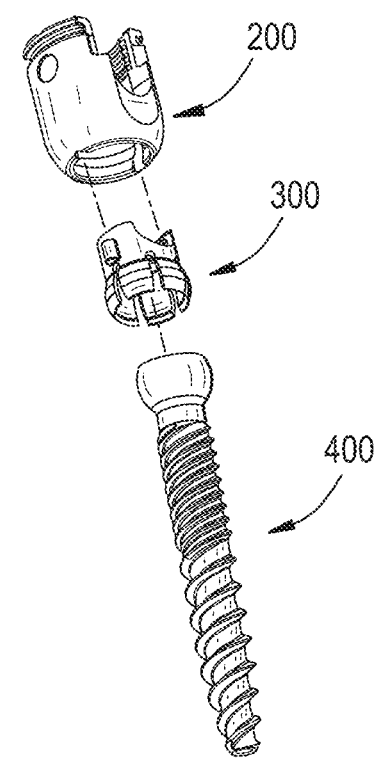
FIG. 1C is another exploded perspective view of the bone anchor assembly of FIG. 1A.

Bone anchor assemblies and related instrumentation are disclosed herein. In some embodiments, a modular bone anchor assembly allows for a bone anchor to be driven into bone and a head or receiver member to be attached thereto at some later point in time. The bone anchor can have a smaller footprint than the complete assembly, which can improve visualization and anatomical spatial awareness during insertion of the bone anchor and during other surgical steps performed prior to attaching the head or receiver member to the bone anchor. A variety of modular head types are disclosed, as are various instruments for driving a bone anchor, attaching a head to a bone anchor, removing a head from a bone anchor, and making a unilateral attachment to a head of a bone anchor assembly. Drive interfaces for driving a bone anchor are disclosed, as are features that allow a bone anchor to act as a fixation point for soft tissue retraction, disc space distraction, derotation, and the like.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Bone Anchor Assemblies

FIGS. 1A-1H illustrate an exemplary embodiment of a bone anchor assembly 100. As shown, the assembly 100 can include a head or receiver member 200, a collet 300, a shank or bone anchor 400, and a closure mechanism or set screw 102. The bone anchor assembly 100 can be modular such that any of a variety of heads 200 can be coupled to any of a variety of bone anchors 400, and such that the assembly 100 can be fit together in situ. The bone anchor 400 can be bottom loaded into the receiver member 200 and can be captured by the collet 300 to retain the bone anchor within the receiver member while still allowing relative motion therebetween. The set screw 102 can be tightened to wedge the collet 300 between the head of the bone anchor 400 and the receiver member 200, thereby locking the relative position of the bone anchor and the receiver member. The set screw 102 can also be effective to lock a spinal rod R1 or other implant to the bone anchor assembly 100.

In use, the bone anchor 400 can be driven into bone without the head 200 being attached thereto. This can result in a lower profile initial construct and allow the bone anchor 400 to be placed before other steps of the procedure are performed, such as exposing the neural elements, removing the facets and disc for fusion, and so forth. As a result, anatomical reference points can be preserved and can be used when targeting bone anchor 400 insertion. Also, the lower profile can provide more access to the surgical site for the user. The bone anchor 400 can also be used as a platform for other manipulations, such as distraction, compression, derotation, soft tissue retraction, and the like. The assembly 100 can also be implanted in the patient in a pre-assembled state.

FIGS. 2A-2J illustrate the head or receiver member 200 in detail. The receiver member 200 can include proximal and distal ends 200p, 200d that define a central proximal-distal axis A1. The proximal end 200p of the receiver member 200 can include a pair of spaced apart arms 202, 204 that define a rod-receiving recess 206 therebetween. The rod-receiving recess 206 can have a central axis A2. The rod-receiving recess 206 can be open in a proximal direction, such that a rod R1 can be inserted into the recess by moving the rod distally with respect to the receiver member 200. The inner surfaces of each of the arms 202, 204 can be configured to mate with the set screw 102. For example, the inner surfaces of the arms 202, 204 can include threads that correspond to external threads formed on the set screw 102. Accordingly, rotation of the set screw 102 with respect to the receiver member 200 about the axis A1 can be effective to translate the set screw with respect to the receiver member axially along the axis A1. Each of the arms 202, 204 can extend from a base portion 208 of the receiver member 200 to a free end.

The arms 202, 204 can include features, such as recesses, dimples, notches, projections, or the like, to facilitate coupling of the receiver member 200 to various instruments.

For example, the outer surface of each arm 202, 204 can include a groove or channel 210 formed therein to define a "top notch" feature. In the illustrated embodiment, each arm 202, 204 includes an arcuate groove 210 formed in the exterior surface of the arm adjacent the free end of the arm. As described further below, the groove 210 can be engaged with a corresponding projection of an instrument to facilitate coupling of the instrument to the receiver member 200.

Figure 2A:
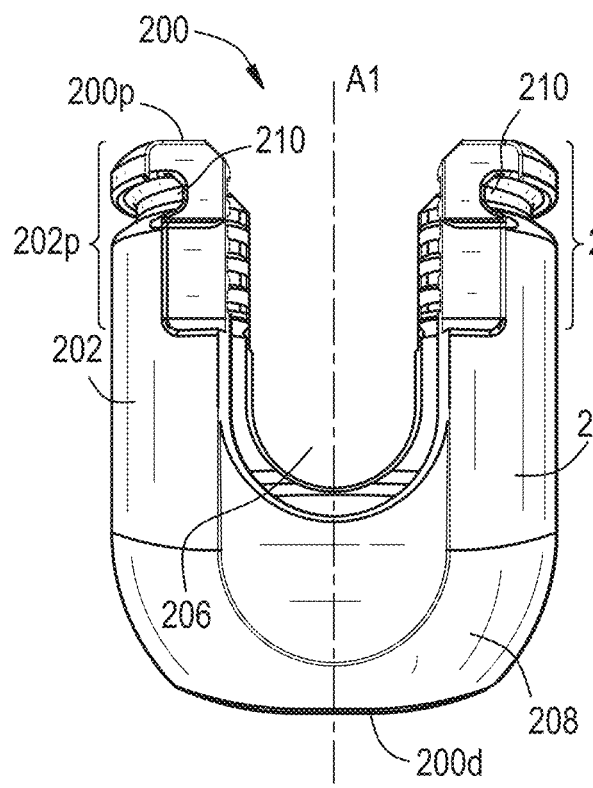
FIG. 2A is a front view of the receiver member of the bone anchor assembly of FIG. 1A.
Figure 2B:
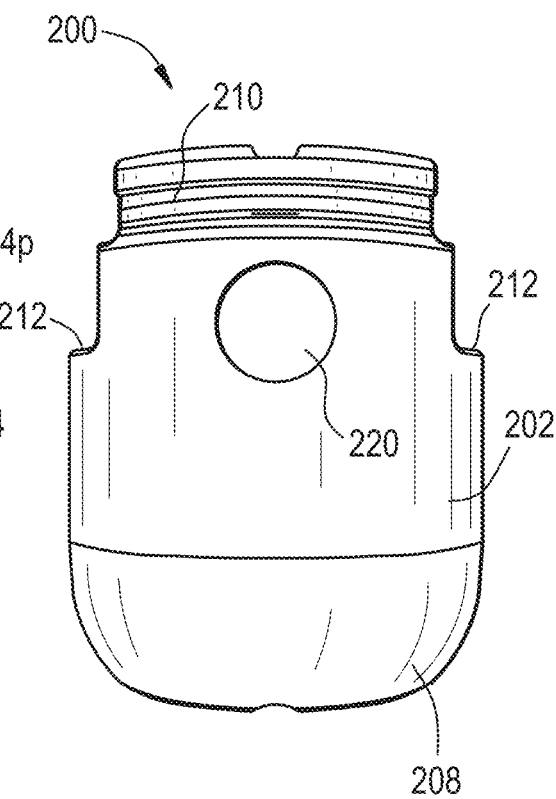
FIG. 2B is a side view of the receiver member of FIG. 2A.
Figure 2C:
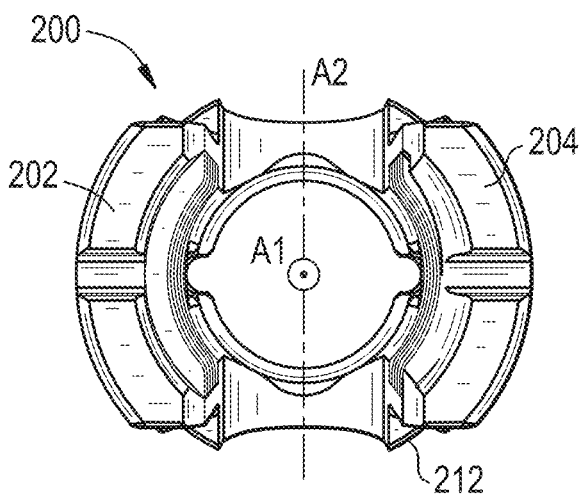
FIG. 2C is a top view of the receiver member of FIG. 2A.
Figure 2D:
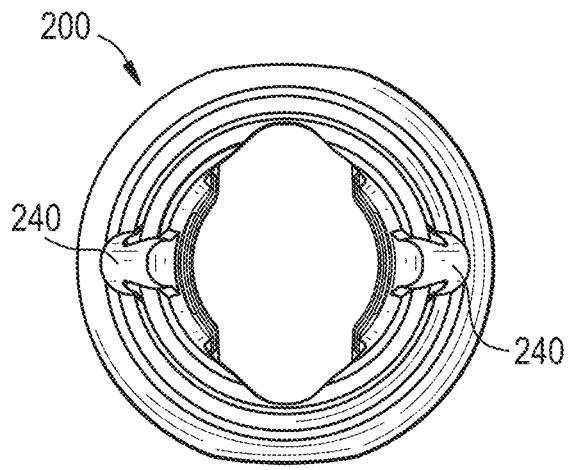
FIG. 2D is a bottom view of the receiver member of FIG. 2A.
Figure 2E:
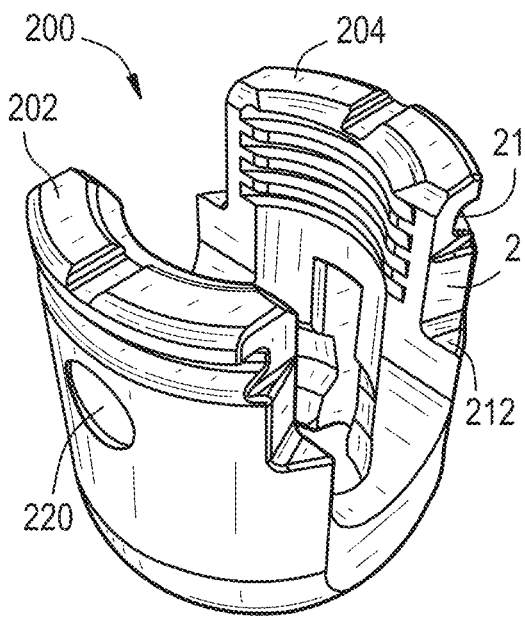
FIG. 2E is a perspective top view of the receiver member of FIG. 2A.
Figure 2F:
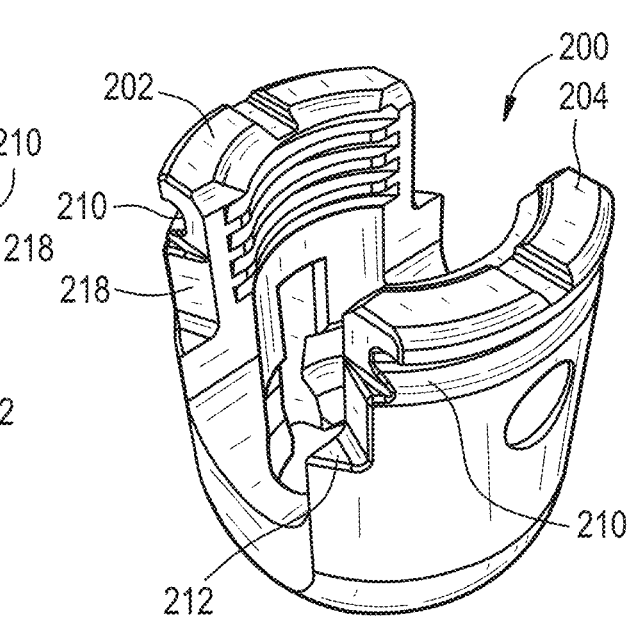
FIG. 2F is another perspective top view of the receiver member of FIG. 2A.
Figure 2G:
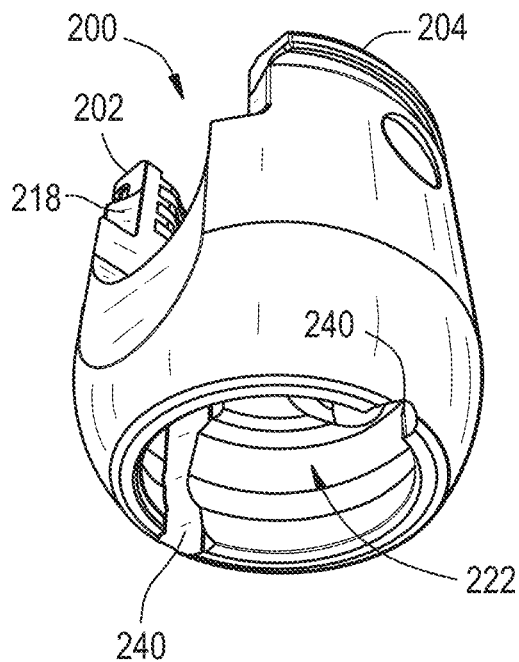
FIG. 2G is a perspective bottom view of the receiver member of FIG. 2A.
Figure 2H:
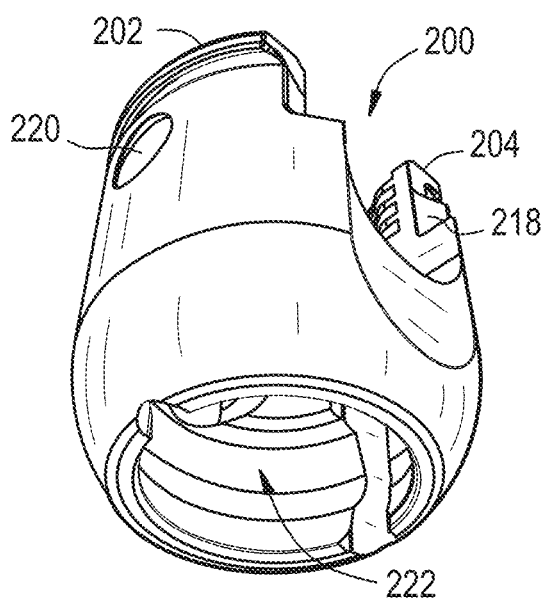
FIG. 2H is another perspective bottom view of the receiver member of FIG. 2A.
Figure 2I:
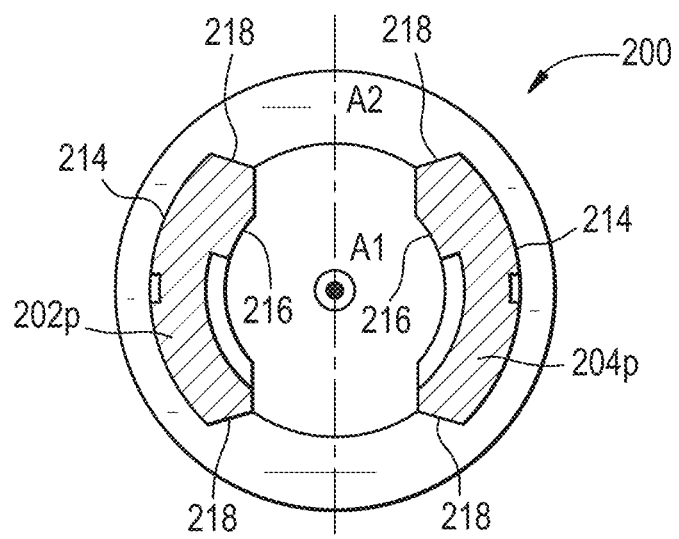
FIG. 2I is a sectional top view of the receiver member of FIG. 2A.

By way of further example, the receiver member 200 can include a unilateral instrument attachment feature. In other words, the receiver member 200 can include a feature that allows rigid attachment of an instrument thereto by engaging only one arm 202, 204 of the receiver member. An exemplary unilateral attachment feature is shown, in which at least a portion of each arm 202, 204 has a cross-section that facilitates a dovetail unilateral mating with an attachment instrument, e.g., an instrument of the type described below with respect to FIGS. 12A-12F. Proximal portions 202p, 204p of the arms 202, 204 can be narrowed at a stepped-in ledge 212. As shown in FIG. 2I, the proximal portion 202p, 204p of each arm 202, 204 can have a cross-section defined by a generally curved outer surface 214, a generally curved inner surface 216, and first and second planar dovetail engagement surfaces 218 extending between the inner and outer surfaces. The first and second engagement surfaces 218 can extend at an oblique angle with respect to a plane defined by the central proximal-distal axis A1 of the receiver member and the central axis A2 of the rod-receiving recess 206. The first and second engagement surfaces 218 of each arm can be angled towards each other as the surfaces approach the central proximal-distal axis A1 of the receiver member 200. As described further below, the geometry of the cross-section of each arm 202, 204 can allow the arm to be received within a recess of a unilateral attachment instrument to restrict movement of the arm and the receiver member 200 relative to the instrument.

As another example, the arms 202, 204 can each include a blind hole, through hole, recess, or opening 220 formed in an exterior sidewall thereof. The blind hole 220 can be engaged with a corresponding projection of an instrument, such as a rocker fork reduction instrument, to facilitate coupling of the instrument to the receiver member 200.

Figure 2J:
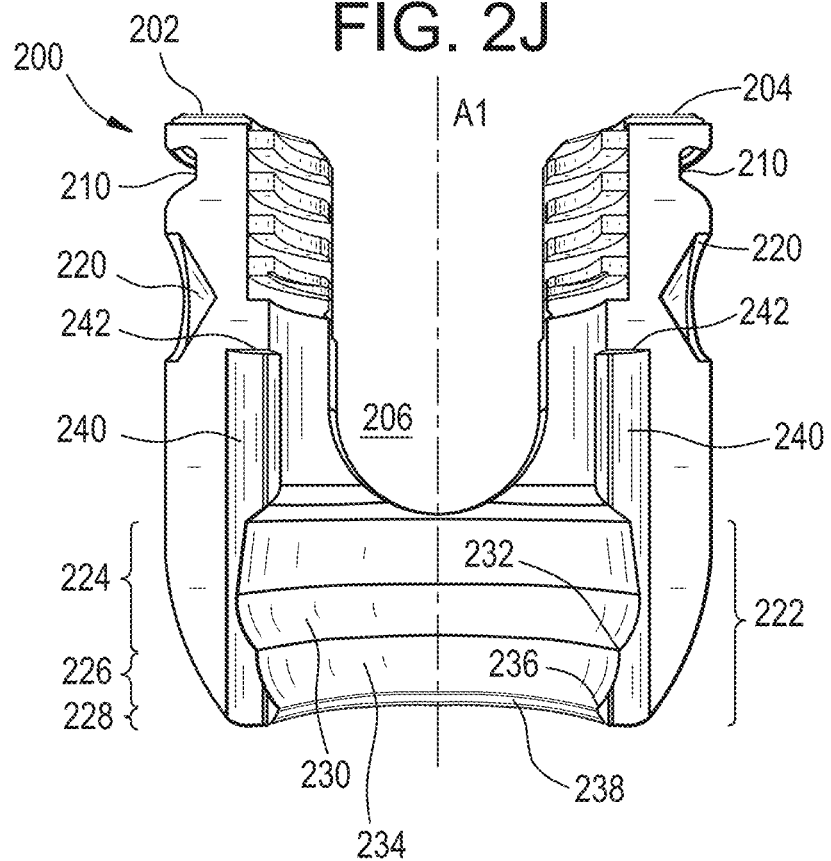
FIG. 2J is a sectional front view of the receiver member of FIG. 2A.

The base portion 208 of the receiver member 200 can define an interior cavity 222 in which the collet 300 and the head of the bone anchor 400 can be received. While any of a variety of cavity shapes can be used, the illustrated cavity 222 includes an upper, proximal portion 224, a middle portion 226, and a lower, distal portion 228, as shown in FIG. 2J.

The upper portion 224 of the cavity 222 can be frustoconical or substantially frustoconical about the axis A1, with a spherical or substantially spherical seat 230 that faces in a proximal direction. A first shelf 232 that projects radially-inward into the cavity 222 can be defined at the transition between the upper and middle portions 224, 226 of the cavity. The middle portion 226 of the cavity 222 can define a spherical or substantially spherical seat 234 that faces in a proximal direction. In some embodiments, the seat 234 can be conical and/or tapered. The radius of the spherical seat 234 of the middle portion 226 of the cavity 222 can be less than the radius of the spherical seat 230 of the upper portion 224 of the cavity. A second shelf 236 that projects radially-inward into the cavity 222 can be defined at the transition between the middle and lower portions 226, 228 of the cavity. The lower portion 228 of the cavity 222 can define a conical or spherical seat 238 that faces in a distal direction.

In some embodiments, the cavity 222 can be entirely defined by interior surfaces of a unitary or monolithic receiver member 200. In some embodiments, for example as described below with respect to FIGS. 13A-13F and FIGS. 13G-13K, at least a portion of the cavity can be defined by a retaining ring or insert that is separate from the receiver member.

The receiver member 200 can include features for restricting or preventing motion of the collet 300 with respect to the receiver member. For example, the receiver member 200 can include features for limiting proximal-distal travel of the collet 300, or for limiting or preventing rotation of the collet. In the illustrated embodiment, the receiver member 200 includes diametrically-opposed keyways 240 sized to receive wings of the collet 300 therein. The keyways 240 can be formed in the cavity 222 and can extend into the arms 202, 204. The wings of the collet 300 can be slidably received in the keyways 240 to allow the collet to translate along the axis A1 with respect to the receiver member 200 while restricting or preventing rotation of the collet about the axis A1 with respect to the receiver member. Proximal travel of the collet 300 within the receiver member 200 can be limited by engagement between a proximal-facing surface of the collet wings and a distal-facing shoulder 242 formed at the roof of the keyways 240. While multiple keyways 240 are shown, the receiver member 200 can include only a single keyway in some embodiments or can include more than two keyways.

FIGS. 3A-3K illustrate the collet 300 in detail. The collet 300 can be positioned within the cavity 222 formed in the receiver member 200. The collet 300 can be sized such that it is longitudinally translatable within the cavity 222, along the axis A1. The collet 300 can be generally cylindrical with first and second arms 302, 304 extending in a proximal direction to respective free ends of the arms. The first and second arms 302, 304 can be aligned with the first and second arms 202, 204 of the receiver member 200 such that a recess 306 defined therebetween is aligned with the rod-receiving recess 206. Accordingly, the rod R1 can be simultaneously cradled between the arms 302, 304 of the collet 300 and the arms 202, 204 of the receiver member 200 when the rod is disposed in the rod-receiving recess 206.

The collet 300 can include a mating feature configured to limit or prevent certain movement of the collet with respect to the receiver member 200. For example, the collet 300 can include opposed wings or projections 308 that extend radially-outward from an exterior surface of the collet. The wings 308 can be received within the keyways 240 described above to allow the collet 300 to translate within the receiver member 200 but to limit proximal travel of the collet and limit or prevent rotation of the collet relative to the receiver member. It will be appreciated that the keyways 240 can alternatively be formed in the collet 300 and the projections 308 formed in the cavity 222 of the receiver member 200. While multiple wings 308 are shown, the collet 300 can include only a single wing in some embodiments or can include more than two wings.

The collet 300 can define a central opening 310 that extends completely through the collet along the axis A1. The opening 310 can be sized to receive a guide wire or needle therethrough, or to receive a driver therethrough for engaging the drive interface of the bone anchor 400.

Figure 3A:
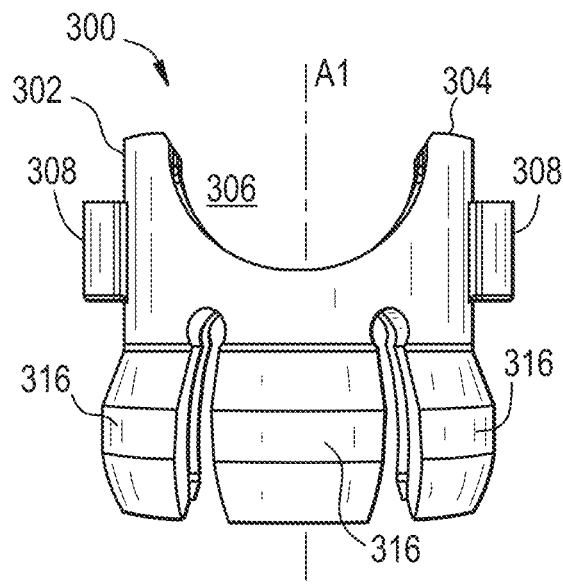
FIG. 3A is a front view of the collet of the bone anchor assembly of FIG. 1A.
Figure 3B:
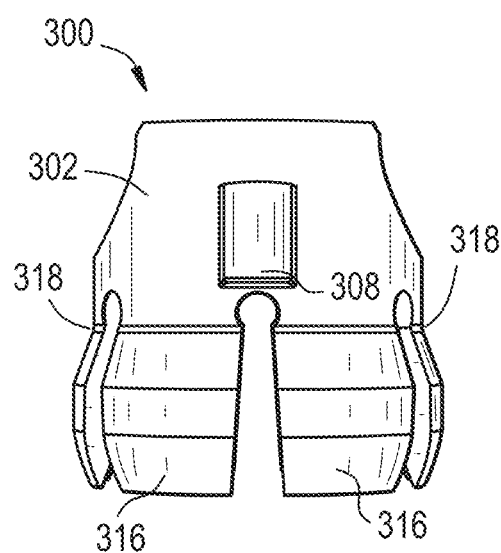
FIG. 3B is a side view of the collet of FIG. 3A.
Figure 3C:
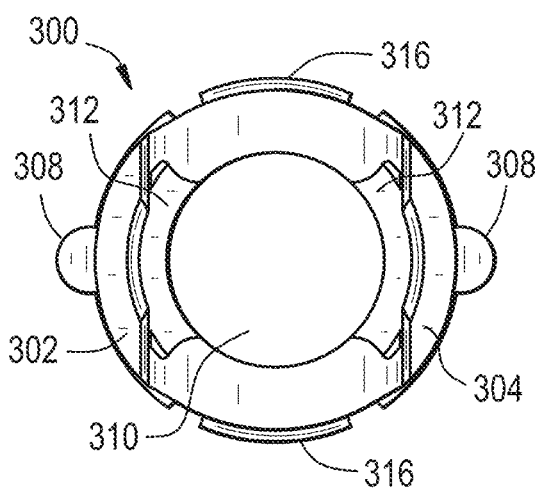
FIG. 3C is a top view of the collet of FIG. 3A.
Figure 3D:
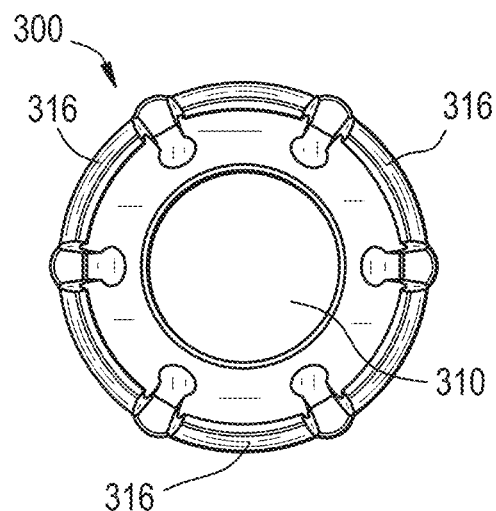
FIG. 3D is a bottom view of the collet of FIG. 3A.
Figure 3E:
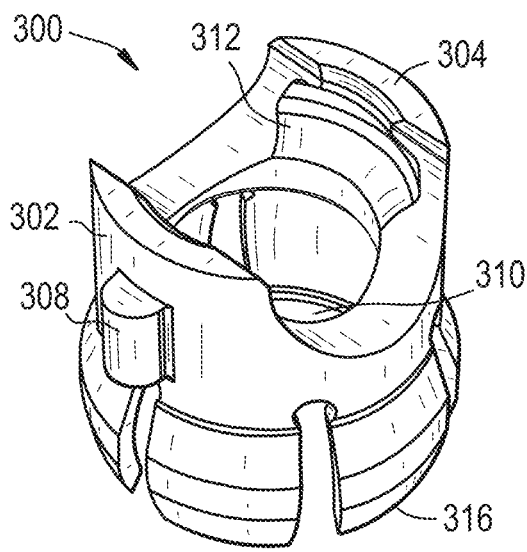
FIG. 3E is a perspective top view of the collet of FIG. 3A.
Figure 3F:
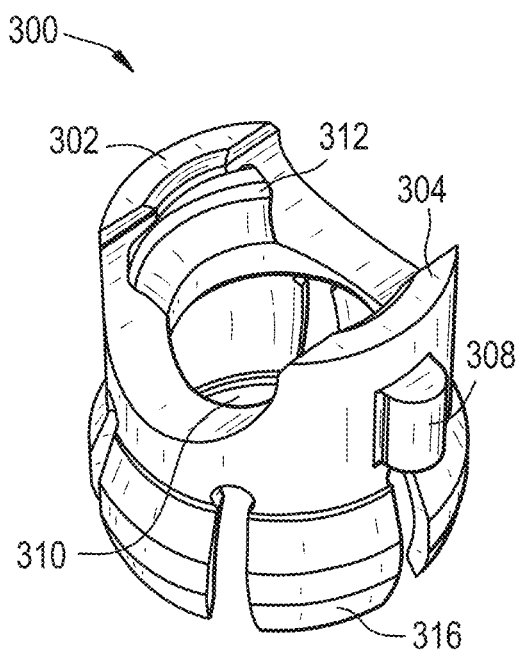
FIG. 3F is another perspective top view of the collet of FIG. 3A.
Figure 3G:
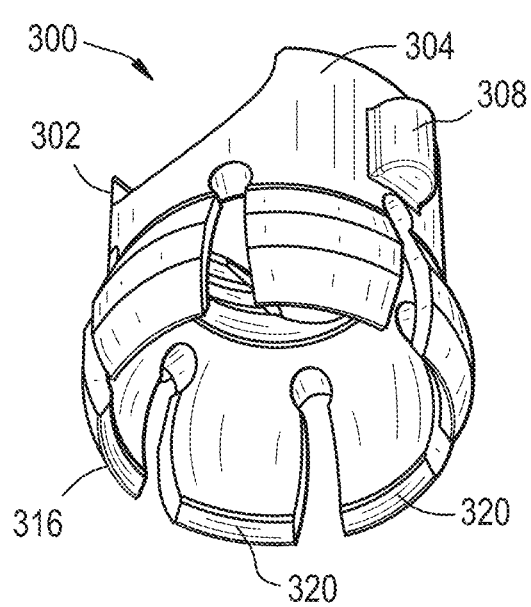
FIG. 3G is a perspective bottom view of the collet of FIG. 3A.
Figure 3H:
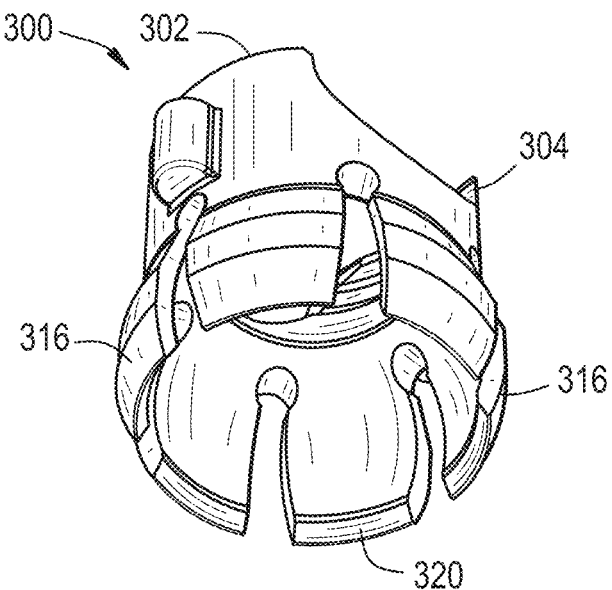
FIG. 3H is another perspective bottom view of the collet of FIG. 3A.
Figure 3I:
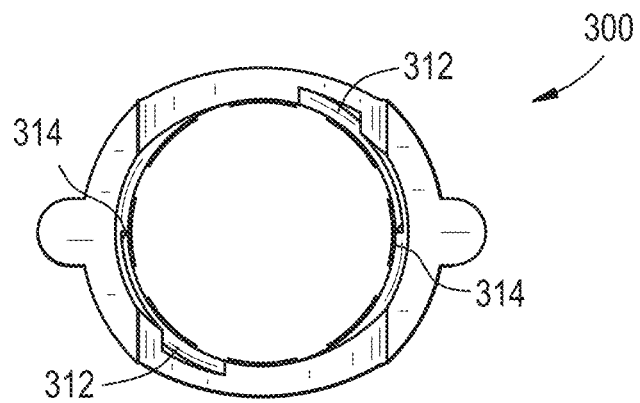
FIG. 3I is a top view of the collet of FIG. 3A shown with an alternative recess shape.
Figure 3J:
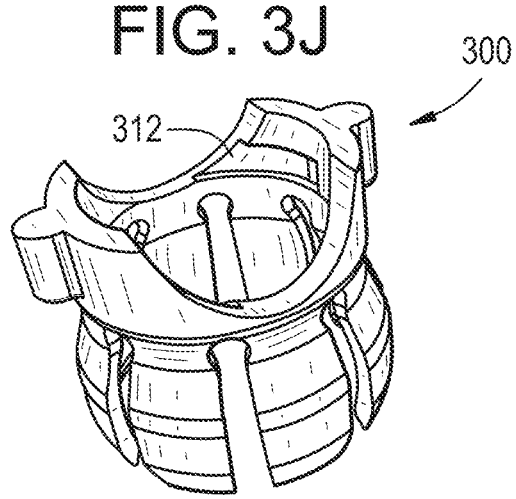
FIG. 3J is a perspective top view of the collet of FIG. 3I.
Figure 3K:
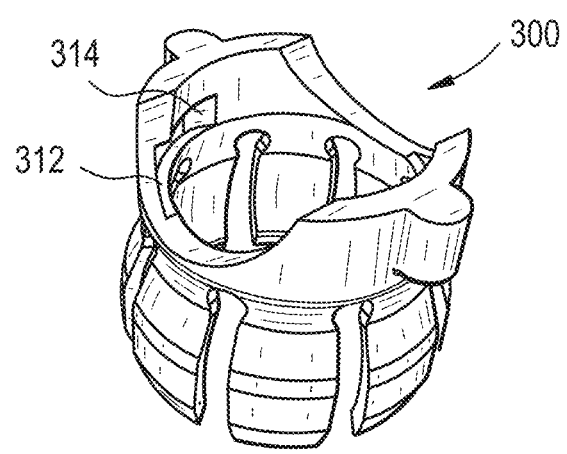
FIG. 3K is another perspective top view of the collet of FIG. 3I.

The collet 300 can include features for engaging the collet with an instrument to manipulate the collet, e.g., during insertion or removal of the collet from the receiver member 200. For example, the arms 302, 304 of the collet 300 can each include a respective recess 312. The recess 312 can be engaged with an instrument for removing the collet 300 and receiver member 200 from a bone anchor 400, or for assembling the collet to the receiver member, as explained below with respect to FIG. 10. The recess 312 can be open to both lateral ends of the arms 302, 304, as shown in FIGS. 3A-3H, or can be open to only one lateral end of the arms, as shown in FIGS. 3I-3K. In the latter configuration, the recess 312 can include a proximal-facing surface, a distal-facing surface, a radially-inward facing surface, and an abutment surface 314 that connects the proximal-facing, distal-facing, and inward-facing surfaces. The abutment surface 314 can be configured to abut with a bearing surface of an instrument, as described below.

The collet 300 can include one or more slits formed therein to define a plurality of distally-extending fingers 316. The fingers 316 can be configured to deform radially-inward and/or radially-outward from a resting position. The fingers 316 can have resilient properties such that, when deformed from their resting position, the fingers are biased towards the resting position.

While the illustrated collet 300 includes six fingers 316, it will be appreciated that the collet can include any number of fingers, e.g., zero, one, two, three, four, five, six, seven, eight, or more. Including a larger number of fingers 316 can result in each individual finger being narrower in width for a given size collet 300, making the finger easier to deflect during assembly.

The slits can have an expanded or T-shaped proximal end to provide a relief and allow the fingers 316 to deform to a greater degree with less effort or without breaking. The fingers 316 can include a reduced-thickness region 318 adjacent their proximal end to encourage bending of the fingers at a predetermined bend zone. The distal-most ends of the fingers 316 can include a curved, tapered, angled, or ramped surface 320 to provide a lead in for entry of the head of the bone anchor 400 and for wedging the collet fingers between the head of the bone anchor and the receiver member 200. The lead-in surface 320 can face substantially radially-inward. The inner surfaces of the fingers 316 can be spherical or substantially spherical. The outer surfaces of the fingers 316 can likewise be spherical or substantially spherical. In some embodiments, the inner surfaces of the fingers 316 each form sections of a common sphere.

In use, the fingers 316 can be deformed from their resting position as the collet 300 is loaded into the distal end of the cavity 222. In particular, the second shelf 236 of the cavity 222 can bear against the exterior surfaces of the fingers 316 to deform the fingers radially-inward from their resting position. Once the collet 300 is advanced far enough in the proximal direction, the fingers 316 can pass the second shelf 236 and expand radially-outward within the upper proximal portion 224 and/or middle portion 226 of the cavity 222. The expanded fingers 316 can have a diameter greater than that of the opening defined by the second shelf 236, such that the collet 300 is retained in the cavity 222. It will be appreciated that the ability to deform and expand the collet 300 within the receiver member 200 can allow the collet to be retained within the cavity 222 without necessarily requiring swaging. Swaging is a common manufacturing process that involves permanent material deformation to retain one component within another. Deformation of material during the swaging process is less predictable than traditional machining processes and can require special manufacturing controls, which can increase manufacturing cost. The illustrated bone anchor assembly 100 can thus be easier and less expensive to manufacture than bone anchor assemblies that require swaging. While swaging is not necessarily required, in some embodiments, swaging can be used to retain the collet 300 within the cavity 222 or to augment the retention of the collet.

The fingers 316 can also be deformed from their resting position as the head of the shank 400 is loaded into the distal end of the collet 300. The receiver member 200 and the collet 300 can be assembled to the head of the shank 400 by applying a distal axial force to the receiver member over the head of the shank. The head of the shank 400 can bear against the distal lead-in surfaces 320 of the fingers 316 to deform the fingers radially-outward from their resting position. Once the head of the shank 400 is advanced far enough into the collet 300, the fingers 316 can return towards their resting position, capturing the head of the shank therein to retain the shank within the collet and, by extension, within the receiver member 200. When captured within the collet 300, and before the collet is locked down within the receiver member 200, the shank 400 can still be free to pivot with respect to the collet and to rotate about the axis A1 relative to the collet. The collet 300 can apply a drag force to the head of the bone anchor 400, e.g., due to a light interference fit between the collet fingers 316 and the head of the bone anchor. The drag force can maintain the relative position between the receiver member 200 and the bone anchor 400 prior to locking the construct, e.g., during provisional positioning of the assembly 100, to prevent the receiver member from "flopping" over. The drag force can thus prevent unintended movement prior to locking the assembly 100, while still allowing free movement when intended by the user.

Once assembled to the head of the shank 400, rod insertion and set screw 102 locking can be effective to drive the collet 300 distally with respect to the receiver member 200, wedging the collet fingers 316 between the head of the shank and the interior of the middle portion 226 of the cavity 222, thereby locking movement of the shank with respect to the receiver member.

In some embodiments, the collet 300 can include a compression cap component and a collet ring component, for example as described below with respect to FIGS. 14A-14K.

The set screw 102 can include an exterior thread configured to mate with the interior threads formed on the arms 202, 204 of the receiver member 200. The threaded engagement can allow the set screw 102 to be advanced or retracted along the axis A1 with respect to the receiver member 200 by rotating the set screw about the axis A1. The set screw 102 can include a driving interface configured to receive a driver for applying a rotational force to the set screw about the axis A1. The distal surface of the set screw 102 can be configured to contact and bear against a rod R1 disposed in the rod-receiving recess 206 to lock the rod to the assembly 100. When tightened against the rod R1, the set screw 102 can prevent the rod from translating relative to the receiver member 200 along the axis A2 and/or from rotating with respect to the receiver member about the axis A2. While a set screw 102 is shown, it will be appreciated that other locking elements can be used instead or addition, such as a closure cap that advances and locks by quarter-turn rotation, a closure cap that slides in laterally without rotating, a nut that threads onto an exterior of the receiver member 200, and so forth. In some embodiments, a dual set screw can be used. The dual set screw can include an outer set screw that bears against the arms 302, 304 of the collet 300 to lock the polyaxial movement of the shank 400 relative to the receiver member 200. The dual set screw can also include an inner set screw threadably mounted in an opening formed in the outer set screw. The inner set screw can be tightened to bear against the rod R1 and to lock the rod to the receiver member 200.

FIGS. 4A-4K illustrate the shank or bone anchor 400 in detail. The bone anchor 400 can include a proximal head portion 402 and a distal shaft portion 404 and can define a central longitudinal bone anchor axis A3.

The distal shaft 404 of the bone anchor 400 can be configured to engage bone and, in the illustrated embodiment, includes an external bone engaging thread 406. The thread form for the distal shaft 404, including the number of threads, the pitch, the major and minor diameters, and the thread shape, can be selected to facilitate connection with bone. The illustrated thread form 406 is a cortical fix thread that transitions from a double lead thread to a quadruple lead thread. Such a thread form can advantageously increase displacement in the pedicle canal. Other exemplary thread forms are disclosed in U.S. Patent Application Publication No. 2011/0288599, filed on May 18, 2011, and in U.S. Patent Application Publication No. 2013/0053901, filed on Aug. 22, 2012, both of which are hereby incorporated by reference herein. The distal shaft 404 can also include other structures for engaging bone, including a hook. The distal shaft 404 can be cannulated, having a central passage or cannula 408 extending the length of the bone anchor 400 to facilitate delivery of the bone anchor over a guidewire in, for example, minimally-invasive procedures. Other components of the bone anchor assembly 100, including, for example, the set screw 102, the collet 300, and the receiver member 200 can be cannulated or otherwise have an opening to permit delivery over a guidewire. The distal shaft 404 can also include one or more sidewall openings or fenestrations (not shown) that communicate with the cannula 408 to permit bone in-growth or to permit the dispensing of bone cement or other materials through the bone anchor 400. The sidewall openings can extend radially from the cannula 408 through the sidewall of the distal shaft 404. Exemplary systems for delivering bone cement to the bone anchor assembly 100 and alternative bone anchor configurations for facilitating cement delivery are described in U.S. Patent Application Publication No. 2010/0114174, filed on Oct. 29, 2009, which is hereby incorporated by reference herein. The distal shaft 404 of the bone anchor 400 can be coated with materials to permit bone growth, such as, for example, hydroxyapatite, and the bone anchor assembly 100 can be coated partially or entirely with anti-infective materials, such as, for example, tryclosan.

The proximal head portion 402 of the bone anchor 400 can be generally in the shape of a truncated sphere having a planar proximal surface and an approximately spherically-shaped distal surface. The illustrated bone anchor assembly 100 is a polyaxial bone screw designed for posterior implantation in the pedicle or lateral mass of a vertebra, anterolateral fixation, and/or other indications. The proximal head 402 of the bone anchor 400 can engage the interior of the collet fingers 316 in a ball and socket like arrangement in which the proximal head 402 and the distal shaft 404 can pivot relative to the collet 300 and the receiver member 200.

The head portion 402 of the bone anchor 400 can include a drive interface for applying torque to the bone anchor, e.g., to drive the bone anchor into bone or to withdraw or retract the bone anchor from bone. The drive interface can also be used to attach various instruments to the bone anchor 400, e.g., to allow the bone anchor to serve as a platform for distraction, compression, derotation, soft tissue retraction, and the like.

As shown in FIGS. 4A-4E, the drive interface can include a proximal cavity 410 and a distal cavity 412. The proximal cavity 410 can be substantially cylindrical with an internal thread formed therein for engaging a corresponding threaded portion of an instrument. The distal cavity 412 can be shaped to non-rotatably engage the bone anchor 400 with a drive tip of a driver instrument. While a hexalobe star drive interface is shown for the distal cavity 412, it will be appreciated that other interfaces can be used instead or in addition, including slotted, Phillips, square socket, hex socket, pentalobe, and the like. The threaded proximal cavity 410 can allow for rigid instrument connection to the bone anchor 400. For example, a threaded outer countertorque tube can be rigidly connected to the threaded interface 410, and a driver shaft can be inserted therethrough to apply torque to the bone anchor 400 via the distal cavity 412. As another example, the threaded section 410 can allow for connection to the driver shaft itself, e.g., in the case of a driver shaft having a drive interface in the form of a threaded distal end. The threaded section 410 can also allow for rigid connection to an extension tube or shaft for performing distraction, compression, derotation, retraction, or other manipulations. The illustrated drive interface can allow a threaded cylindrical driver tool or a standard hexalobe driver tool to be used interchangeably. The ability to use different driver instruments with the same bone anchor 400 can be desirable as it can allow the bone anchor to be driven with a standard driver instrument if a specialized driver instrument is not available (e.g., as may be the case in a revision surgery in which the original, specialized driver instrument is not available).

Figure 4F:
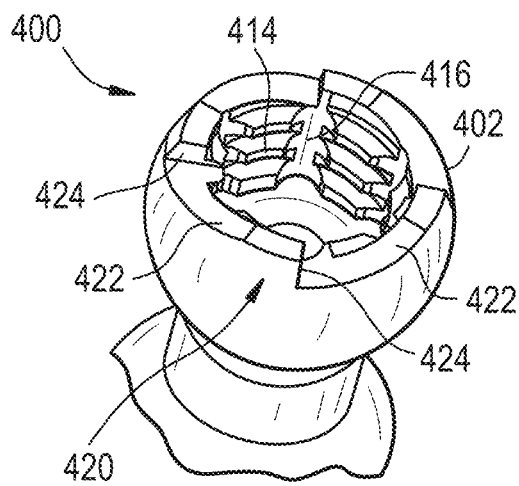
FIG. 4F is a perspective top view of the bone anchor of FIG. 4A, shown with an alternative drive feature.
Figure 4G:
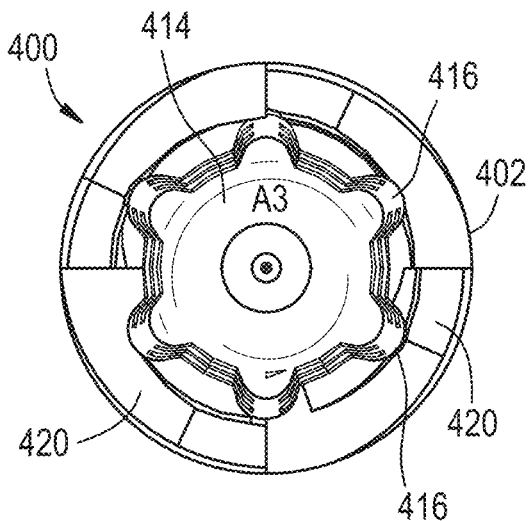
FIG. 4G is a top view of the bone anchor of FIG. 4F.

FIGS. 4F-4G illustrate an alternative drive interface. As shown, the drive interface can include a substantially cylindrical cavity 414 with an internal thread formed therein for engaging a corresponding threaded portion of a driver instrument. The thread can be interrupted by a series of longitudinal channels 416, such that the channels and the inner-most surface of the thread define a hexalobe drive interface. This can allow a threaded cylindrical driver tool or a standard hexalobe driver tool to be used interchangeably. Because the threaded and hexalobe drive features overlap one another, the height profile of the bone anchor 400 can be reduced, and/or the engaged height of the driver instrument can be increased. The proximal-facing surface of the head 402 of the bone anchor 400 can include countertorque features. As described further below with respect to FIGS. 7A-7G, these features can allow the bone anchor 400 to be engaged with a countertorque sleeve. The illustrated features include a plurality of ramped projections 420 that extend proximally from the proximal-facing surface of the head. Each projection 420 can include a ramped surface 422 that extends obliquely from a plane transverse to the axis A3 and an abutment surface 424 that extends parallel to the axis A3. The abutment surfaces 424 can provide unidirectional countertorque engagement.

Figure 4H:
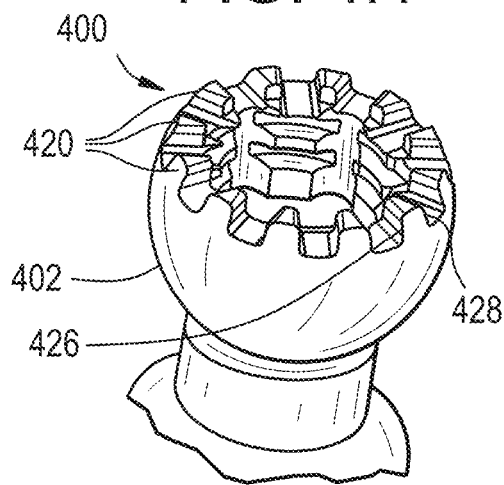
FIG. 4H is a perspective top view of the bone anchor of FIG. 4A, shown with an alternative drive feature.
Figure 4I:
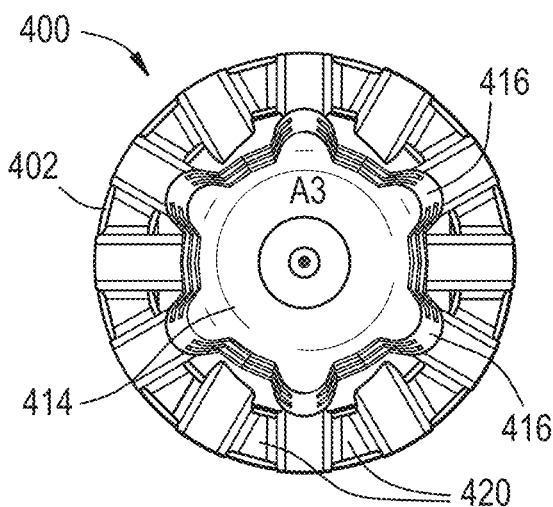
FIG. 4I is a top view of the bone anchor of FIG. 4H.

FIGS. 4H-4I illustrate an alternative drive interface. As shown, the drive interface can include a substantially cylindrical cavity 414 with an internal thread formed therein for engaging a corresponding threaded portion of a driver instrument. The thread can be interrupted by a series of longitudinal channels 416, such that the channels and the inner-most surface of the thread define a hexalobe drive interface. This can allow a threaded cylindrical driver tool or a standard hexalobe driver tool to be used interchangeably. Because the threaded and hexalobe drive features overlap one another, the height profile of the bone anchor 400 can be reduced, and/or the engaged height of the driver instrument can be increased. The proximal-facing surface of the head 402 of the bone anchor 400 can include countertorque features. As described further below with respect to FIGS. 8A-8F, these features can allow the bone anchor 400 to be engaged with a countertorque sleeve. The illustrated features form a "castle" pattern defined by a plurality of projections 420 that extend proximally from the proximal-facing surface of the head 402. Each projection 420 can include a first abutment surface 426 that extends parallel to the axis A3 and a second abutment surface 428 that extends parallel to the axis A3. The abutment surfaces 426, 428 can provide bidirectional countertorque engagement.

The drive interfaces of FIGS. 4F-4G and FIGS. 4H-4I can include a fully-threaded interior. In other words, the threaded portion of the drive interface can extend substantially the entire depth of the drive recess. This can allow for deeper thread engagement, providing a stronger connection between the bone anchor 400 and a driver or other instrument. The threaded driver attachment can also allow for the driver shaft to be made stronger as compared to a driver shaft inserted through a threaded outer tube, since the driver shaft can just be a large diameter threaded shaft that is completely solid or solid except for a small-diameter guidewire cannulation. By increasing the strength of the driver shaft, the same instrument can be used for other tasks like compression, distraction, etc. While a hexalobe feature is shown cut into the threaded interface, it will be appreciated that this can be omitted and the interface can include a continuous, uninterrupted thread, or other types of features can be cut into the threaded interface.

Figure 4J:
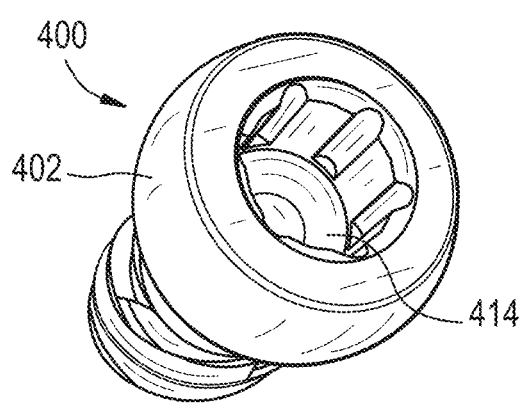
FIG. 4J is a perspective top view of the bone anchor of FIG. 4A, shown with an alternative drive feature.
Figure 4K:
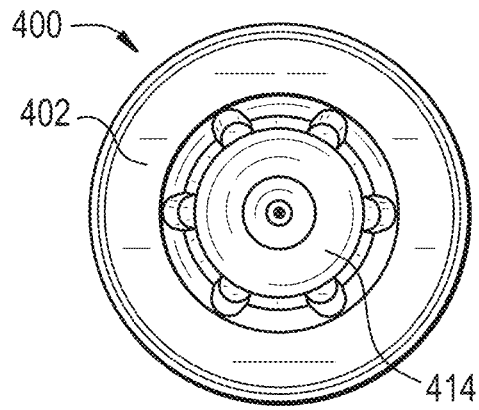
FIG. 4K is a top view of the bone anchor of FIG. 4J.

FIGS. 4J-4K illustrate an alternative drive interface. As shown, the threaded engagement can be omitted and the drive interface can be a simple hexalobe recess 414 or other standard drive type.

Referring again to FIGS. 1D-1H, an exemplary method of using the bone anchor assembly 100 is described below. The bone anchor assembly 100 can be provided for a surgery in a state of partial disassembly. For example, the bone anchor 400 can be initially separated from the receiver member 200 and the collet 300. The receiver member 200 and the collet 300 can be preassembled or can be assembled by the user during the surgery.

The bone anchor 400 can be delivered to a target bone site within the patient and driven to a desired depth along a desired trajectory using known techniques. The bone anchor 400 can be driven into the bone before or after attaching the receiver member 200 and the collet 300 to the bone anchor. When the bone anchor 400 is driven into the bone before attaching the collet 300 and the receiver member 200, the initial construct can have a lower profile that can allow the bone anchor to be placed before other steps of the procedure are performed, such as exposing the neural elements, removing the facets and disc for fusion, and so forth. As a result, anatomical reference points can be preserved and can be used when targeting bone anchor insertion. Also, the lower profile can provide more access to the surgical site for the user. The bone anchor 400 can be driven using driver instruments of the type described herein, including the instrument 700 of FIGS. 7A-7G and the instrument 800 of FIGS. 8A-8F.

Once driven into the bone, the bone anchor 400 (with or without the receiver member 200 being attached thereto) can be used as a platform for other manipulations, such as distraction, compression, derotation, soft tissue retraction, and the like. These tasks can be achieved using instruments of the type described herein, including the instrument 700 of FIGS. 7A-7G and the instrument 800 of FIGS. 8A-8F.

Figure 1D:
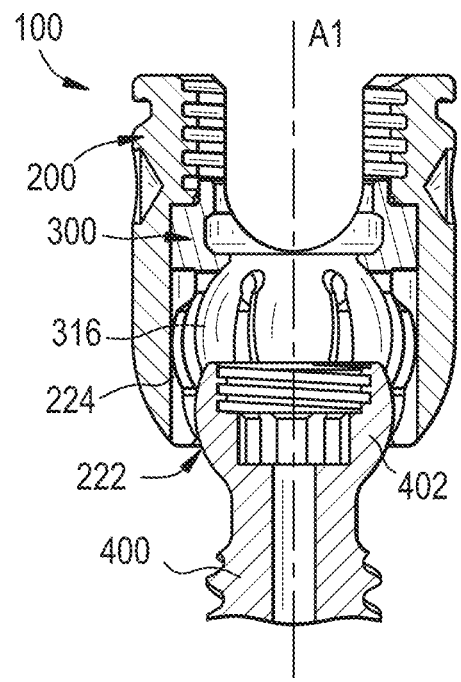
FIG. 1D is a sectional side view of the bone anchor assembly of FIG. 1A as the bone anchor is introduced into the collet.
Figure 1E:
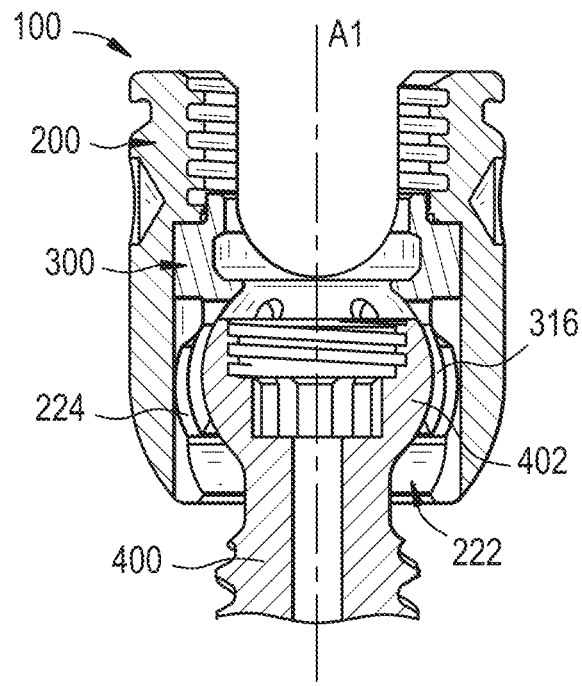
FIG. 1E is a sectional side view of the bone anchor assembly of FIG. 1A with the bone anchor fully seated within the collet.

The receiver member 200 and the collet 200 can be coupled to the head 402 of the bone anchor 400. For example, the bone anchor 400 can be bottom-loaded into the receiver member 200 by positioning the receiver member over the head 402 as shown in FIG. 1D and applying a distally-directed axial force to the receiver member. As shown in FIG. 1E, the fingers 316 of the collet 300 can be deformed from their resting position as the head 402 of the shank 400 is loaded into the distal end of the collet and can then return towards their resting position, capturing the head of the shank therein. In this position, the fingers 316 of the collet 300 are disposed in the upper proximal portion 224 of the cavity 222 in the receiver member 200. Accordingly, the shank 400 is free to rotate relative to the collet 300 about the axis A1 and to pivot polyaxially with respect to the collet within a cone of angulation extending out from the axis A1. While the shank 400 is free to move relative to the collet 300, the collet fingers 316 can apply a drag force to the shank, as described above. The receiver member 200 can be attached to the bone anchor 400 using a head insertion instrument 1100 of the type described below with respect to FIGS. 11A-11H.

Once the receiver member 200 is coupled to the bone anchor 400, the receiver member can serve as a platform for other steps in a surgical procedure, such as distraction, compression, derotation, soft tissue retraction, and the like. For example, a unilateral attachment instrument 1200 of the type described below with respect to FIGS. 12A-12F can be attached to the receiver member 200 and used to perform various manipulations, as described below with respect to FIGS. 12G-12K. A user may wish to remove the receiver member 200 and the collet 300 from the bone anchor 400, in which case the user can use a head removal instrument, e.g., of the type describe below with respect to FIG. 10.

Figure 1F:
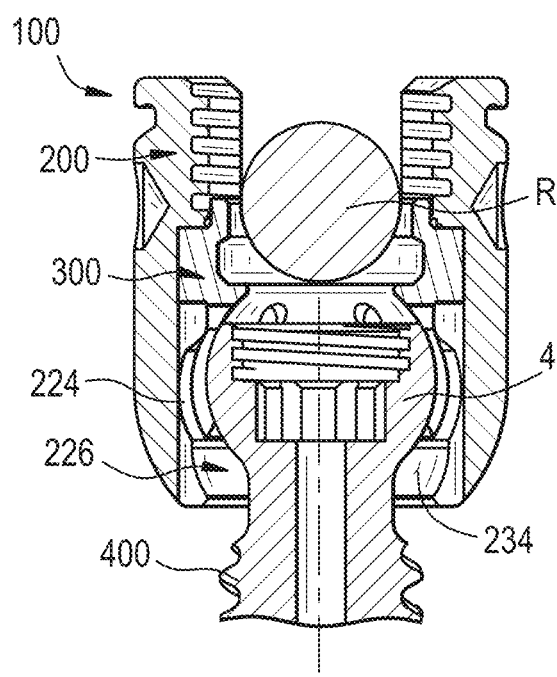
FIG. 1F is a sectional side view of the bone anchor assembly of FIG. 1A with a spinal rod seated therein prior to locking.
Figure 1G:
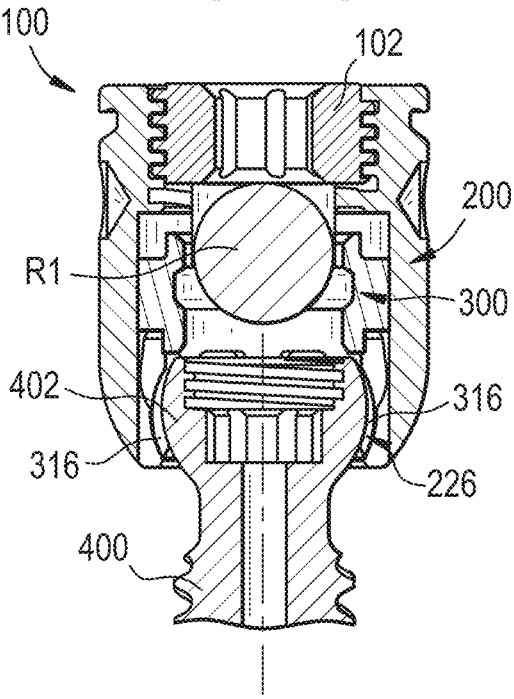
FIG. 1G is a sectional side view of the bone anchor assembly of FIG. 1A with a spinal rod seated and locked therein.
Figure 1H:
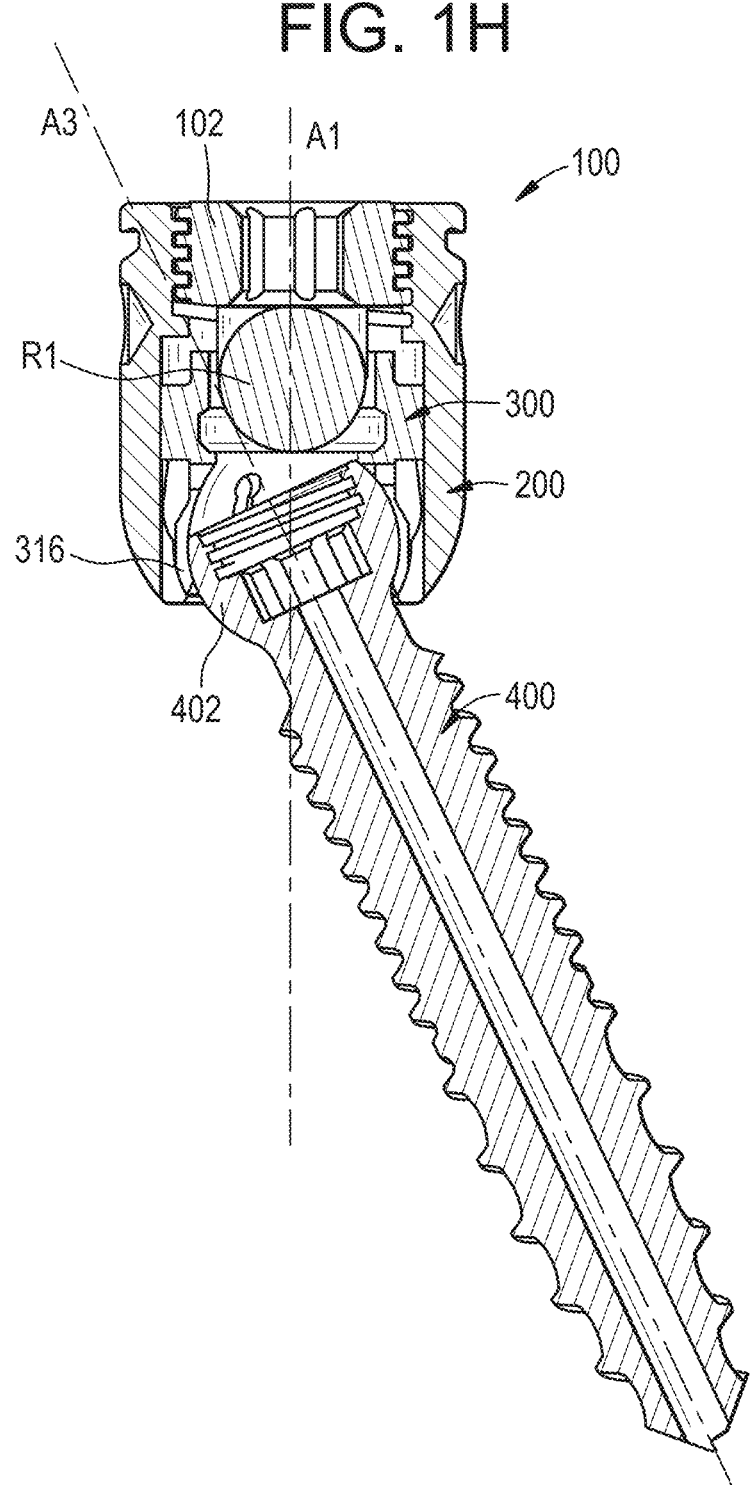
FIG. 1H is a sectional side view of the bone anchor assembly of FIG. 1A with a spinal rod seated therein and the bone anchor locked in a non-coaxial position with respect to the receiver member.

The assembled bone anchor assembly 100 can be used to secure an implant to the bone. For example, as shown in FIG. 1F, a spinal rod R1 can be inserted into the rod-receiving recess 206 of the receiver member 200. Before the rod R1 is fully seated and locked within the receiver member 200 the bone anchor 400 can remain movable relative to the receiver member. For example, the collet fingers 316 can remain in the upper proximal portion 224 of the cavity 222 such that they are not wedged between the head 402 and the interior surface 234 of the cavity. As shown in FIG. 1G, the set screw 102 or other closure mechanism can be applied to the receiver member 200 to drive the rod R1 and/or the collet 300 distally within the receiver member. As the collet fingers 316 move into the smaller diameter middle portion 226 of the cavity 222, the fingers can be wedged between the exterior surface of the head 402 of the shank 400 and the interior surface 234 of the cavity. Wedging the fingers 316 in this manner can be effective to lock movement of the bone anchor 400 relative to the receiver member 200. The bone anchor 400 can be locked at any of a variety of angles with respect to the receiver member 200, as shown for example in FIG. 1H. Applying the set screw or other closure mechanism 102 can also be effective to lock the rod R1 to lock movement of the rod relative to the receiver member 200. As noted above, a dual set screw or other construct can be used to independently lock movement of the shank 400 relative to the receiver member 200 and movement of the rod R1 relative to the receiver member.

The set screw 102 can be loosened if a user wishes to restore freedom of movement of the rod R1 and/or the shank 400 relative to the receiver member 200. In some embodiments, the bone anchor assembly 100 can be configured to remobilize automatically when the set screw 102 is loosened. This can advantageously eliminate the need to apply significant forces to the construct to break the bone anchor 400 free from the locked position. Automatic remobilization can be facilitated by the sphere-in-sphere arrangement provided by the spherical shank head 402 and the spherical middle portion 226 of the cavity 222 between which the spherical distal portion of the collet fingers 316 are wedged.

Modular Heads

As noted above, the bone anchor assembly 100 can be modular in the sense that various types or sizes of heads 200 can be coupled to various types or sizes of shanks 400. In the description above, reference is made to a head 200 in the form of a receiver member that defines a recess 206 for receiving a spinal rod. It will be appreciated, however, that various other head types can be used instead or in addition.

Figure 5A:
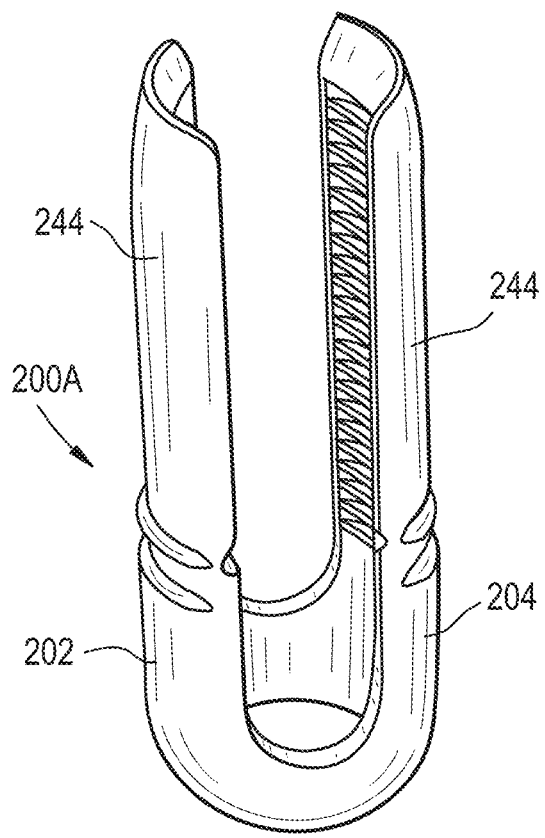
FIG. 5A is a perspective view of a reduction head that can be used in the bone anchor assembly of FIG. 1A.

For example, as shown in FIG. 5A, a reduction head 200A can be used. The reduction head 200A can be substantially similar to the receiver head 200 described above, but can include reduction tabs 244 that extend proximally from the arms 202, 204. The reduction tabs 244 can be formed integrally with the arms 202, 204 and can be configured to be broken away after use. In other embodiments, the reduction tabs 244 can be separate components that are selectively coupled to the arms 202, 204. The reduction tabs 244 can have a cross-sectional shape that matches that of the arms 202, 204. The reduction tabs 244 can include a threaded interior surface such that the tabs serve as a functional extension of the arms 202, 204 for set screw insertion or rod reduction.

Figure 5B:
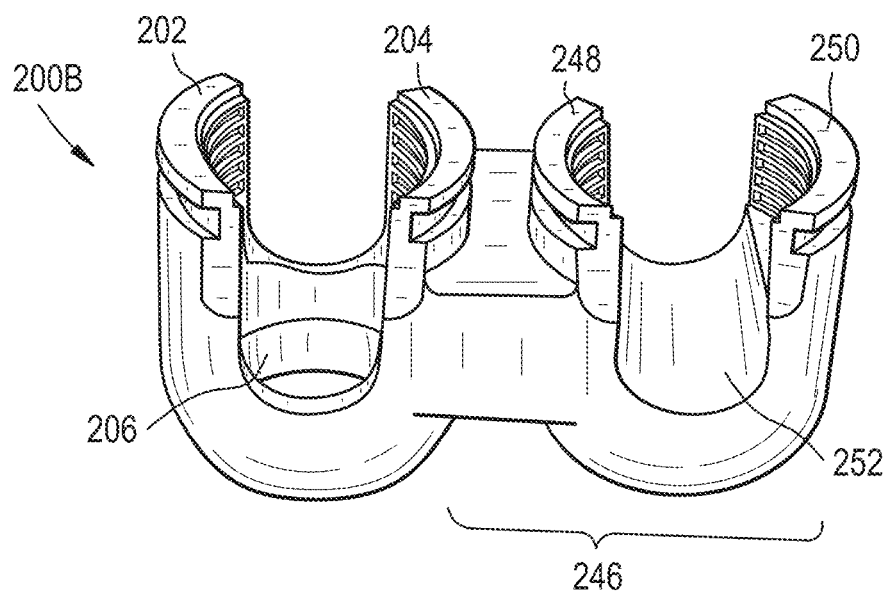
FIG. 5B is a perspective view of a tandem rod connector head that can be used in the bone anchor assembly of FIG. 1A.

By way of further example, as shown in FIG. 5B, a tandem rod connector head 200B can be used. The tandem rod head 200B can be substantially similar to the receiver head 200 described above, but can include a lateral wing portion 246 for attaching the head to a second spinal rod. The wing portion 246 can include first and second opposed arms 248, 250 that define a second rod-receiving recess 252 therebetween. A second set screw (not shown) can be threaded between the opposed arms 248, 250 to lock the second rod in the second rod-receiving recess 252. The rod recesses 206, 252 can have central axes that are parallel to one another as shown, or the central axes can extend at a non-zero angle relative to one another.

Figure 5C:
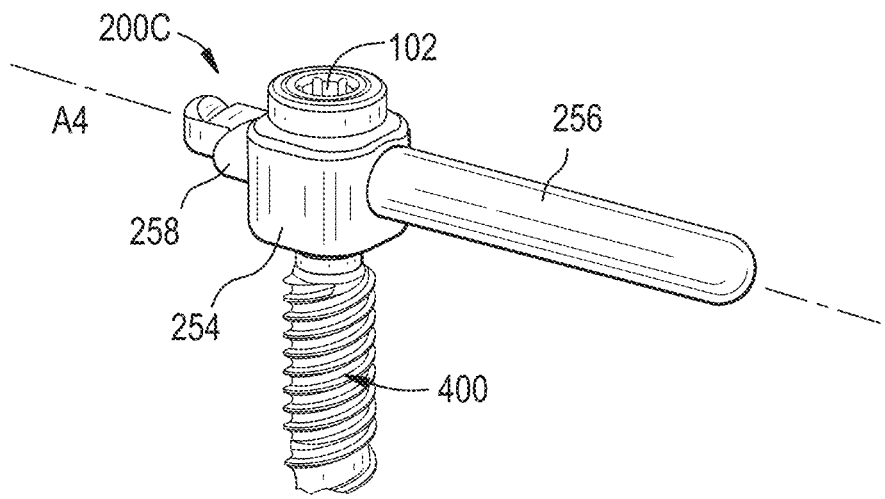
FIG. 5C is a perspective view of the bone anchor assembly of FIG. 1A, shown with a head having a built-in rod.
Figure 5D:
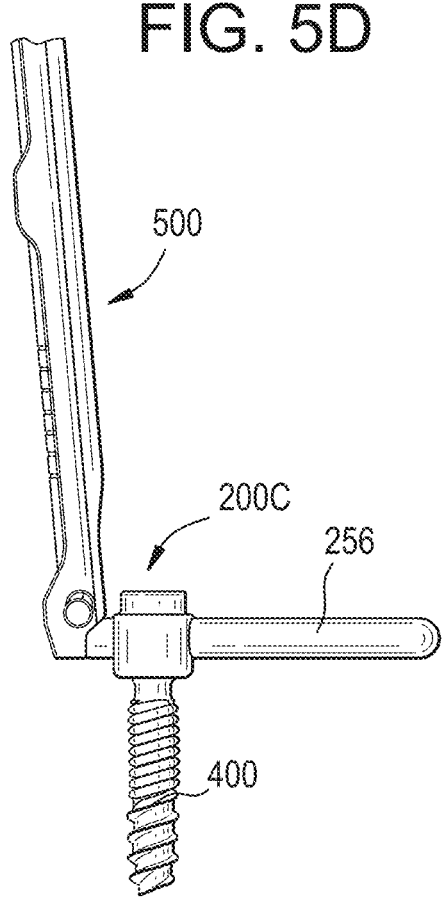
FIG. 5D is a side view of a rod introducer instrument attached to the bone anchor assembly of FIG. 5C.
Figure 5E:
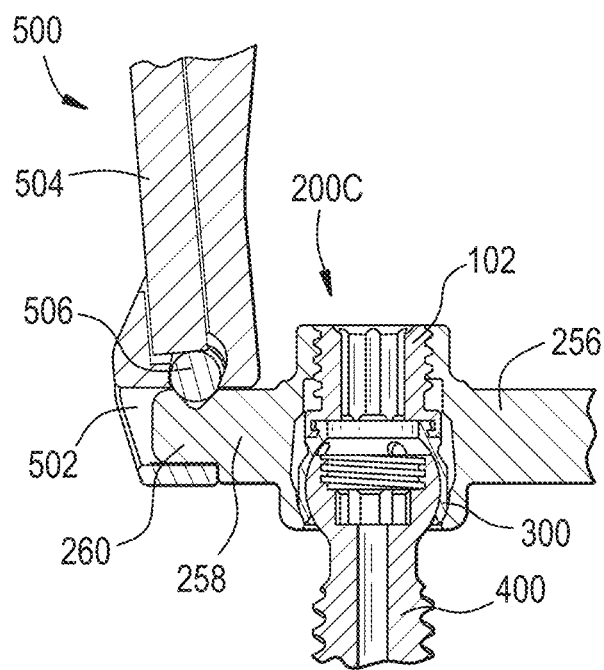
FIG. 5E is a sectional side view of the rod introducer instrument and bone anchor assembly of FIG. 5D.

As another example, a head having a built-in rod can be used. FIGS. 5C-5E illustrate a head 200C that includes a built-in rod. Except as indicated below and as will be readily appreciated by one having ordinary skill in the art, the head 200C can be substantially similar to the receiver head 200 described above. Instead of first and second opposed arms 202, 204, the head 200C can include an enclosed proximal portion 254. The set screw 102 can be elongated in the proximal-distal direction such that the distal surface of the set screw can bear directly against the collet 300, without an intervening rod. The head 200C can include a rod portion 256. The rod portion 256 can extend radially-outward along an axis A4 from an exterior sidewall of the head. The rod portion 256 can be formed integrally with the head 200C or can be selectively attached thereto. The head 200C can also include a second rod portion 258 with an engagement feature 260 formed thereon for mating with various instruments, such as a rod introducer 500. The second rod portion 258 can extend along the axis A4 from an opposite sidewall of the head 200C than the sidewall from which the first rod portion 256 extends. The engagement feature 260 can be formed at a terminal end of the second rod portion 258. The engagement feature 260 can be a substantially rectangular projection with a dimple formed in a proximal-facing surface thereof. As shown in FIG. 5E, a rod introducer instrument 500 can be coupled to the engagement feature 260 to allow insertion of the rod head 200C. In the illustrated embodiment, the rod introducer 500 includes a recess 502 at a distal end thereof sized to receive the rectangular portion of the engagement feature 260 therein such that the rod 258 cannot rotate relative to the instrument about the axis A4. The instrument 500 can include a pusher 504 that translates longitudinally within a lumen of the instrument to selectively hold an engagement pin 506 in contact with the dimple. When the pusher 504 is advanced distally within the lumen, it can force the pin 506 into contact with the dimple to hold the rod 258 firmly to the instrument 500 and prevent the rod from translating along the axis A4 with respect to the instrument. When the pusher 504 is retracted proximally within the lumen, it can allow the pin 506 to move out of engagement with the dimple, thereby allowing the rod 258 to be separated from the instrument 500 along the axis A4.

Instead of a second rod portion 258 with an engagement feature 260 thereon, or in addition, the enclosed proximal portion 254 of the head 200C can include an engagement feature. For example, as shown in FIGS. 5F-5J, the head 200C can include first and second cantilevered projections that define opposed arcuate grooves 264 in the exterior surface of the head. The grooves 264 can thus form a top-notch feature as described above. As shown in FIGS. 5I-5J, the grooves 264 can allow a retractor or extension shaft instrument 508 to be coupled to the head 200C. The instrument 508 can include first and second arms 510, 512 configured to pivot in and out to selectively engage the top-notch feature 264. The instrument 508 can define a central passage to allow other instruments to be passed therethrough, e.g., a driver instrument for advancing the shank portion 400 of the bone anchor assembly 100 or a driver instrument for advancing a set screw 102 within the head portion 200C.

Figure 6A:
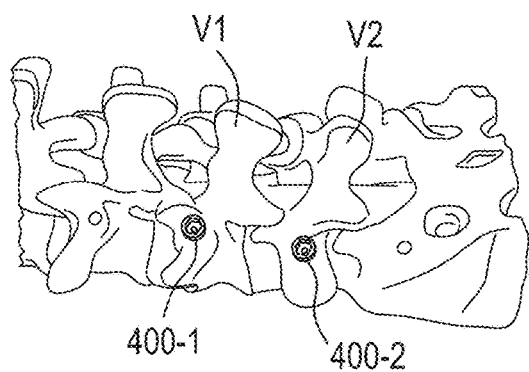
FIG. 6A is a perspective view of a step in a method of securing a spinal rod to first and second vertebrae.

FIGS. 6A-6H illustrate an exemplary method of using a head with a built-in rod to secure the rod to first and second vertebrae. As shown in FIG. 6A, first and second bone anchors 400_1, 400_2 of the type described above can be driven into respective first and second vertebrae V1, V2. The vertebrae V1, V2 can be adjacent as shown, or can be separated by one or more intervening vertebrae. The bone anchors 400_1, 400_2 can be driven into any part of the vertebrae V1, V2, such as the pedicles, laminae, or lateral masses thereof.

Before attaching receiver members or other heads to the bone anchors 400_1, 400_2, or at any other desired time, various other surgical steps can be performed. For example, decompression work or interbody work, including removal of all or a portion of a spinal disc and insertion of a fusion cage, can be performed.

Figure 6B:
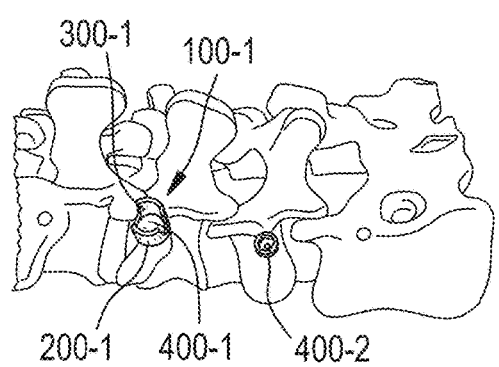
FIG. 6B is a perspective view of another step in a method of securing a spinal rod to first and second vertebrae.
Figure 6C:
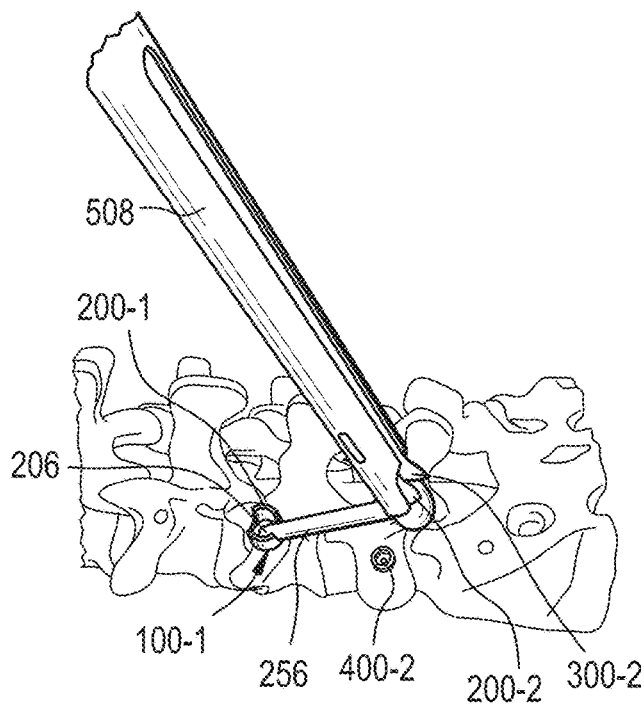
FIG. 6C is a perspective view of another step in a method of securing a spinal rod to first and second vertebrae.
Figure 6D:
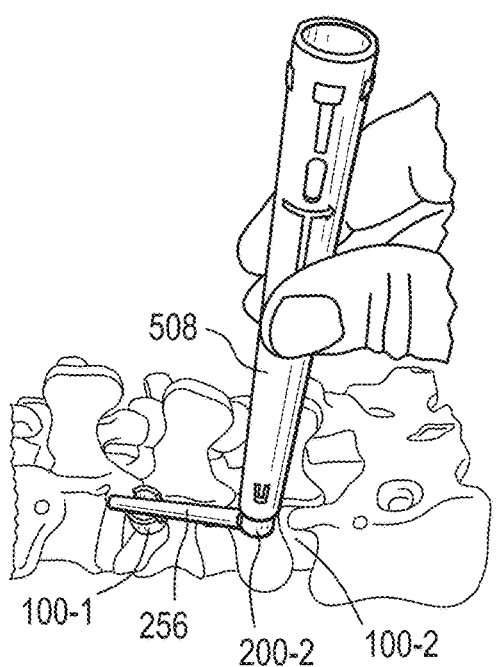
FIG. 6D is a perspective view of another step in a method of securing a spinal rod to first and second vertebrae.

As shown in FIG. 6B, a receiver member 200_1 and collet 300_1 of the type described above can be attached to the first bone anchor 400_1 to form a first bone anchor assembly 100_1. An integrated rod head 200_2 and collet 300_2 of the type described above can be attached to the second bone anchor 400_2, as shown in FIG. 6C. The method shown can be performed in a minimally-invasive manner, e.g., one in which discrete percutaneous incisions are formed over each bone anchor 400_1, 400_2 and the skin surface between the bone anchors is not incised. In this case, the integrated rod head 200_2 can be inserted through the percutaneous opening formed over the second bone anchor 400_2, with the rod portion 256 being inserted first. The rod portion 256 can then be tunneled below the skin surface into the rod-receiving recess 206 of the receiver member 200_1 of the first bone anchor assembly 100_1. The head 200_2 and collet 300_2 can then be lowered through the percutaneous opening and attached to the second bone anchor 400_2, as shown in FIG. 6D, to form a second bone anchor assembly 100_2. Insertion and manipulation of the integrated rod head 200_2 can be performed with a rod introducer instrument 508 coupled to the engagement feature of the head (e.g., a topnotch feature as shown or a second rod portion as described above with respect to FIGS. 5C-5E).

Figure 6E:
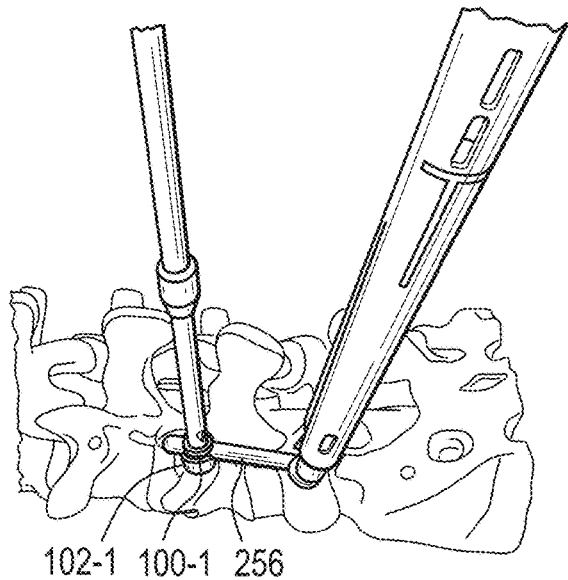
FIG. 6E is a perspective view of another step in a method of securing a spinal rod to first and second vertebrae.
Figure 6F:
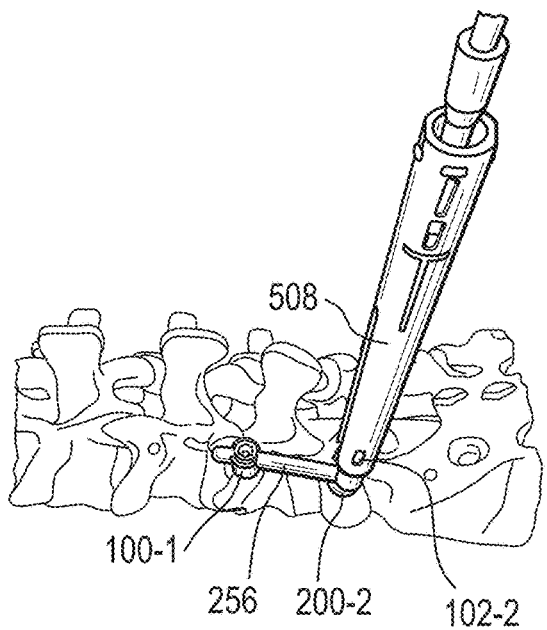
FIG. 6F is a perspective view of another step in a method of securing a spinal rod to first and second vertebrae.
Figure 6G:
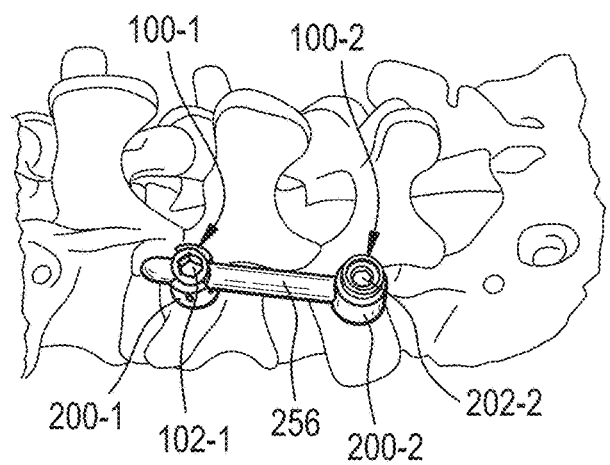
FIG. 6G is a perspective view of another step in a method of securing a spinal rod to first and second vertebrae.
Figure 6H:
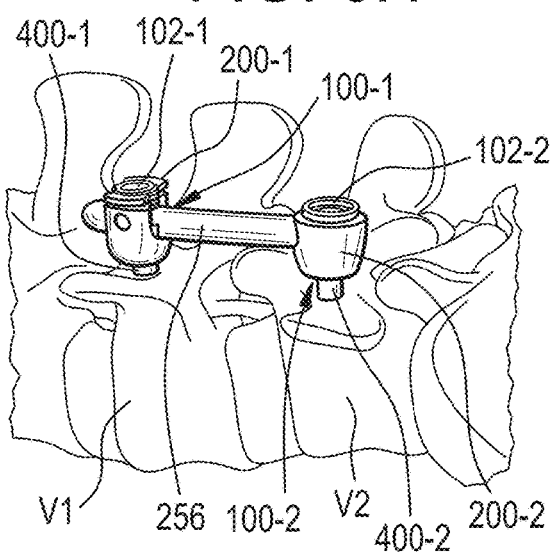
FIG. 6H is a perspective view of another step in a method of securing a spinal rod to first and second vertebrae.

As shown in FIG. 6E, a set screw 102_1 can be lowered through the percutaneous incision formed above the first bone anchor assembly 100_1 and tightened to secure the rod portion 256 to the first bone anchor assembly. Similarly, as shown in FIG. 6F, a set screw 102_2 can be lowered through the second percutaneous incision and tightened to lock the head 200_2 to the second bone anchor 400_2. The second set screw 102_2 can be inserted through the rod introducer instrument 508 as shown. The rod introducer instrument 508 can be used to apply a countertorque force during final tightening of the set screw 102_2. The rod introducer instrument 508 can then be removed, leaving an assembled construct attached to both vertebrae V1, V2 as shown in FIGS. 6G-6H. It will be appreciated that various manipulations can be performed before final tightening of the set screws 102_1, 102_2, such as compression, distraction, or derotation maneuvers. The rod introducer instrument 508 can be used to facilitate these manipulations by acting as a point through which forces can be applied to the bone anchor assembly and the vertebra in which it is implanted.

A number of other modular heads can also be used, including closed polyaxial modular heads, monoaxial modular heads, biased or favored-angle (e.g., sagittal or transverse) modular heads, extended tube or extended tab modular heads, uniplanar (e.g., sagittal or transverse) modular heads, and so forth. The bone anchor assembly 100 can be provided as part of a kit with a plurality of different head types or head sizes and a plurality of different shank types or shank sizes to enable the user to select the optimal combination for a particular use. Dimensions or parameters which can vary among components of the kit can include shank length, shank diameter, shank thread type, head size, rod-recess diameter, and the like.

Driver Instruments

FIGS. 7A-7G illustrate an exemplary driver instrument 700 that can be used to drive bone anchors into bone, e.g., bone anchors of the type shown in FIGS. 4F-4G. As shown, the instrument 700 can include a driver shaft 702, a countertorque sleeve 704, and a collar 706 for coupling the driver shaft to the countertorque sleeve. The collar 706 can retain one or more ball bearings 708 therein.

The driver shaft 702 can include proximal and distal ends 702p, 702d that define a longitudinal axis A5. The driver shaft 702 can be substantially cylindrical, or can have any of a variety of other shapes. The driver shaft 702 can have a hollow central channel or cannulation to facilitate insertion and use of the driver shaft over a guidewire. The distal end 702d of the driver shaft 702 can include an engagement feature for engaging a counterpart drive interface of a bone anchor 400. For example, the distal end 702d of the driver shaft 702 can include an exterior thread configured to mate with an interior thread of the bone anchor 400. The proximal end 702p of the driver shaft 702 can include flats or other features for applying a rotational force to the driver shaft. For example, the driver shaft 702 can include flats for non-rotatably coupling the driver shaft to a powered driver (e.g., an electric, pneumatic, or hydraulic drill or driver tool) or to a handle for manually rotating the driver shaft. By way of further example, the driver shaft 702 can have a handle integrally formed therewith. The driver shaft 702 can include a channel or groove 710 formed in an exterior surface thereof for receiving the ball bearings 708.

The countertorque sleeve 704 can include proximal and distal ends 704p, 704d that define a longitudinal axis A6. The countertorque sleeve 704 can define a hollow interior channel in which the driver shaft 702 can be disposed. The longitudinal axis A6 of the countertorque sleeve 704 can be coaxial with the longitudinal axis A5 of the driver shaft 702 when the instrument 700 is assembled. The distal end 704d of the countertorque sleeve 704 can include an engagement feature for engaging the countertorque features of the bone anchor 400. The illustrated features include a plurality of ramped projections 712 that extend distally from the distal-facing surface of the countertorque sleeve 704. Each projection 712 can include a ramped surface that extends obliquely from a plane transverse to the axis A6 and an abutment surface 714 that extends parallel to the axis A6. The abutment surfaces 714 can bear against the abutment surfaces 424 of the bone anchor 400 to prevent rotation of the countertorque sleeve 704 relative to the bone anchor in one direction (e.g., in a clockwise direction from the perspective of the surgeon as shown). The proximal end 704p of the countertorque sleeve 704 can include one or more lateral through-bores 716 in which respective ones of the ball bearings 708 are received.

The collar 706 can define an interior cavity sized to receive at least a proximal portion of the countertorque sleeve 704. An annular groove or channel 718 can be formed in the interior cavity of the collar 706 to receive at least a portion of the ball bearings 708 therein. A bias element 720 can be positioned within the cavity to bias the countertorque sleeve 704 distally with respect to the collar 706. While a coil spring 720 coaxial with the driver shaft 702 is shown, it will be appreciated that other bias elements can be used instead or in addition, such as leaf springs, torsion springs, and the like. A pin 722 can be positioned in an elongated slot 724 formed in the collar 706 and a hole 726 formed in the countertorque sleeve 704 to hold the collar, spring 720, and sleeve together in an assembled state. The elongated slot 724 can allow the collar 706 to translate longitudinally along the sleeve 704 within a limited range of movement.

The collar 706 can be slidable along the exterior of the countertorque sleeve 704 between a locked configuration and an unlocked configuration. In the locked configuration, as shown in FIG. 7C, the ball bearings 708 are disposed partially in the throughbores 716 of the countertorque sleeve 704 and partially in the groove 710 of the driver shaft 702. The collar 706 is urged proximally under the bias force of the spring 720, such that the inner groove 718 of the collar is offset from the throughbores 716 of the countertorque sleeve 704. Accordingly, the inner sidewall of the collar 706 holds the ball bearings 708 firmly in contact with the groove 710 in the driver shaft 702. In the locked configuration, the driver shaft 702 can be maintained at a fixed longitudinal position with respect to the countertorque sleeve 704 but can be free to rotate with respect to the countertorque sleeve.

Figure 7A:
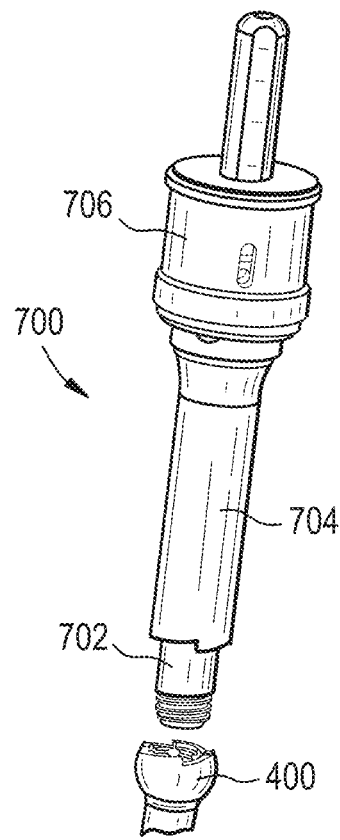
FIG. 7A is a perspective view of a driver instrument.
Figure 7B:
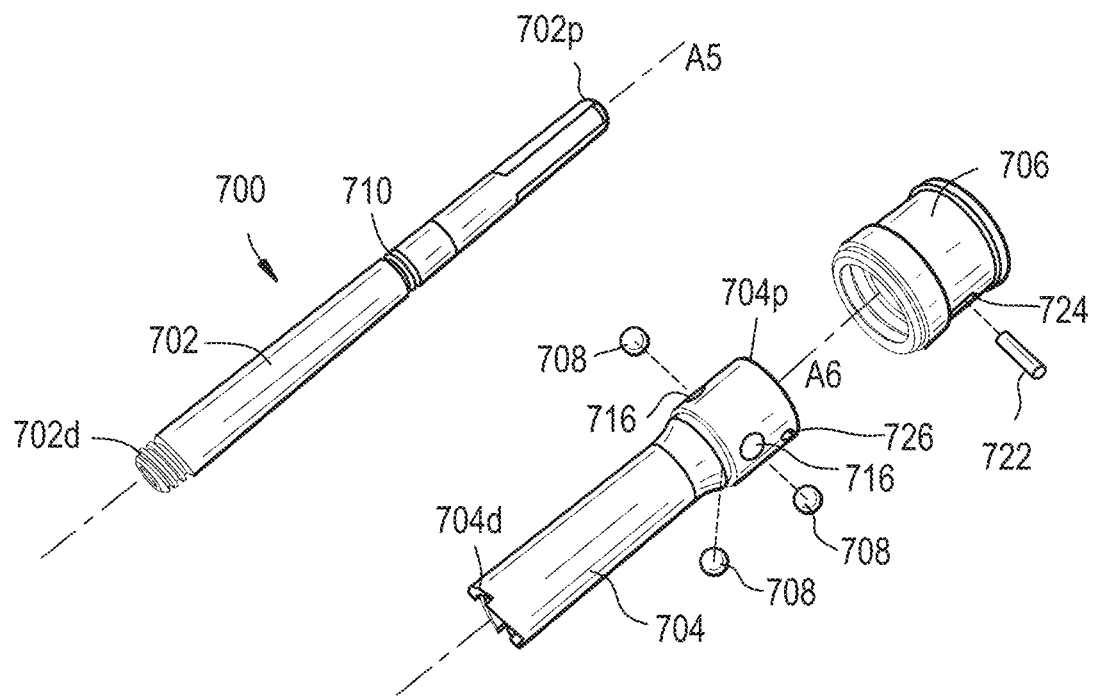
FIG. 7B is an exploded perspective view of the driver instrument of FIG. 7A.
Figure 7C:
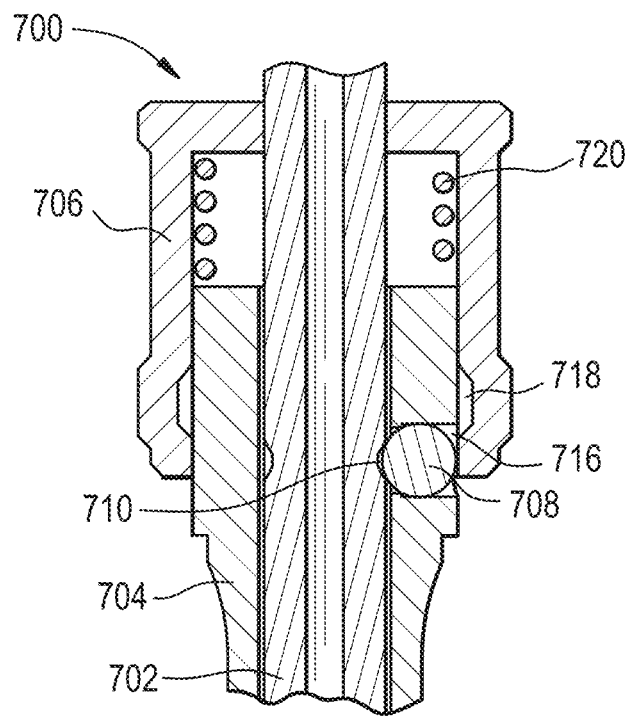
FIG. 7C is a sectional side view of the driver instrument of FIG. 7A in a locked configuration.
Figure 7D:
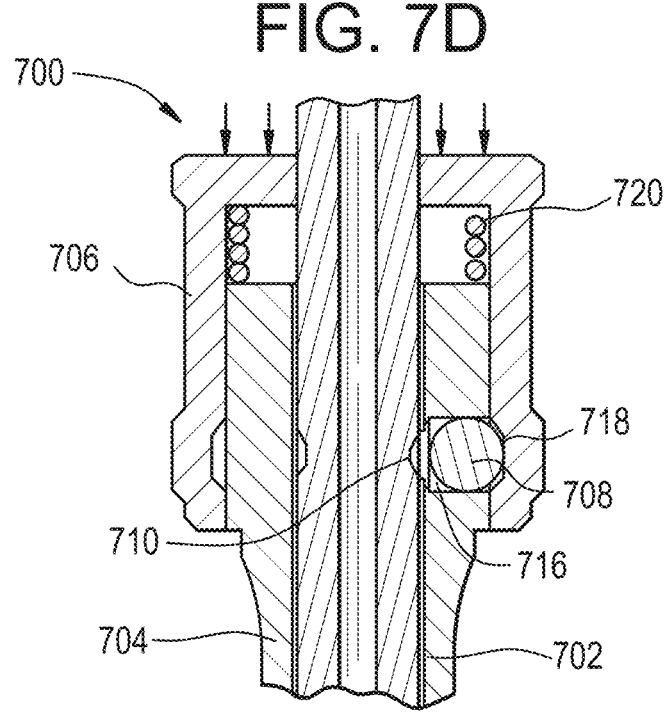
FIG. 7D is a sectional side view of the driver instrument of FIG. 7A in an unlocked configuration.

In the unlocked configuration, as shown in FIG. 7D, a distally-directed force can be applied to the collar 706 to urge the collar distally with respect to the countertorque sleeve 704. The collar 706 can be pushed distally to align the inner groove 718 of the collar with the throughbores 716 of the countertorque sleeve 704, allowing the ball bearings 708 to move in a radially-outward direction, out of engagement with the groove 710 formed in the driver shaft 702. In the unlocked configuration, the driver shaft 702 can be free to translate longitudinally with respect to the countertorque sleeve 704 and can be free to rotate with respect to the countertorque sleeve.

In use, the driver shaft 702 can be inserted into a bone anchor 400 and rotated with respect to the bone anchor to engage the threaded distal end 702d of the driver shaft with the threaded drive interface of the bone anchor, as shown in FIG. 7E. Before or after coupling the driver shaft 702 to the bone anchor 400, the driver shaft and the bone anchor can be loaded over a guidewire. The sleeve 704 and collar 706 assembly can be installed over the driver shaft 702, advancing the sleeve distally until the countertorque features of the sleeve engage the countertorque features of the bone anchor 400, as shown in FIG. 7F. In this position, the ball bearings 708 can engage the groove 710 formed in the driver shaft 702 to hold the sleeve 704 at a fixed longitudinal position with respect to the driver shaft and thereby hold the sleeve in engagement with the countertorque features of the bone anchor 400. A rotational force can be applied to the driver shaft 702 (or to the sleeve 704) to drive the bone anchor 400 into bone. When removal of the driver shaft 702 from the bone anchor 400 is desired, the countertorque sleeve 704 can be held stationary while the driver shaft is rotated in an opposite direction to unthread the driver shaft from the drive interface of the bone anchor. In some cases, the user may wish to leave the driver shaft 702 engaged with the bone anchor 400. As shown in FIG. 7G, the sleeve 704 and the collar 706 can be removed from the driver shaft 702 (e.g., by advancing the collar distally to release the ball bearings 708 from the driver shaft as described above). The driver shaft 702 can be left behind as a post to facilitate other steps in a surgical procedure. For example, the driver shaft 702 can serve as an attachment point for a distractor or access port, or can be used to apply a derotation, distraction, or compression force to a vertebra in which the bone anchor 400 is implanted. While not shown in FIGS. 7A-7G, the driver instrument 700 can include a depth stop, e.g., of the type described below with respect to the driver instrument 800 of FIGS. 8A-8F.

FIGS. 8A-8F illustrate an exemplary driver instrument 800 that can be used to drive bone anchors into bone, e.g., bone anchors of the type shown in FIGS. 4H-4I. As shown, the instrument 800 can include a driver shaft 802, a countertorque sleeve 804, and a collar 806 for coupling the driver shaft to the countertorque sleeve. The instrument 800 can include a depth stop 828 to prevent over-insertion of the bone anchor 400.

The driver shaft 802 can include proximal and distal ends 802p, 802d that define a longitudinal axis A7. The driver shaft 802 can be substantially cylindrical, or can have any of a variety of other shapes. The driver shaft 802 can have a hollow central channel or cannulation to facilitate insertion and use of the driver shaft over a guidewire. The distal end 802d of the driver shaft 802 can include an engagement feature for engaging a counterpart drive interface of a bone anchor 400. For example, the distal end 802d of the driver shaft 802 can include an exterior thread configured to mate with an interior thread of the bone anchor 400. The proximal end 802p of the driver shaft 802 can include flats or other features for applying a rotational force to the driver shaft. For example, the driver shaft 802 can include flats for non-rotatably coupling the driver shaft to a powered driver (e.g., an electric, pneumatic, or hydraulic drill or driver tool) or to a handle for manually rotating the driver shaft. By way of further example, the driver shaft 802 can have a handle integrally formed therewith. The driver shaft 802 can include an exterior thread 810 formed adjacent the proximal end of the driver shaft for engaging the collar 806.

The countertorque sleeve 804 can include proximal and distal ends 804p, 804d that define a longitudinal axis A8. The countertorque sleeve 804 can define a hollow interior channel in which the driver shaft 802 can be disposed. The longitudinal axis A8 of the countertorque sleeve 804 can be coaxial with the longitudinal axis A7 of the driver shaft 802 when the instrument 800 is assembled. The distal end 804d of the countertorque sleeve 804 can include an engagement feature for engaging the countertorque features of the bone anchor 400. The illustrated features form a "castle" pattern defined by a plurality of projections 812 that extend distally from the distal-facing surface of the sleeve 804. Each projection 812 can include a first abutment surface 814 that extends parallel to the axis A8 and a second abutment surface 830 that extends parallel to the axis A8. The abutment surfaces 814, 830 can bear against the abutment surfaces 426, 428 of the bone anchor 400 to prevent rotation of the countertorque sleeve 804 relative to the bone anchor in both clockwise and counterclockwise directions. In some embodiments, the engagement feature can include angled teeth, e.g., in the form of a star-lock or star-grind interface.

The collar 806 can define an interior cavity sized to receive at least a proximal portion of the countertorque sleeve 804. At least a portion of the cavity can define an interior thread 832 configured to threadably engage the exterior thread 810 formed on the driver shaft 802. Accordingly, rotation of the collar 806 about the driver shaft 802 can be effective to translate the collar longitudinally with respect to the driver shaft. The collar 806 can include holes or channels 834 formed therein configured to align with a groove 836 formed in the proximal end of the sleeve 804 when the instrument 800 is assembled. A pin 838 can be inserted through the holes 834 to position the pin within the groove 836 formed in the sleeve 804. Accordingly, the sleeve 804 can be maintained at a fixed longitudinal position relative to the collar 806 while still being free to rotate relative to the collar about the axis A8.

Figure 8A:
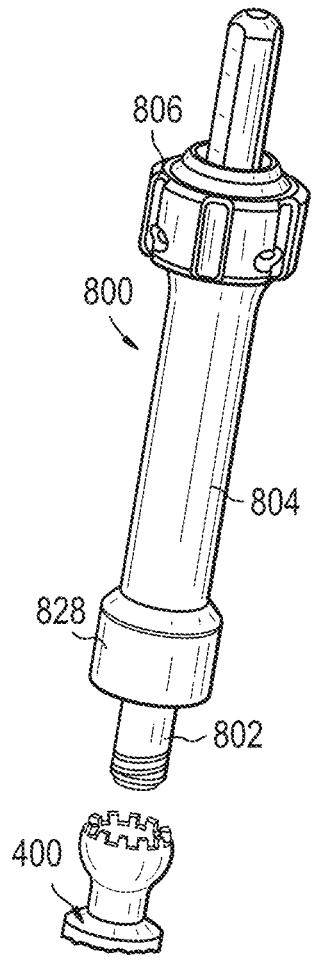
FIG. 8A is a perspective view of a driver instrument.
Figure 8B:
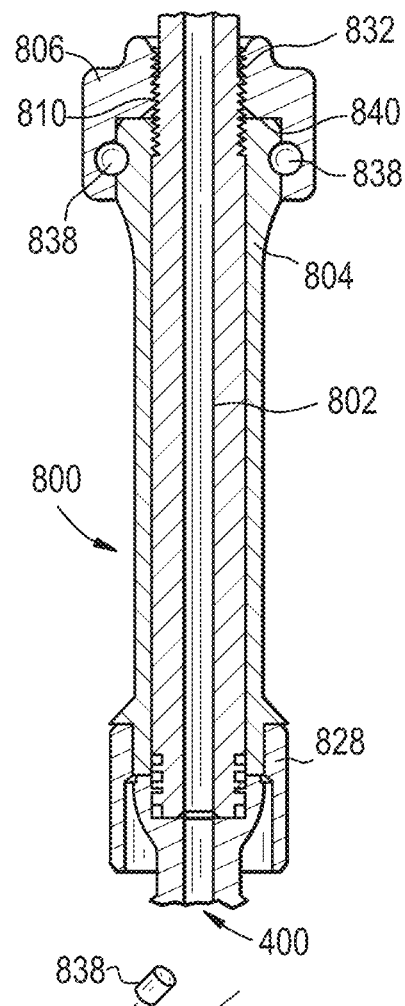
FIG. 8B is a sectional side view of the driver instrument of FIG. 8A.
Figure 8C:
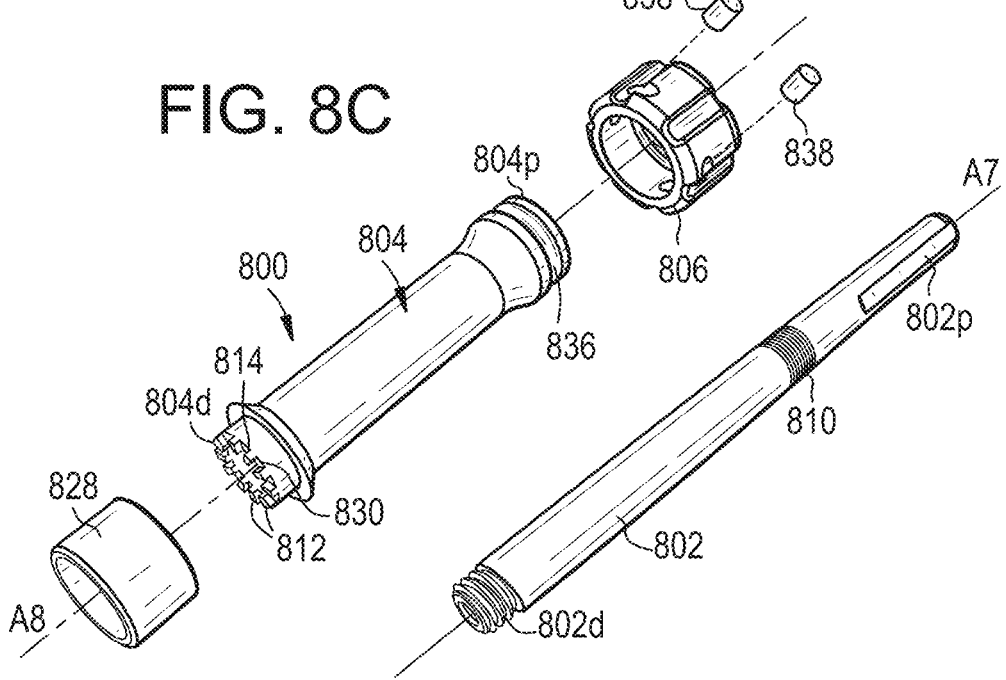
FIG. 8C is an exploded perspective view of the driver instrument of FIG. 8A.
Figure 8D:
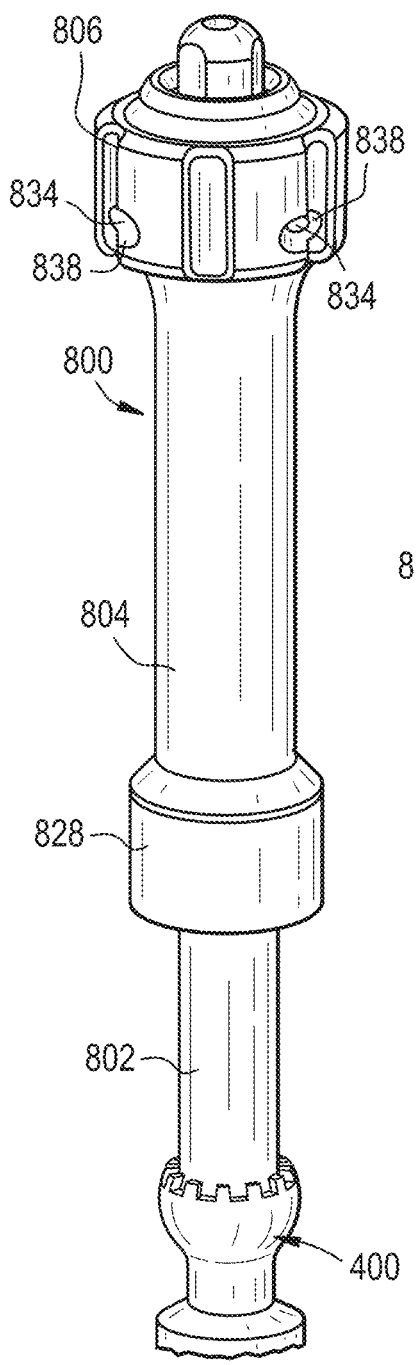
FIG. 8D is a perspective view of a step in a method of driving a bone anchor using the driver instrument of FIG. 8A.
Figure 8E:
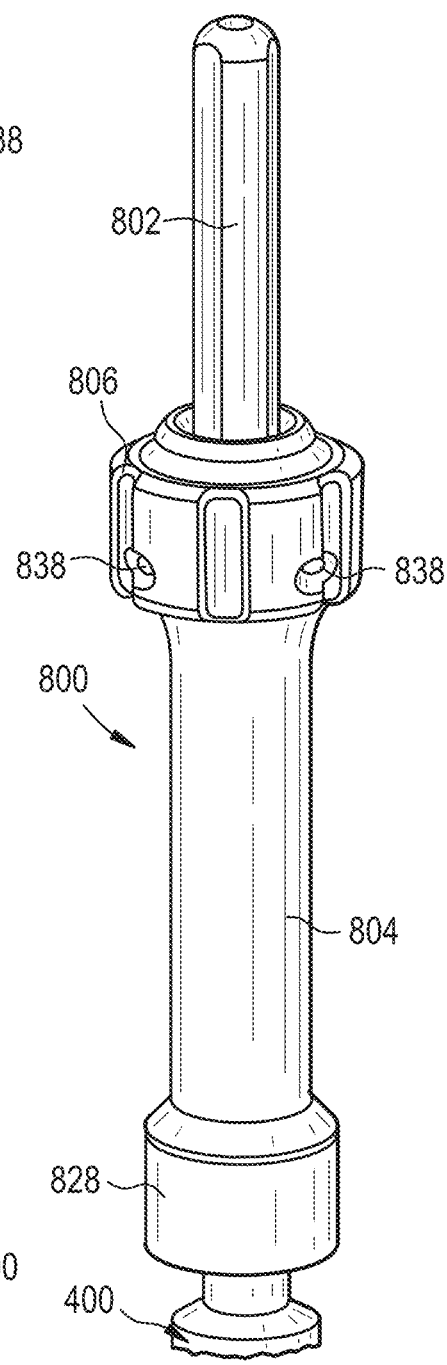
FIG. 8E is a perspective view of another step in a method of driving a bone anchor using the driver instrument of FIG. 8A.
Figure 8F:
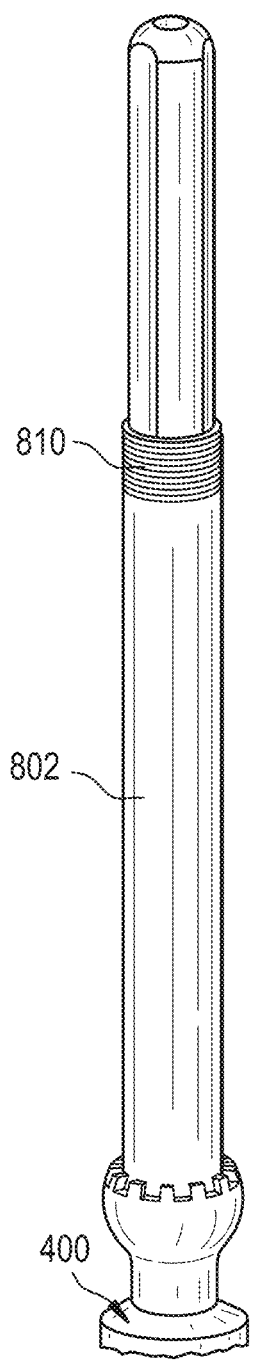
FIG. 8F is a perspective view of another step in a method of driving a bone anchor using the driver instrument of FIG. 8A.
Figure 11A:
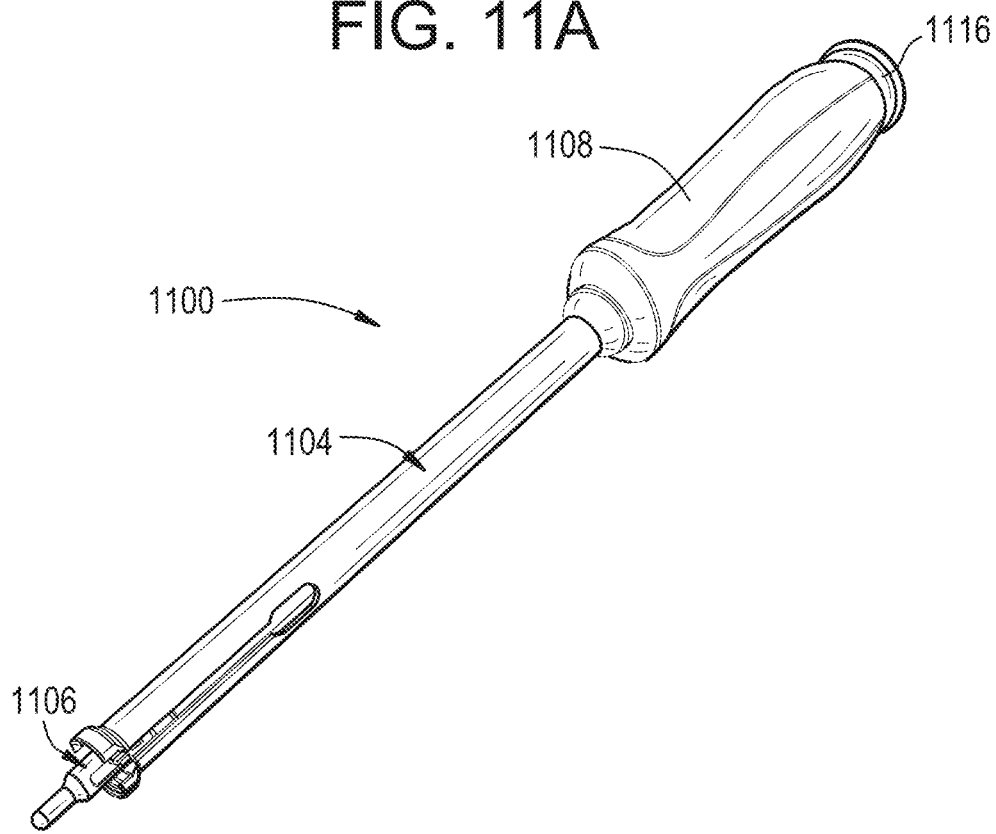
FIG. 11A is a perspective view of a head attachment instrument.
Figure 11B:
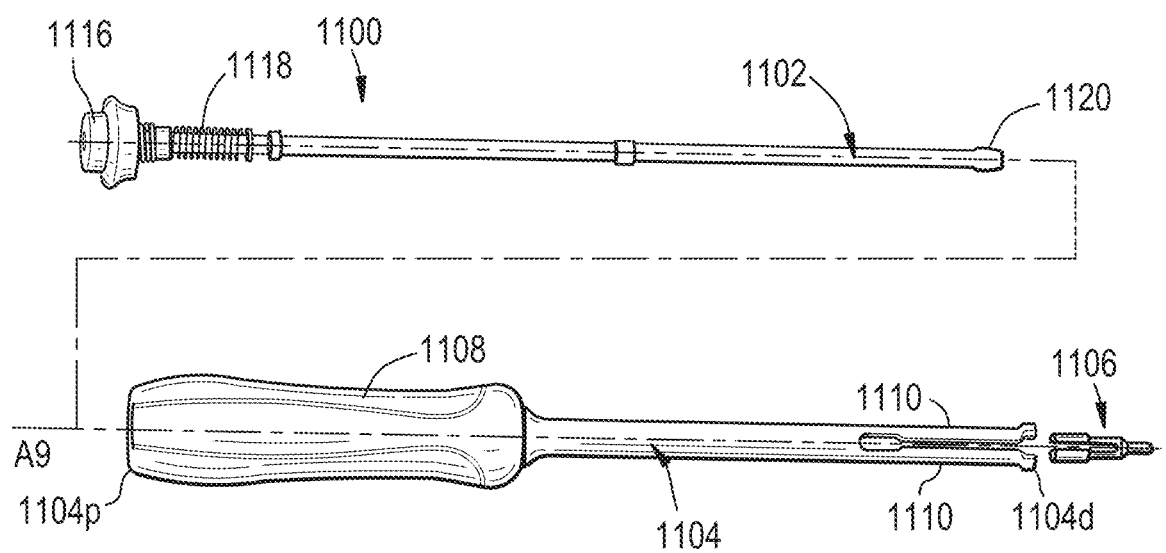
FIG. 11B is an exploded side view of the instrument of FIG. 11A.
Figure 11C:
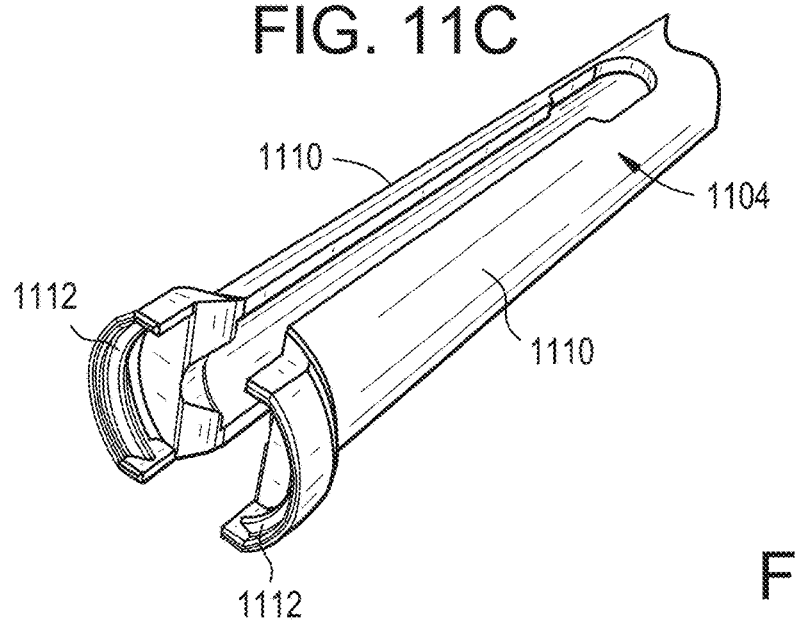
FIG. 11C is a perspective view of the outer sleeve of the instrument of FIG. 11A.
Figure 11D:
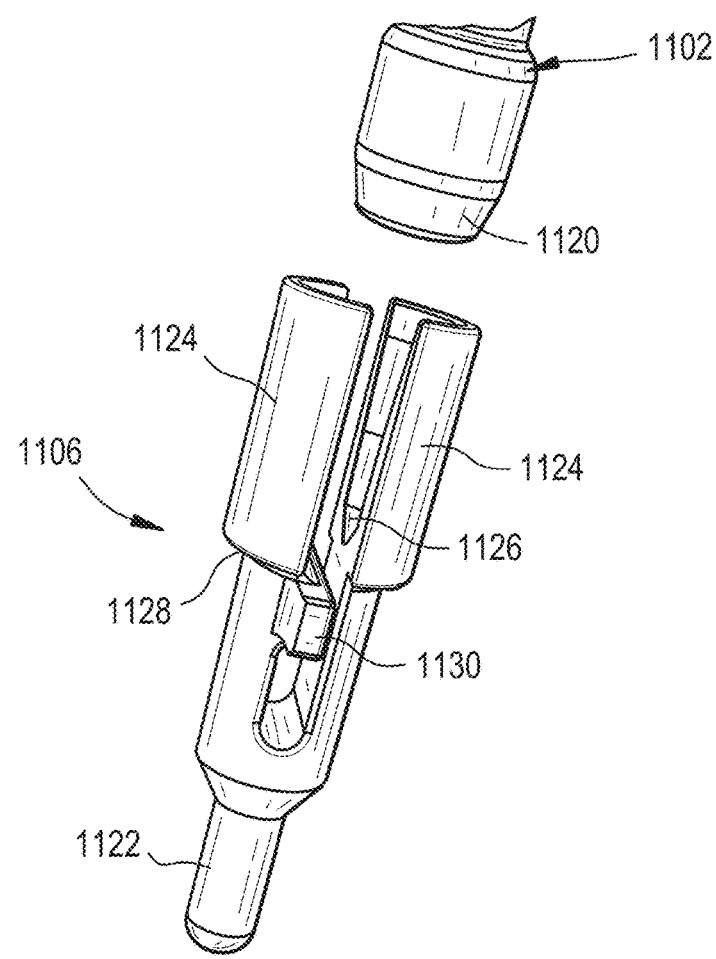
FIG. 11D is a perspective view of the push rod and release element of the instrument of FIG. 11A.

In use, the driver shaft 802 can be inserted into a bone anchor 400 and rotated with respect to the bone anchor to engage the threaded distal end 802d of the driver shaft with the threaded drive interface of the bone anchor, as shown in FIG. 8D. Before or after coupling the driver shaft 802 to the bone anchor 400, the driver shaft and the bone anchor can be loaded over a guidewire. The sleeve 804 and the collar 806 assembly can be installed over the driver shaft 802. The collar 806 can be rotated to advance the sleeve 804 distally, without rotating the sleeve, until the countertorque features of the sleeve engage the countertorque features of the bone anchor 400, as shown in FIG. 8E. In this position, the sleeve 804 can be sandwiched between a shoulder surface 840 formed in the collar 806 (see FIG. 8B) and the proximal-facing surface of the bone anchor 400, thereby holding the sleeve in engagement with the countertorque features of the bone anchor. A rotational force can be applied to the driver shaft 802 (or to the sleeve 804) to drive the bone anchor 400 into bone. When removal of the driver shaft 802 from the bone anchor 400 is desired, the countertorque sleeve 804 can be held stationary while the driver shaft is rotated in an opposite direction to unthread the driver shaft from the drive interface of the bone anchor. In some cases, the user may wish to leave the driver shaft 802 engaged with the bone anchor 400. As shown in FIG. 8F, the sleeve 804 and the collar 806 can be removed from the driver shaft 802, e.g., by rotating the collar to unthread it from the driver shaft. The driver shaft 802 can be left behind as a post to facilitate other steps in a surgical procedure. For example, the driver shaft 802 can serve as an attachment point for a distractor or access port, or can be used to apply a derotation, distraction, or compression force to a vertebra in which the bone anchor 400 is implanted.

The depth stop 828 can include a cylindrical sleeve mated to or formed integrally with the distal end of the countertorque sleeve 804. The depth stop 828 can define a hollow interior sized to receive the head 402 of the bone anchor 400 therein. As the bone anchor 400 is driven into the bone, the depth stop 828 will eventually contact the bone surface and prevent further insertion of the bone anchor. This can help ensure that a sufficient length of the bone anchor 400 is left protruding above the bone surface to allow attachment of the receiver member or head 200.

FIG. 9 illustrates another exemplary driver instrument 900 that can be used instead of or in addition to the instruments 700, 800 described above. The instrument 900 can include a standard hexalobe drive interface 902 as shown, or any of a variety of other drive interfaces.

Head Removal Instruments

FIG. 10 illustrates an exemplary instrument 1000 for removing a head 200 from a bone anchor 400. As shown, the instrument 1000 can include an inner rod 1002 and an outer sleeve 1004. The outer sleeve 1004 can define a central lumen or channel sized to receive the inner rod 1002 therein. The longitudinal position of the inner rod 1002 with respect to the outer sleeve 1004 can be adjustable. For example, the inner rod 1002 can include an exterior thread that engages a corresponding interior thread of the outer sleeve 1004 such that rotation of the outer sleeve about the inner rod is effective to translate the inner rod proximally or distally relative to the outer sleeve. The distal end of the outer sleeve 1004 can define a bearing surface 1006 configured to bear against a head 200. In the illustrated embodiment, the distal-facing surface 1006 of the outer sleeve 1004 is configured to abut and bear against a proximal-facing surface of the head 200. The distal end of the inner rod 1002 can include features for engaging the collet 300 to fix a longitudinal position of the collet with respect to the inner rod. For example, as shown, the inner rod 1002 can include opposed ears 1008 that extend radially-outward therefrom. The ears 1008 can be sized to be received within the recesses 312 formed in the arms 302, 304 of the collet 300.

In use, the inner rod 1002 can be advanced distally with respect to the outer sleeve 1004 such that the inner rod protrudes from the outer sleeve. The distal end of the inner rod 1002 can be inserted into an assembled bone anchor assembly 100 by positioning the distal end between the arms 302, 304 of the collet 300. The user can then grasp a proximal end of the inner rod 1002 and rotate it 90 degrees about its axis relative to the collet 300 to position the ears 1008 of the inner rod within the recesses 312 of the collet, thereby fixing the longitudinal position of the collet with respect to the inner rod. The user can then rotate the outer sleeve 1004 about the inner rod 1002 to advance the outer sleeve distally relative to the inner rod until the outer sleeve abuts the proximal end of the receiver member 200. Continued rotation of the outer sleeve 1004 will pull the inner rod 1002, and the collet 300 fixed thereto, proximally relative to the receiver member 200 until the collet fingers 316 are positioned within the upper portion 224 of the cavity 222 formed in the receiver member. When the fingers 316 are positioned in the upper portion 224 of the cavity 222, they can be free to deflect radially-outward to release the head 402 of the bone anchor 400. Accordingly, once the collet 300 is pulled proximally within the receiver member 200, the user can apply a proximal pulling force to the instrument 1000 to separate the receiver member and the collet from the bone anchor 400. The instrument 1000 can include a plunger (not shown) slidably and/or threadably disposed in the inner rod 1002 that can bear against and urge the head 402 of the bone anchor 400 distally out of the receiver member 200, such that proximal pulling forces applied by the user are not applied (or are not applied to the same degree) to the bone anchor. This can advantageously prevent stressing the bone anchor/bone interface. After separating the bone anchor 400, the above steps can be performed in reverse order and in reverse direction to release the receiver member 200 and the collet 300 from the instrument 1000.

The instrument 1000 can also be used to assemble the collet 300 to the receiver member 200. For example, the inner rod 1002 can be mated to the collet 300 and the outer sleeve 1004 can be rotated about the inner rod to pull the inner rod, and the collet coupled thereto, proximally into the distal end of the receiver element 200. Once the collet fingers 316 flex outward to retain the collet 300 within the cavity 222 of the receiver member 200, the inner rod 1002 can be decoupled from the collet and the instrument 1000 can be separated from the now-assembled receiver member and collet.

Head Insertion Instruments

FIGS. 11A-11H illustrate an exemplary instrument 1100 for attaching the receiver member 200 to the bone anchor 400. The instrument 1100 can be used for in-situ attachment of the receiver member 200 to the bone anchor 400. In other words, the bone anchor 400 can be implanted in a bone and, thereafter, a receiver member 200 can be coupled thereto using the instrument 1100.

In a modular bone anchor assembly, it is conceivable that sub-optimal head attachment can occur, for example if soft tissue or other debris blocks complete attachment to the bone anchor, or if the user fails to apply sufficient force when mating the head to the bone anchor. Accordingly, it may be desirable to give the user some positive indication that the head is securely coupled to the bone anchor, or to prevent the head from being released from an insertion instrument if the head is not securely attached to the bone anchor. This functionality can give the user increased confidence that an adequate connection has been made between the receiver member and the bone anchor.

The instrument 1100 can be configured such that the receiver member 200 is only released from the instrument when the receiver member is securely coupled to the bone anchor 400. This can give the user confidence that the receiver member 200 is securely attached, since the user will only be able to remove the inserter instrument 1100 when a secure attachment is achieved.

As shown, the instrument 1100 can include a push rod 1102, an outer sleeve 1104, and a release element 1106. The outer sleeve 1104 can include proximal and distal ends 1104p, 1104d that define a longitudinal proximal-distal axis A9. The outer sleeve 1104 can define a central lumen or channel sized to receive the push rod 1102 and the release element 1106 therein. The proximal end 1104p of the outer sleeve 1104 can include a handle 1108 or other feature to facilitate gripping of the instrument 1100 by the user. The distal end 1104d of the sleeve 1104 can include opposed slits such that the distal end is separated into first and second cantilevered arms 1110. The arms 1110 can be at least somewhat flexible such that the free ends of the arms are movable towards and away from one another to selectively engage a receiver member 200. The slits can include enlarged proximal cut-outs to provide a stress relief and facilitate such movement of the arms 1110. The free ends of the arms 1110 can include an engagement feature for engaging a corresponding feature of the receiver member 200. In the illustrated embodiment, the arms 1110 include arcuate shelves 1112 that extend radially-inward from the arms, the shelves being configured to seat within corresponding arcuate grooves 210 of the receiver member 200 to secure the receiver member to the outer sleeve 1104. The arms 1110 can have at least a first position in which the shelves 1112 are seated within the grooves 210 of the receiver member 200 to secure the receiver member to the instrument 1100, and a second position in which the arms are deflected radially-outward from the first position to unseat the shelves from the grooves of the receiver member to release the receiver member from the instrument.

The arms 1110 can also include a shoulder 1114 that engages a corresponding shoulder of the release element 1106 to limit distal travel of the release element relative to the outer sleeve 1104. In other words, the shoulders 1114 of the arms 1110 can prevent the release element 1106 from falling out of the distal end of the outer sleeve 1104.

The push rod 1102 can be slidably disposed within the outer sleeve 1104 such that the push rod can translate longitudinally relative to the outer sleeve. A proximal end of the push rod 1102 can be coupled to a button, lever, or other actuator 1116, which can be actuated by a user to advance the push rod distally within the outer sleeve 1104. A bias element 1118 can be disposed between the push rod 1102 and the outer sleeve 1104 to bias the push rod proximally with respect to the outer sleeve. Accordingly, upon release of the button 1116, the push rod 1102 can be retracted proximally within the sleeve 1104 under the bias of the biasing element 1118. While a coil spring is shown, it will be appreciated that other biasing elements can be used instead or in addition. The distal end of the push rod 1102 can include a bearing surface 1120 configured to bear against a corresponding interior bearing surface of the release element 1106, as described further below. The bearing surface 1120 of the push rod 1102 can be conical, curved, tapered, or ramped.

The release element 1106 can include a distal projection 1122 configured to protrude from the distal end 1104d of the outer sleeve 1104 to contact a bone anchor 400. The release element 1106 can include opposed arms 1124 that extend proximally from the release element. The arms 1124 can be configured to flex toward and/or away from each other during operation of the instrument 1100. The arms 1124 can include recesses formed therein that define a bearing surface 1126 configured to bear against the bearing surface 1120 of the push rod 1102. The bearing surfaces 1126 of the arms 1124 can be conical, curved, tapered, or ramped. The release element 1106 can include features to limit movement of the release element with respect to the outer sleeve 1104. For example, the release element 1106 can include a distal-facing shoulder 1128 configured to engage the proximal-facing shoulder 1114 of the outer sleeve 1104 to limit distal longitudinal travel of the release element relative to the sleeve. By way of further example, the release element 1106 can include opposed tabs 1130 that project radially-outward therefrom and slide within the slits formed in the outer sleeve 1104 to restrict rotation of the release element with respect to the outer sleeve. The tabs 1130 can ensure that the arms 1124 of the release element 1106 are aligned with the arms 1110 of the outer sleeve 1104.

Operation of the instrument 1100 is illustrated in FIGS. 11E-11H. As shown, a receiver member 200 or other modular head component can be loaded into the instrument 1100 by engaging the shelves 1112 of the outer sleeve 1104 with grooves 210 formed in the receiver member, thereby securing the receiver member to the outer sleeve. The instrument 1100 can then be used to attach the receiver member 200 to a bone anchor 400. The bone anchor 400 can have been previously implanted in bone. As the instrument 1100 is used to lower the receiver member 200 down over the bone anchor 400, the distal projection 1122 of the release element 1106 comes into contact with the bone anchor. Continued advancement of the instrument 1100 with respect to the bone anchor 400 can cause the release element 1106 to slide proximally within the outer sleeve 1104.

As shown in FIGS. 11E-11F, when the head 402 of the bone anchor 400 is fully-seated within the receiver member 200, the user can depress the actuation button 1116 to release the receiver member from the insertion instrument 1100. Specifically, pressing the button 1116 can cause the push rod 1102 to translate distally within the outer sleeve 1104. As the push rod 1102 urges the release element 1106 distally, distal advancement of the release element is prevented by the bone anchor 400. Accordingly, the bearing surface 1120 of the push rod 1102 bears against the bearing surface 1126 of the release element 1106 to splay the arms 1124 of the release element radially-outward. As the arms 1124 of the release element 1106 move radially-outward, they push the arms 1110 of the outer sleeve 1104 radially-outward, thereby disengaging the shelves 1112 from the grooves 210 formed in the receiver member 200 and releasing the receiver member from the instrument 1100. Once the receiver member 200 is released, the instrument 1100 can be removed, leaving the receiver member securely coupled to the bone anchor 400.

As shown in FIGS. 11G-11H, the instrument 1100 can advantageously prevent the receiver member 200 from being released from the instrument when the receiver member is not fully seated on the bone anchor 400. In particular, when the user presses the button 1116 in this scenario, the push rod 1102 translates distally within the outer sleeve 1104. Because the bone anchor 400 is not fully seated within the receiver member 200, the projection 1122 of the release element 1106 does not contact the bone anchor 400 to limit distal travel of the release element relative to the outer sleeve 1104, or contacts the bone anchor only after sufficient distal travel of the release element occurs. Accordingly, when the push rod 1102 contacts the release element 1106, it simply pushes the release element distally, without the bearing surface 1120 of the push rod camming over the bearing surface 1126 of the release element and without causing the arms 1124 of the release element to deflect radially-outward. Since the arms 1124 of the release element 1106 do not move radially-outward, the arms 1110 of the outer sleeve 1104 likewise do not move radially-outward, and the receiver member 200 remains securely coupled to the distal end of the instrument 1100. The force required for the release element 1106 to eject the bone anchor 400 from the receiver member 200 when the bone anchor is not fully seated in the receiver member can be less than the force required to splay the arms 1110 of the outer sleeve 1104 outward. Accordingly, if the bone anchor 400 is only partially seated within the receiver member 200, the release element 1106 can eject the bone anchor from the receiver member instead of releasing the receiver member from the instrument 1100.

The instrument 1100 can include a visual indicator to inform the user as to whether the bone anchor 400 is fully seated within the receiver member 200. For example, the release element 1106 can include a proximal extension (not shown) that is visible through a window formed in the outer sleeve 1104 or handle 1108 of the instrument 1100. The extension can be sized such that it is only visible through the window when the release element 1106 is displaced proximally by a fully-seated bone anchor 400. Accordingly, when the release element 1106 is visible through the window, it can indicate to the surgeon that the bone anchor 400 is fully-seated within the receiver member 200.

Unilateral Instruments

As noted above, the bone anchor assembly 100 can facilitate unilateral attachment of instruments thereto. In particular, a unilateral instrument can be attached to the receiver member 200 of the bone anchor assembly 100 at only one arm 202, 204 of the receiver member. Such attachment can provide a number of advantages. For example, unilateral instruments can have a lower profile such that they occupy less space within a retractor, cannula, or minimally-invasive working channel formed in the patient, or facilitate use with less retraction or smaller cannulas, reducing patient trauma. By way of further example, attachment to only one side of the receiver member 200 can leave the other side of the receiver member open for attachment of other instruments, can leave a clear path for lateral rod insertion, or can improve visualization of the anatomy or surgical site.

Unilateral instruments can be used to introduce a head, to apply countertorque, to slide a retractor blade down to a bone surface, to attach a fulcrum for compression or distraction, to introduce a set screw, to reduce a spinal rod (e.g., vertically, laterally, or both), or to perform various other surgical tasks.

FIGS. 12A-12F illustrate an exemplary unilateral attachment instrument 1200 that can be used with the bone anchor assembly 100 described above. As shown, the instrument 1200 can include an elongated body 1202 and a pivoting lock arm 1204.

The body 1202 can include proximal and distal ends 1202*p*, 1202*d* that define a longitudinal proximal-distal axis A10. The proximal end 1202*p* of the body 1202 can include a tube portion 1206 that is offset from the axis A10, such that a central axis A11 of the tube is coaxial with the central axis A1 of a bone anchor assembly 100 when the instrument 1200 is attached thereto. The tube 1206 can serve as an access channel or guide. For example, the tube 1206 can guide insertion of a driver instrument therethrough to engage the bone anchor 400 and drive the bone anchor into bone. The tube 1206 can be omitted, or can be replaced with a handle or other feature. The interior of the tube 1206 can include a thread, ratchet teeth, or other features for engaging instruments inserted therethrough. Such features can advantageously provide mechanical advantage when performing various tasks with the instrument 1200, such as rod reduction. The exterior of the tube 1206 can include flats 1222 or an annular groove 1224 for engaging the tube with another instrument, e.g., to apply a torque to the instrument, to attach the instrument to frame or other device, and so forth.

The lock arm 1204 can be pivotally coupled to the body 1202 such that the distal end of the lock arm 1204 can pivot radially-inward and radially-outward relative to the body. The lock arm 1204 can be pivotally coupled to the body 1202 by a pivot pin 1208. The pivot pin 1208 can be mounted at a point along the body 1202 that is intermediate the proximal and distal ends 1202*p*, 1202*d* of the body. The lock arm 1204 can include a release button 1210 for actuating the lock arm. The release button 1210 can be formed at a proximal end of the lock arm 1204 as shown, such that pressing the release button inward towards the body 1202 can cause the distal end of the lock arm to pivot radially-outward away from the body to a released position, and such that releasing the button can cause the distal end of the lock arm to pivot radially-inward towards the body to a locked position. The instrument 1200 can include a bias element 1212 to bias the lock arm 1204 towards the locked position or the released position. In the illustrated embodiment, a leaf spring 1212 is disposed within the body 1202 and configured to bias the lock arm 1204 towards the locked position.

Figure 12A:
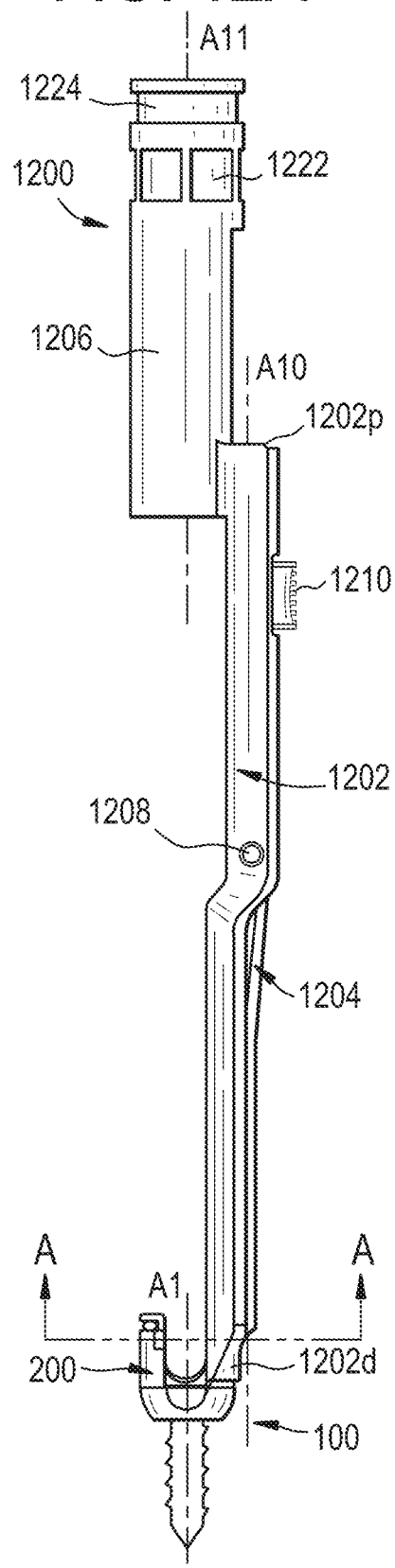
FIG. 12A is a front view of a unilateral attachment instrument.
Figure 12B:
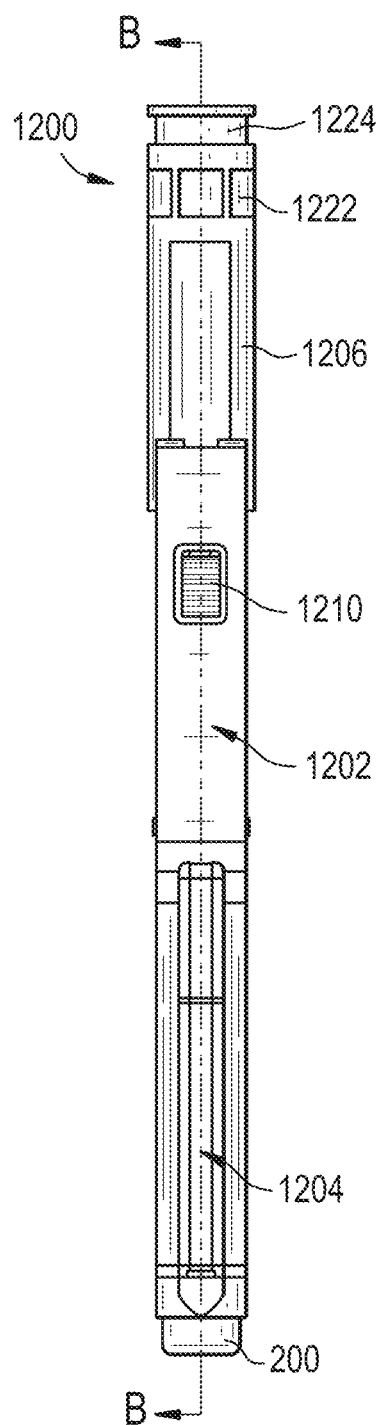
FIG. 12B is a side view of the instrument of FIG. 12A.
Figure 12E:
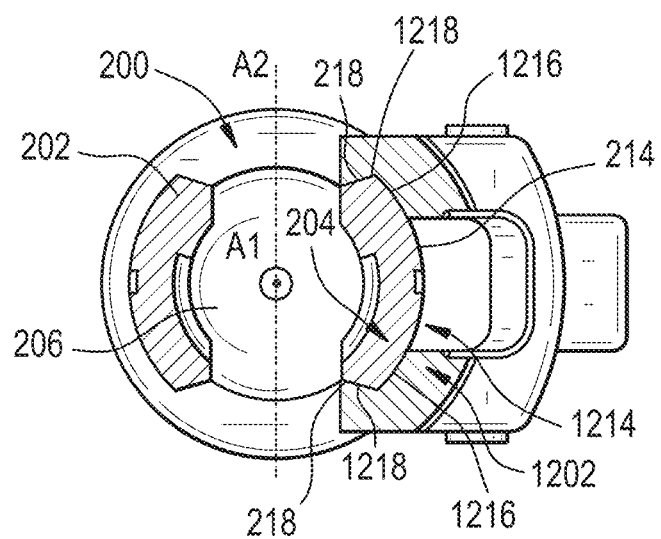
FIG. 12E is a sectional top view of the instrument of FIG. 12A coupled to a receiver member.

The distal end 1202*d* of the body 1202 can define a recess 1214 sized to receive an arm 202 or 204 of the receiver member 200 therein. The recess 1214 and the arm 204 can have cross-sectional shapes that are complementary to one another such that, when engaged to one another, the arm cannot rotate relative to the recess or translate laterally relative to the recess. The recess 1214 can be configured to grip or surround multiple sides of the arm 204 (e.g., at least two sides of the arm, at least three sides of the arm, at least four sides of the arm, etc.). As shown in FIG. 12E, the arm 204 and the recess 1214 can mate via a dovetail connection. The recess 1214 can define a curved face 1216 that forms a negative of the curved outer surface 214 of the arm 204. The recess 1214 can also define first and second planar faces 1218 that extend from the curved face 1216 and form a negative of the first and second engagement surfaces 218 of the arm 204. The first and second faces 1218 of the recess 1214 can extend at an oblique angle with respect to a plane defined by the proximal-distal axis A1 of the receiver member 200 and a central axis A2 of the rod-receiving recess 206. The first and second faces 1218 of the recess 1214 can be angled towards each other as the faces approach the proximal-distal axis A1 of the receiver member 200. As shown in FIG. 12E, the arm 204 can be received within or removed from the recess 1214 by translating the arm longitudinally with respect to the recess. The geometry of the recess 1214 and the arm 204, however, can prevent the arm from rotating relative to the instrument 1200 or from translating laterally with respect to the instrument when the arm is received in the recess 1214.

Figure 12F:
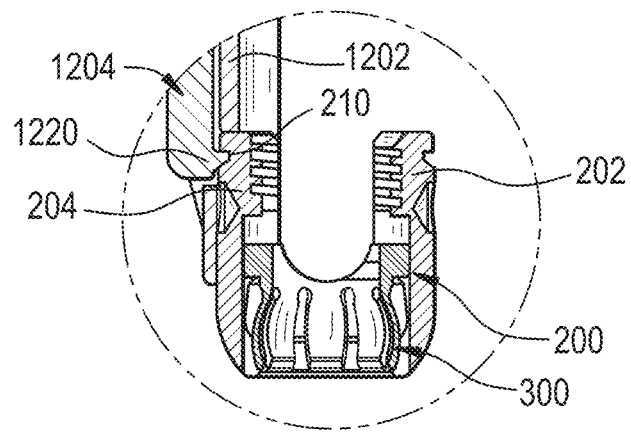
FIG. 12F is a sectional side view of the instrument of FIG. 12A coupled to a receiver member.

As shown in FIG. 12F, the distal end of the lock arm 1204 can include an engagement feature 1220 for preventing or limiting longitudinal movement of the instrument 1200 relative to the arm 204 of the receiver member 200. The engagement feature 1220 can include a shelf or ridge that projects radially-inward from the lock arm 1204 to selectively engage a corresponding arcuate groove 210 formed in the arm of the receiver member 200.

In use, an arm 202, 204 of the receiver member 200 can be inserted proximally into the recess 1214 and the lock arm 1204 can be engaged with the groove 210 formed in the arm. When coupled to the instrument 1200 in this manner, the receiver member 200 can be locked to the instrument, such that the receiver member cannot rotate or translate in any direction with respect to the instrument. The instrument 1200 can thus provide a stable platform for unilateral attachment to a receiver member or other head 200 of a bone anchor assembly 100.

Figure 12G:
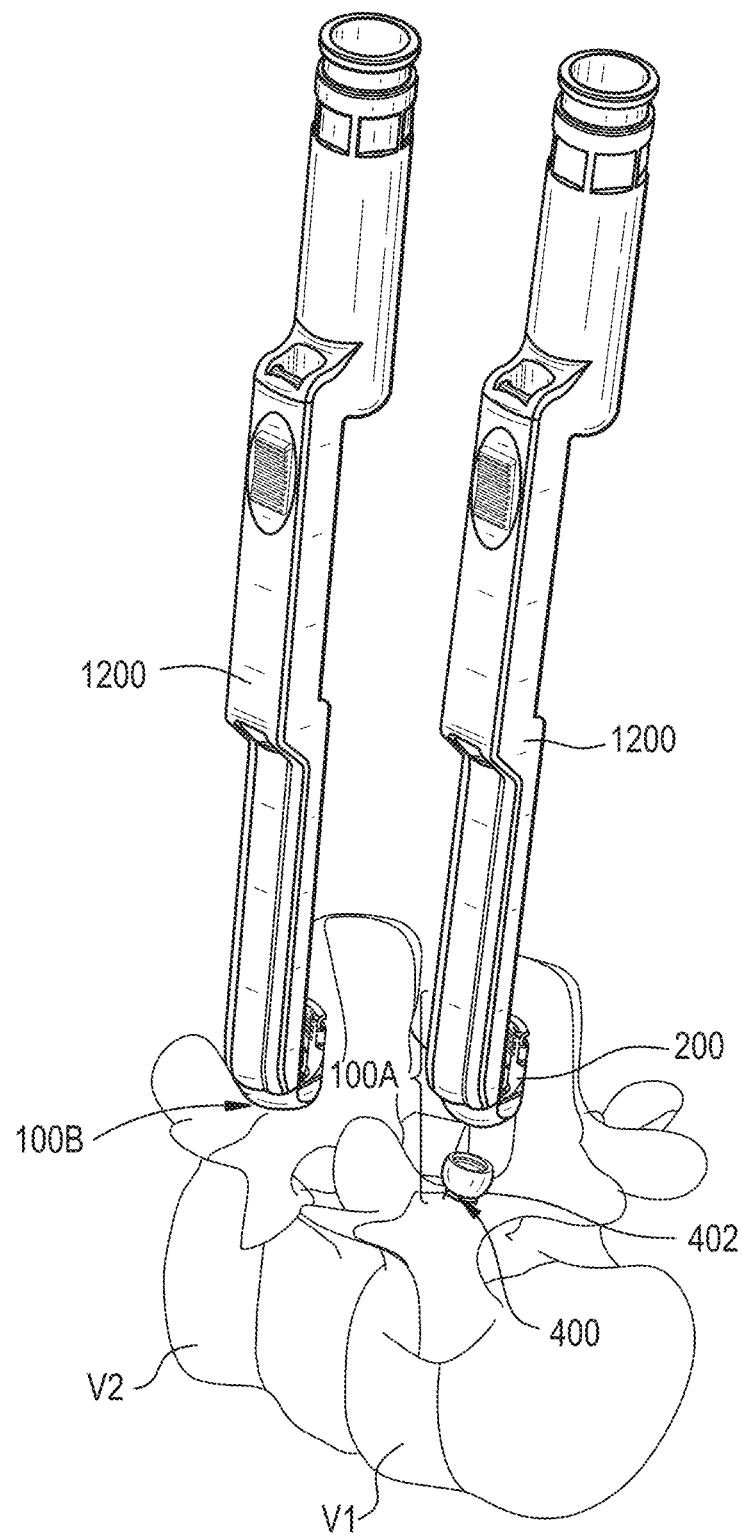
FIG. 12G is a perspective view of attaching a head to a bone anchor using the instrument of FIG. 12A.

A number of surgical steps can be facilitated by a unilateral attachment to the receiver head. FIG. 12G illustrates an exemplary method of using the unilateral attachment instrument 1200 to assemble a receiver member 200 to a bone anchor 400 previously implanted in a vertebra V1. The receiver member 200 can be attached to the instrument 1200 as described above, and then lowered distally onto the head 402 of the bone anchor 400. The user can apply a distal pushing force to the instrument 1200 to push the receiver member 200 onto the bone anchor 400 and form an assembled bone anchor assembly 100A. Once assembled, the instrument 1200 can be left in place, as shown with respect to a second bone anchor assembly 100B. Use of the unilateral attachment instrument 1200 can make it easier for the user to visualize the bone anchor 400 as the receiver member 200 is being advanced into the patient.

Figure 12H:
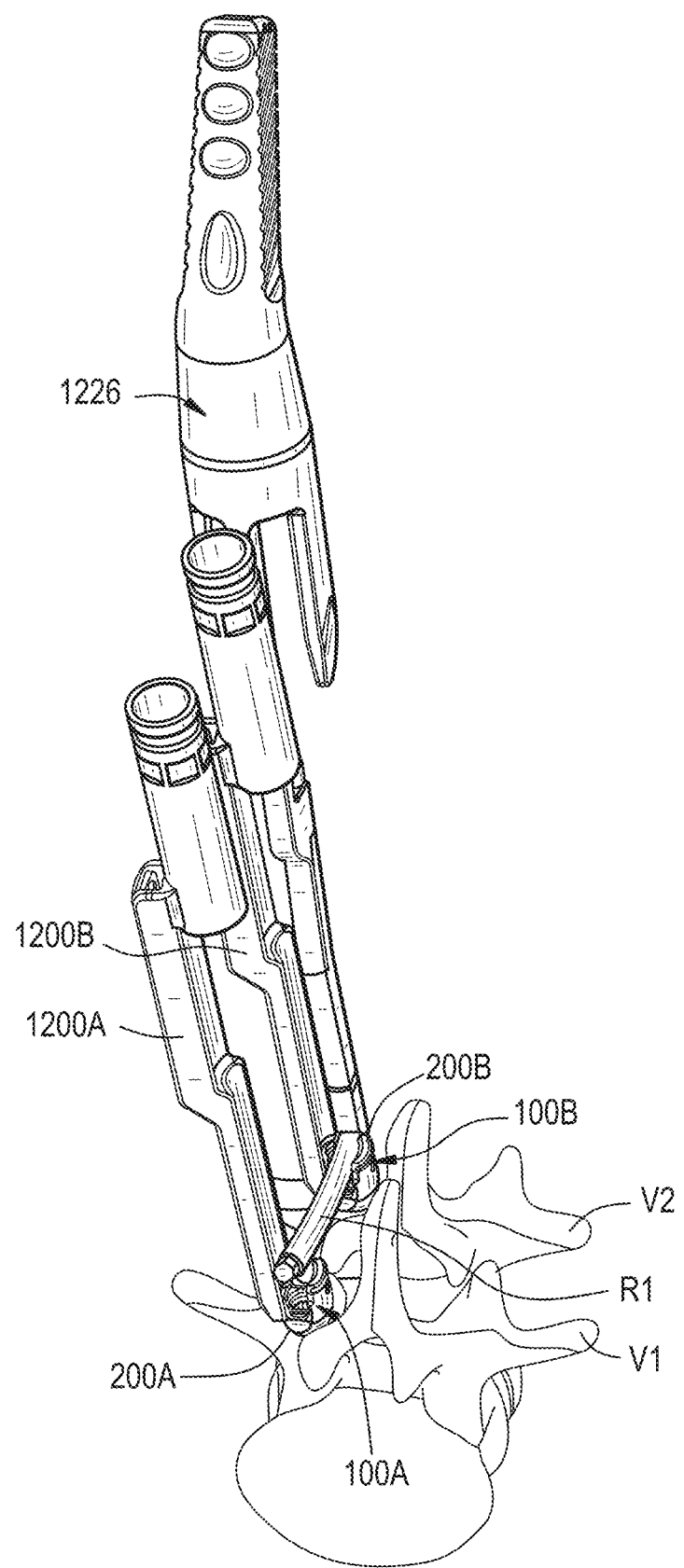
FIG. 12H is a perspective view of introducing a rod using the instrument of FIG. 12A.

FIG. 12H illustrates an exemplary method of using a unilateral attachment instrument in connection with introduction of a spinal rod. As shown, first and second bone anchor assemblies 100A, 100B can be implanted in respective first and second vertebrae V1, V2. Unilateral attachment instruments 1200A, 1200B can be coupled to each of the bone anchor assemblies 100A, 100B. A rod inserter 1226 can be used to introduce a spinal rod R1 coupled thereto into the rod receiving recesses of the bone anchor assemblies 100A, 100B. Introduction of the rod R1 can be facilitated by the use of the unilateral attachment instruments 1200A, 1200B, since one side of the receiver members 200A, 200B is left open such that motion of the rod into alignment with the recesses can include a lateral component. With a typical bilateral instrument, the motion of the rod would have to be limited to proximal-distal movement and longitudinal movement. In a typical MIS procedure with a bilateral instrument, the free end of the rod would need to be guided beneath the skin into the narrow channel between the opposed arms of the bilateral instrument. With a unilateral instrument, tunneling of the rod does not need to be as precise, since the rod can be moved laterally into alignment with the rod-receiving recess of the second bone anchor assembly.

Figure 12I:
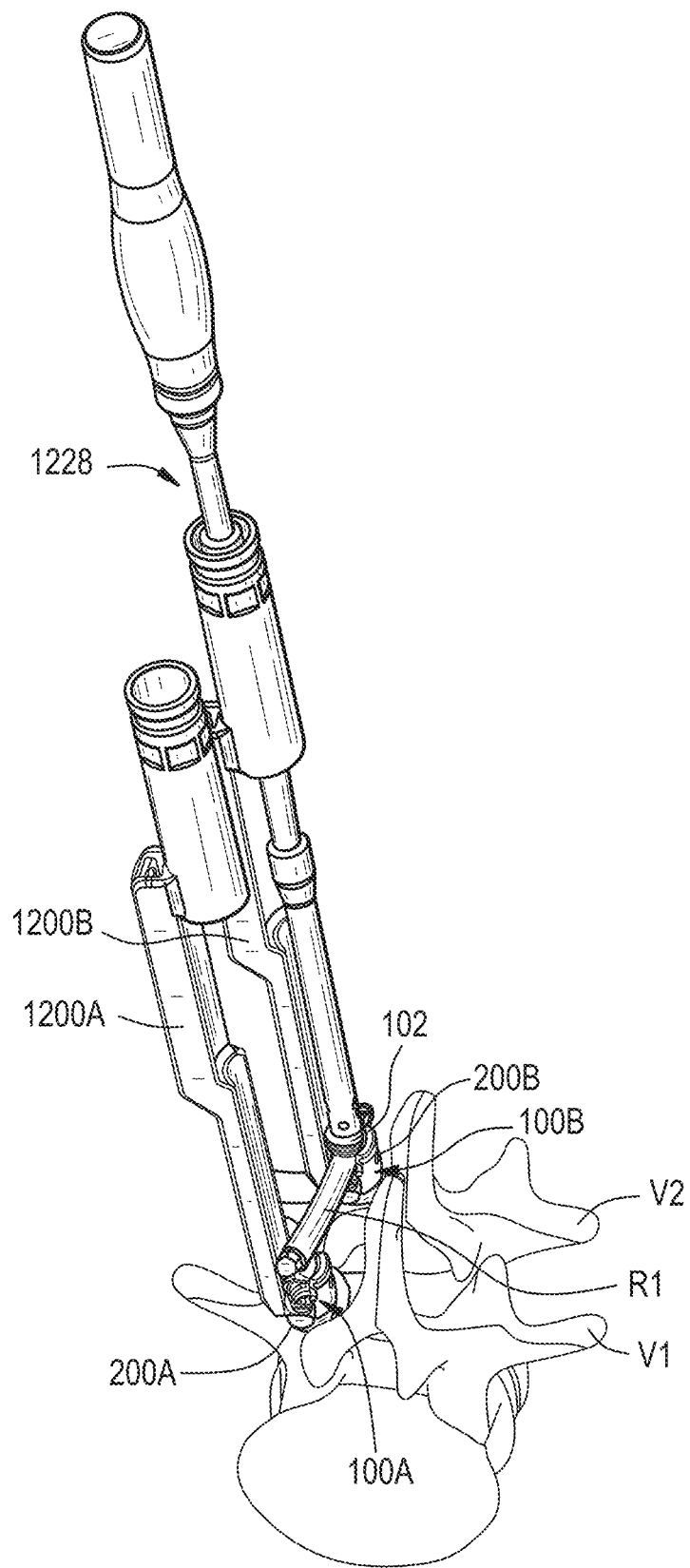
FIG. 12I is a perspective view of inserting a set screw using the instrument of FIG. 12A.

FIG. 12I illustrates an exemplary method of using a unilateral attachment instrument in connection with inserting a set screw. As shown, first and second bone anchor assemblies 100A, 100B can be implanted in respective first and second vertebrae V1, V2. Unilateral attachment instruments 1200A, 1200B can be coupled to each of the bone anchor assemblies 100A, 100B. A spinal rod R1 can be positioned in alignment with the rod-receiving recesses of the bone anchor assemblies 100A, 100B, for example using a rod introduction method of the type described above with respect to FIG. 12H. The instrument 1200B can guide insertion of a set screw 102 and a set screw driver instrument 1228. The driver shaft 1228 can be rotated within the instrument 1200B to thread the set screw 102 into or out of the receiver member 200B, e.g., for final tightening of a spinal rod R1 to the bone anchor assemblies 100A, 100B.

Figure 12J:
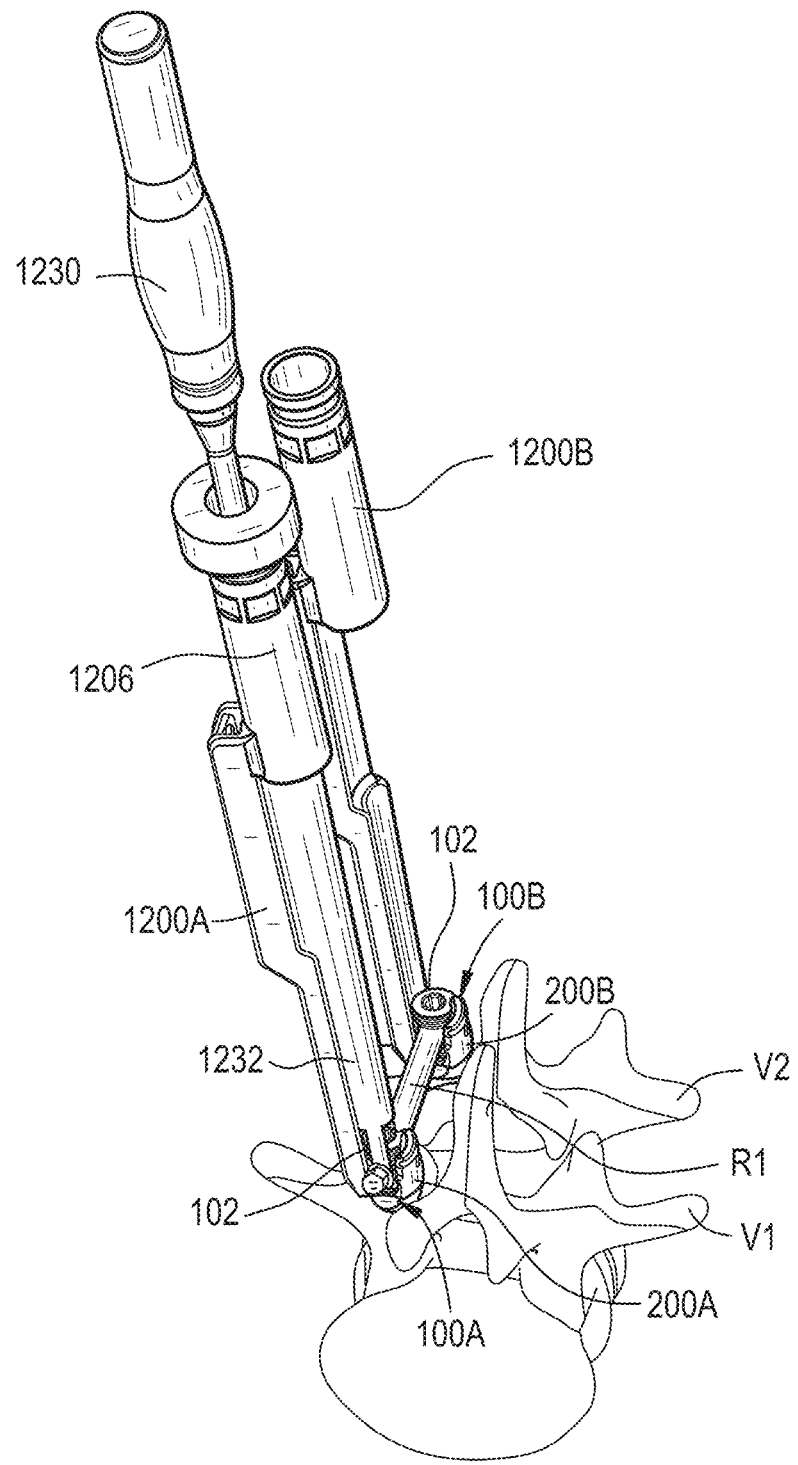
FIG. 12J is a perspective view of reducing a rod and inserting a set screw using the instrument of FIG. 12A.

FIG. 12J illustrates an exemplary method of using a unilateral attachment instrument in connection with reducing a spinal rod and inserting a set screw. Reduction of the rod R1 into the rod seats of the receiver members 200A, 200B can be achieved by inserting a reduction tool 1232 through a working channel of the unilateral attachment instrument 1200A. The tubular extension 1206 of the instrument 1200A can guide insertion of the reduction tool 1232. The reduction tool 1232 can be threadably engaged or otherwise coupled with the tubular extension 1206, such that the tool can be rotated within the tubular extension to reduce the rod R1. The reduction tool 1232 can define a working channel for guiding insertion of a set screw 102 and a set screw driver instrument 1230. The driver shaft 1230 can be rotated within the reduction tool 1232 to thread the set screw 102 into or out of the receiver member 200A, e.g., for final tightening of a spinal rod R1 to the bone anchor assemblies 100A, 100B.

Figure 12K:
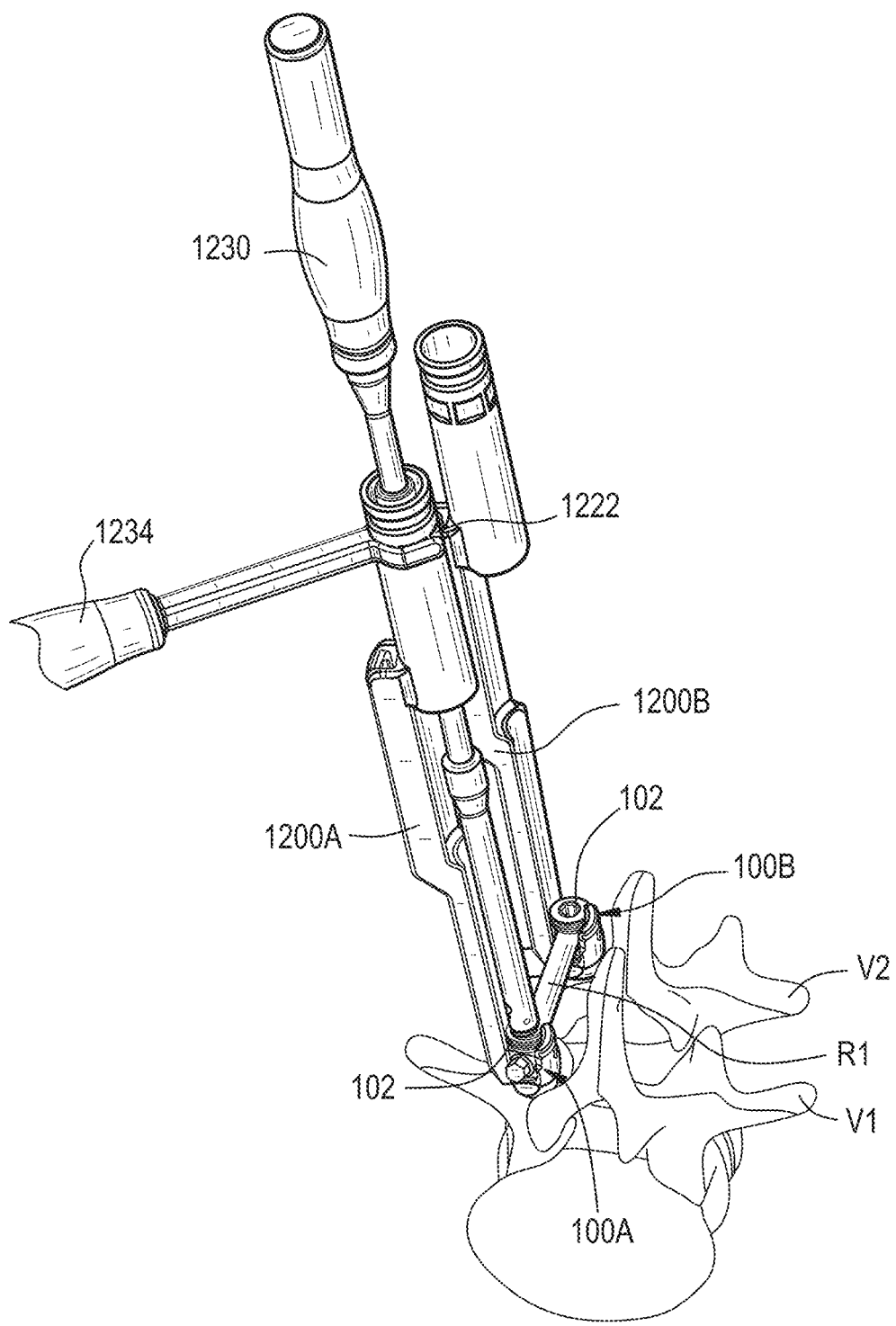
FIG. 12K is a perspective view of tightening a set screw and applying countertorque using the instrument of FIG. 12A.

As shown in FIG. 12K, the instrument 1200A can be used to apply countertorque when tightening or loosening the set screws 102. The instrument 1200A can include one or more flats 1222 at a proximal end of the instrument that can be gripped with an open-end wrench or other tool 1234 to provide a mechanical advantage to the user in applying a countertorque force to the instrument while the set screw driver 1230 is rotated within the instrument.

While not shown, it will be appreciated that the unilateral instrument can serve as a platform for any of a number of other surgical steps. For example, unilateral instruments can be used with a distraction device to distract first and second vertebrae. In particular, first and second instruments can be coupled to respective first and second bone anchor assemblies implanted respectively in the first and second vertebrae. The distraction device can be engaged with the instruments to apply a distraction force thereto, thereby distracting the vertebrae.

As another example, unilateral instruments can be used with a compression device to compress first and second vertebrae. In particular, first and second instruments can be coupled to respective first and second bone anchor assemblies implanted respectively in the first and second vertebrae. The compression device can be engaged with the instruments to apply a compression force thereto, thereby compressing the vertebrae.

As another example, unilateral instruments can be used to perform a derotation maneuver. In particular, first and second instruments can be coupled to respective first and second bone anchor assemblies implanted respectively in first and second vertebrae. The first and second instruments can be pushed in opposite directions to rotate one vertebra with respect to the other vertebra. The instruments can include features for coupling the instruments to a derotation frame.

Bone Anchor Assemblies with Inserts

FIGS. 13A-13K illustrate an exemplary embodiment of a bone anchor assembly 1300. Except as indicated below and as will be readily appreciated by a person having ordinary skill in the art in view of the present disclosure, the structure and operation of the bone anchor assembly 1300 is substantially the same as that of the bone anchor assembly 100 described above. For example, the bone anchor assembly 1300 can include a collet 300, a shank or bone anchor 400, and a closure mechanism or set screw 102, all of the type described above. The bone anchor assembly 1300 can also include a receiver member 200' which can be similar to the receiver member 200 described above, but can include a separate retaining ring or insert 1302. During assembly, the collet 300 can be inserted into the receiver member 200' and, thereafter, the insert 1302 can be secured to the receiver member to retain the collet within the receiver member. Use of a separate insert 1302 can allow the collet 300 to be assembled to the receiver member 200' without deforming or deflecting the fingers 316 of the collet 300 as the collet is loaded into the receiver member. This can advantageously reduce the risk of the collet fingers 316 being damaged during assembly.

The insert 1302 can be a ring-shaped body having an inner surface, an outer surface, and a central opening extending therethrough. The central opening can be large enough to allow the head 402 of the shank 400 to pass therethrough along the axis A1, but small enough to prevent the collet 300 from passing distally through the insert 1302. The central opening of the insert 1302 can have a diameter that is less than a resting outer diameter of the fingers 316 of the collet 300.

The insert 1302 can be secured to the receiver member 200' in various ways. For example, as shown in FIGS. 13A-13F, the outer surface of the insert 1302 can include a ridge 1304 that extends radially-outward therefrom. An inner surface of the receiver member 200' can include a counterpart groove 1306 in which the ridge 1304 can be received to secure the insert 1302 to the receiver member. When the ridge 1304 is received within the groove 1306, the insert 1302 can be prevented from moving proximally or distally along the axis A1 relative to the receiver member 200'. The insert 1302 can be radially-expandable and/or radially-collapsible to facilitate insertion of the ridge 1304 into the groove 1306 during assembly. For example, the insert 1302 can include a cut 1308 such that the insert forms a C-clip as shown. In other arrangements, the insert 1302 can include one or more slits, webbed portions, or other features for allowing expansion and/or contraction of the insert. It will be appreciated that the positioning of the ridge 1304 and the groove 1306 can be reversed, such that the groove is formed in the insert 1302 and the ridge is formed in the receiver member 200'. While a continuous circumferential ridge 1304 and groove 1306 are shown, in other arrangements the insert 1302 can include one or more discrete projections configured to be received within a corresponding one or more discrete pockets of the receiver member 200' to retain the insert therein.

Figure 13C:
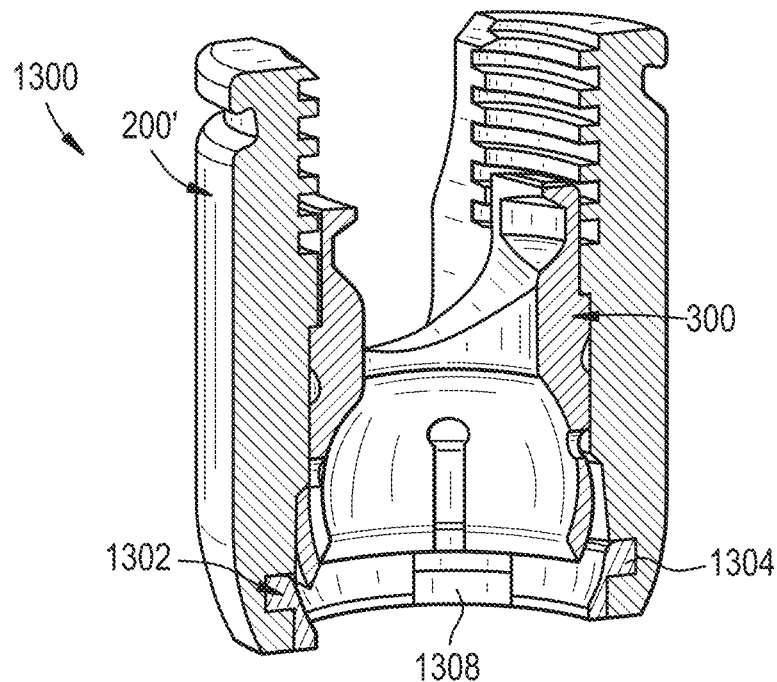
FIG. 13C is a sectional perspective view of the bone anchor assembly of FIG. 13A.
Figure 13D:
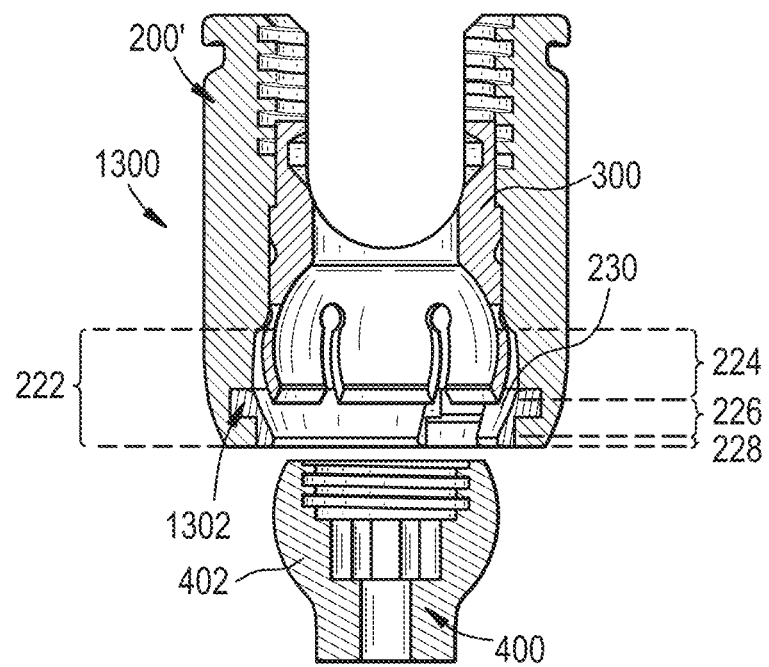
FIG. 13D is a sectional side view of the bone anchor assembly of FIG. 13A.
Figure 13E:
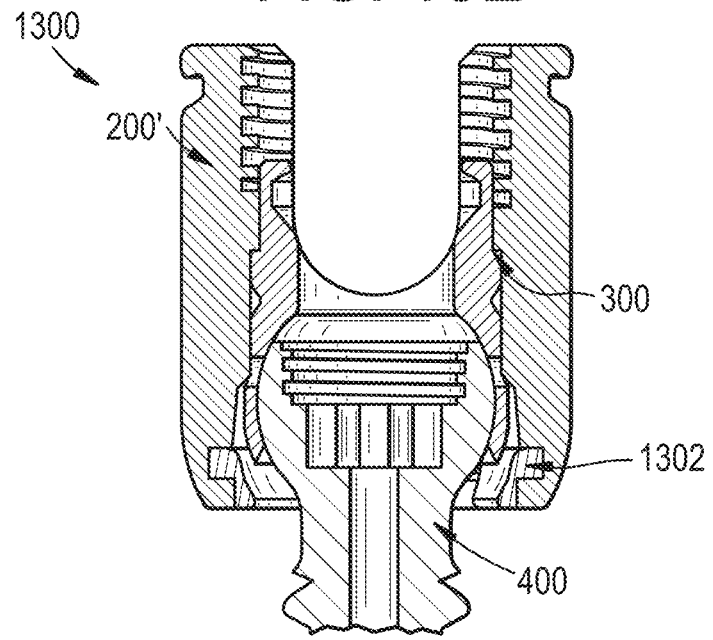
FIG. 13E is a sectional side view of the bone anchor assembly of FIG. 13A with a shank of the bone anchor inserted into the receiver member.
Figure 13F:
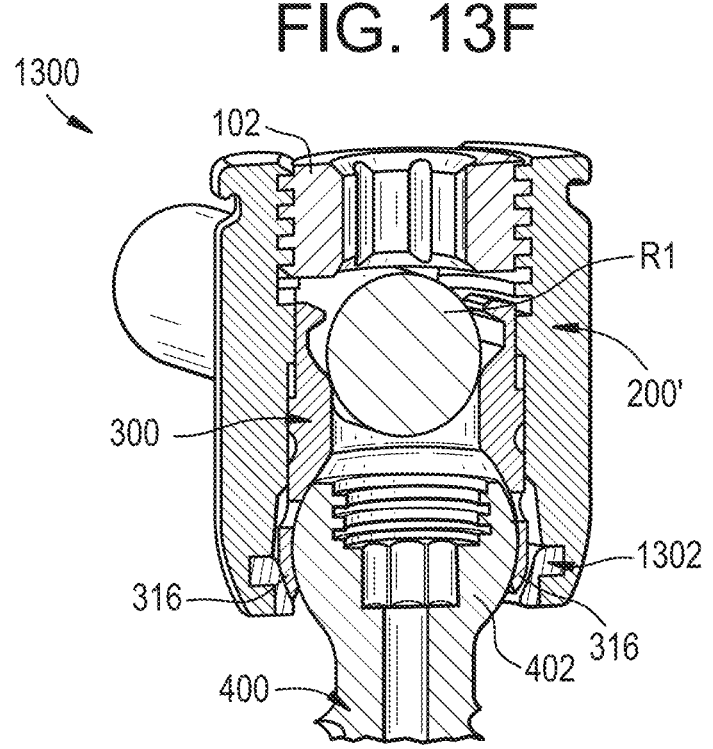
FIG. 13F is a sectional perspective view of the bone anchor assembly of FIG. 13A with a rod secured to the bone anchor assembly by a set screw.
Figure 13G:
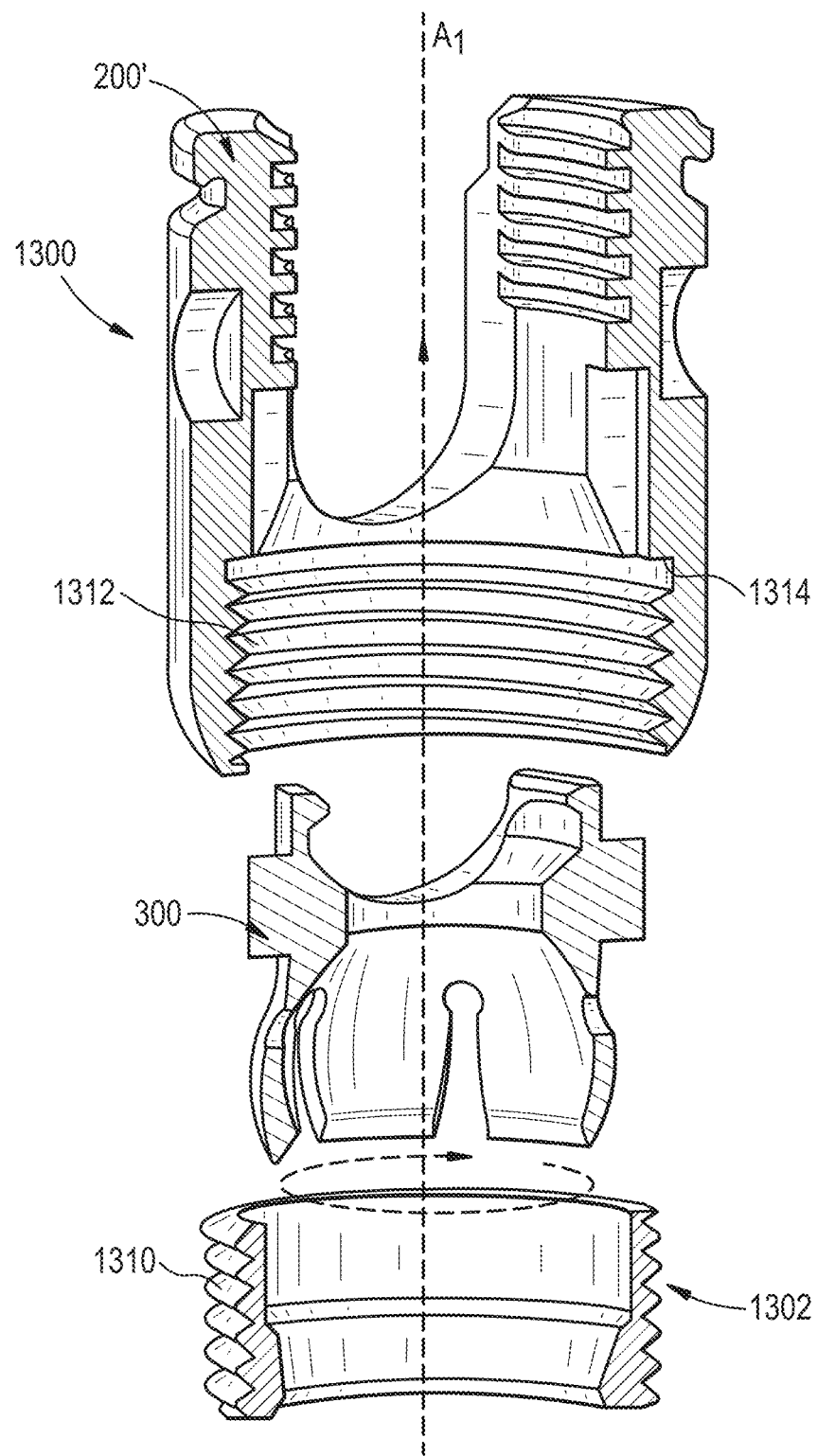
FIG. 13G is a sectional exploded perspective view of the bone anchor assembly of FIG. 13A, shown with a threaded insert.
Figure 13H:
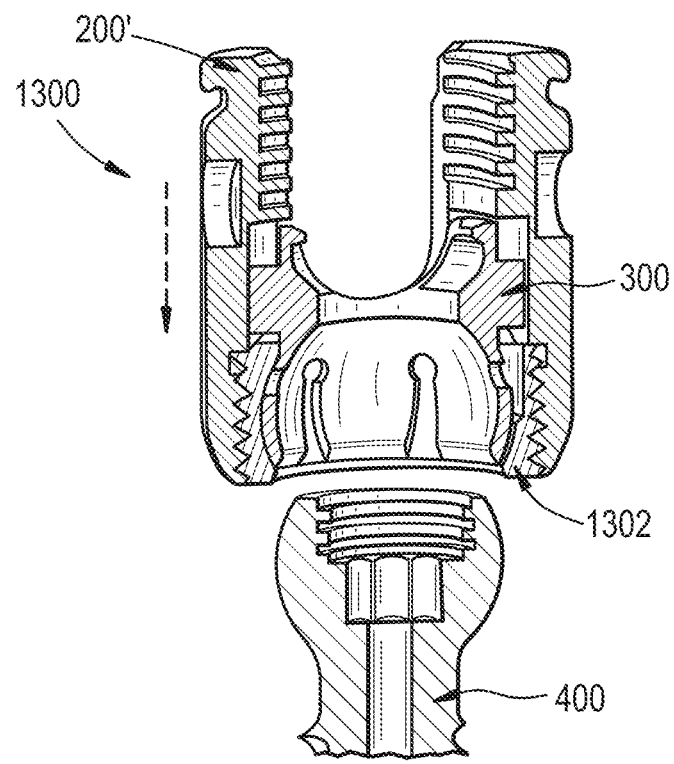
FIG. 13H is a sectional perspective view of the bone anchor assembly of FIG. 13G.
Figure 13I:
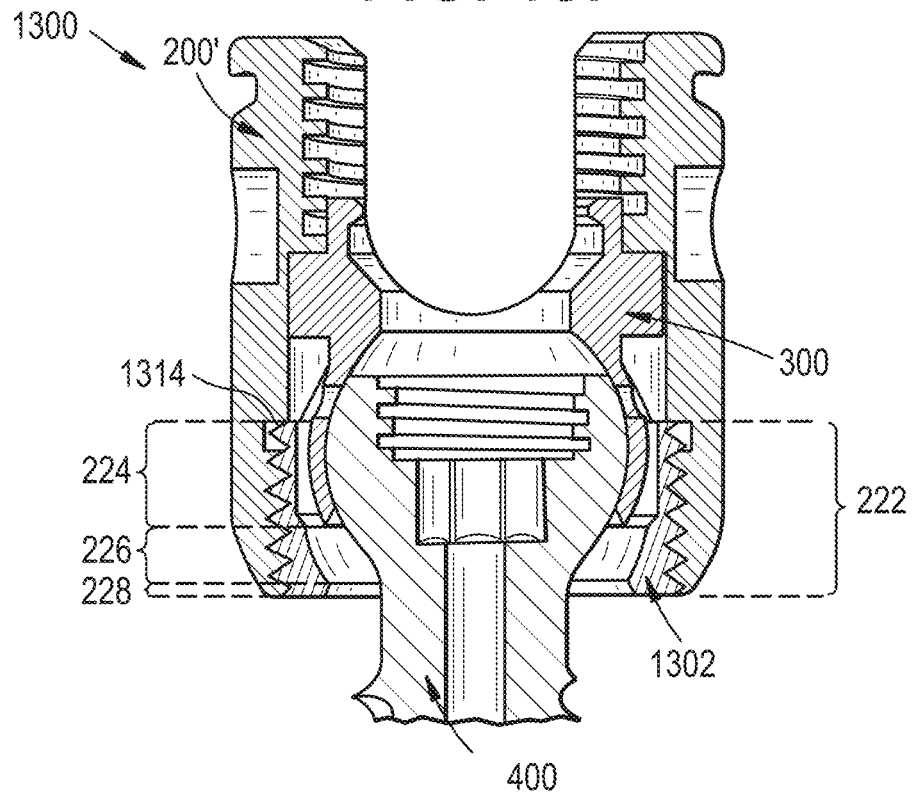
FIG. 13I is a sectional side view of the bone anchor assembly of FIG. 13G with a shank of the bone anchor assembly inserted into the receiver member.
Figure 13J:
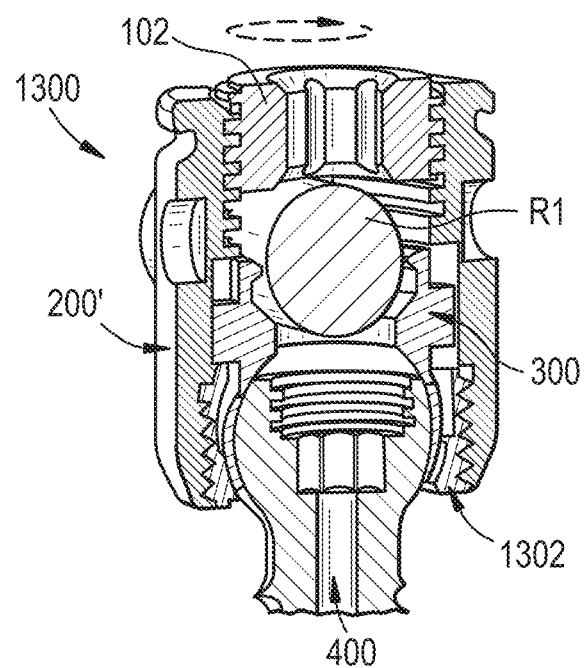
FIG. 13J is a sectional perspective view of the bone anchor assembly of FIG. 13G with a rod secured to the bone anchor assembly by a set screw.
Figure 13K:
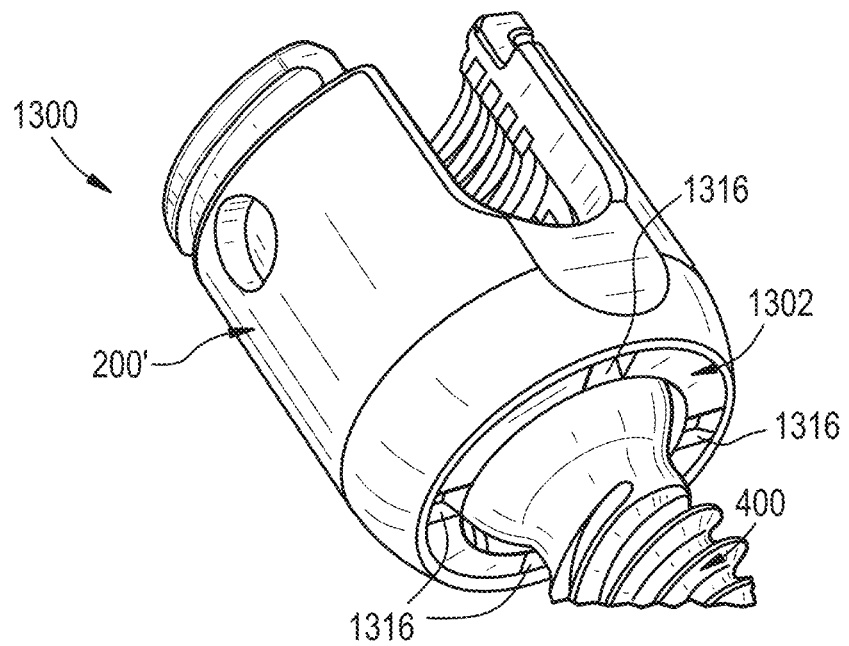
FIG. 13K is a perspective view from below of the bone anchor assembly of FIG. 13G.

As another example, as shown in FIGS. 13G-13K, the outer surface of the insert 1302 can include a thread 1310 that engages with a corresponding thread 1312 formed in the inner surface of the receiver member 200'. Accordingly, rotation of the insert 1302 about the axis A1 relative to the receiver member 200' can be effective to advance or retract the insert into the receiver member along the axis A1. In some embodiments, the insert 1302 can be threadably advanced into the receiver member 200' until a proximal end of the insert contacts and bears against a distal-facing shoulder 1314 formed in the receiver member. A distal-facing surface of the insert 1302, e.g., at the terminal distal end of the insert, can include a drive feature 1316 to facilitate application of torque to the insert. In one arrangement, as shown in FIG. 13K, the drive feature can be one or more female recesses 1316 sized to receive a corresponding male drive feature of a driver instrument. In other arrangements, the drive feature can be a male drive feature that projects distally from the insert 1302. The male drive feature can be configured to break off from the insert 1302 when a pre-determined threshold force, e.g., a predetermined threshold torque, is applied thereto. Accordingly, the insert 1302 can be tightened to the receiver member 200' until the male drive feature breaks off, indicating to the user that the insert is tightened sufficiently and, optionally, preventing subsequent removal of the insert from the receiver member.

While threaded and snap-ring engagements are shown for attaching the insert 1302 to the receiver member 200', it will be appreciated that any of a variety of other attachment types can be used instead or in addition, such as swaging, staking, gluing, welding, and so forth.

Some or all of the working surfaces of the cavity 222 of the receiver member 200' can be defined by the insert 1302. In FIGS. 13A-13F, the upper portion 224 of the cavity 222 is defined partially by the receiver member 200' and partially by the insert 1302. In particular, the frustoconical or substantially frustoconical part of the upper portion 224 is formed by the receiver member 200' and the spherical or substantially spherical seat 230 is formed by the insert 1302. The middle and lower portions 226, 228 of the cavity 222 are defined by the insert 1302. In FIGS. 13G-13K, the upper, middle, and lower portions 224, 226, 228 of the cavity 222 are all defined by the inner surface of the insert 1302.

As noted above, the bone anchor assembly 1300 can be assembled by loading the collet 300 into the distal end of the receiver member 200' and then attaching the insert 1302 to the receiver member to retain the collet therein. Once assembled, use of the bone anchor assembly 1300 can be substantially the same as that of the bone anchor assembly 100 described above. As shown in FIGS. 13D and 13H, the head 402 of the shank 400 can be loaded into the distal end of the insert 1302 and passed proximally therethrough into the receiver member 200'. An axial force can be applied to the receiver member 200', causing the head 402 of the shank 400 to push the collet fingers 316 into the upper portion 224 of the cavity 222, where the collet fingers are allowed to radially expand and allow passage of the head of the shank into the collet, as shown in FIGS. 13E and 13I. The collet fingers 316 can constrain the shank head 402 within the receiver member 200'. Diametrical interference between the shank head 402 and the collet fingers 316 inner sphere can create drag between the two components, e.g., for provisional positioning of the bone anchor assembly 1300 and to prevent flopping. A rod R1 and a set screw 102 can be installed into the receiver member 200' as shown in FIGS. 13F and 13J. Subsequent rotation of the set screw 102 can draw the receiver member 200' upward relative to the rod R1 and the collet 300, thereby wedging the collet fingers 316 between the shank head 402 and the insert 1302. The insert 1302 and the collet fingers 316 can be configured to constrain the shank head 402 in the receiver member 200', thereby creating a polyaxial locking mechanism. The insert 1302 inner surface can be spherical to accept collet fingers 316 with an outer spherical shape to facilitate remobilization of polyaxial motion upon set screw removal.

Bone Anchor Assemblies with Compression Caps

FIGS. 14A-14K illustrate an exemplary embodiment of a bone anchor assembly 1400. Except as indicated below and as will be readily appreciated by a person having ordinary skill in the art in view of the present disclosure, the structure and operation of the bone anchor assembly 1400 is substantially the same as that of the bone anchor assemblies 100, 1300 described above. For example, the bone anchor assembly 1400 can include a receiver member 200' with a retaining ring or insert 1302, a shank or bone anchor 400, and a closure mechanism or set screw 102, all of the type described above. The bone anchor assembly 1400 can also include a multi-component collet 300'. The collet 300' can include a compression cap 1402 and a collet ring 1404. The compression cap 1402 can be axially-translatable relative to the collet ring 1404. The compression cap 1402 can contact and bear against the spherical head 402 of the shank 400 when the construct is tightened (e.g., when a spinal rod R1 is secured to the bone anchor assembly 1400 by a set screw 102). Thus, when the construct is locked, resistance to polyaxial movement of the shank 400 relative to the receiver member 200' can be provided at both (i) distal portions of the shank head 402 via wedged collet fingers 316 and (ii) proximal portions of the shank head via the compression cap 1402. The compression cap 1402 can provide a load path that bears down onto the proximal-most portion of the shank head 402, which may provide increased poly-slip performance as compared to a load path that runs exclusively through the collet fingers 316. The compression cap 1402 can also augment the resistance to polyaxial movement provided by the wedged collet fingers 316 by increasing the surface area of the collet 300' that is in contact with the shank head 402. The illustrated arrangement may provide enhanced poly-slip performance as compared to arrangements that employ only a compression cap, as the wedged collet fingers 316 can provide locking that is more consistent and largely independent of the angle of the shank 400 relative to the receiver member 200'.

During assembly, the collet 300' can be inserted into the receiver member 200' and, thereafter, the insert 1302 can be secured to the receiver member to retain the collet within the receiver member. Use of a separate insert 1302 can allow the collet 300' to be assembled to the receiver member 200' without deforming or deflecting the fingers 316 of the collet 300' as the collet is loaded into the receiver member. This can advantageously reduce the risk of the collet fingers 316 being damaged during assembly.

The bone anchor assembly 1400 can be modular such that any of a variety of heads 200' can be coupled to any of a variety of bone anchors 400, and such that the assembly 1400 can be fit together in situ. The bone anchor 400 can be bottom loaded into the receiver member 200' and can be captured by the collet 300' to retain the bone anchor within the receiver member while still allowing relative motion therebetween. The set screw 102 can be tightened to wedge the collet 300' between the head 402 of the bone anchor 400 and the receiver member 200', and to urge the compression cap 1402 onto the head of the bone anchor, thereby locking the relative position of the bone anchor and the receiver member. The set screw 102 can also be effective to lock a spinal rod R1 or other implant to the bone anchor assembly 1400.

In use, the bone anchor 400 can be driven into bone without the head 200' being attached thereto. This can result in a lower profile initial construct and allow the bone anchor 400 to be placed before other steps of the procedure are performed, such as exposing the neural elements, removing the facets and disc for fusion, and so forth. As a result, anatomical reference points can be preserved and can be used when targeting bone anchor 400 insertion. Also, the lower profile can provide more access to the surgical site for the user. The bone anchor 400 can also be used as a platform for other manipulations, such as distraction, compression, derotation, soft tissue retraction, and the like. The assembly 1400 can also be implanted in the patient in a pre-assembled state.

Figure 14C:
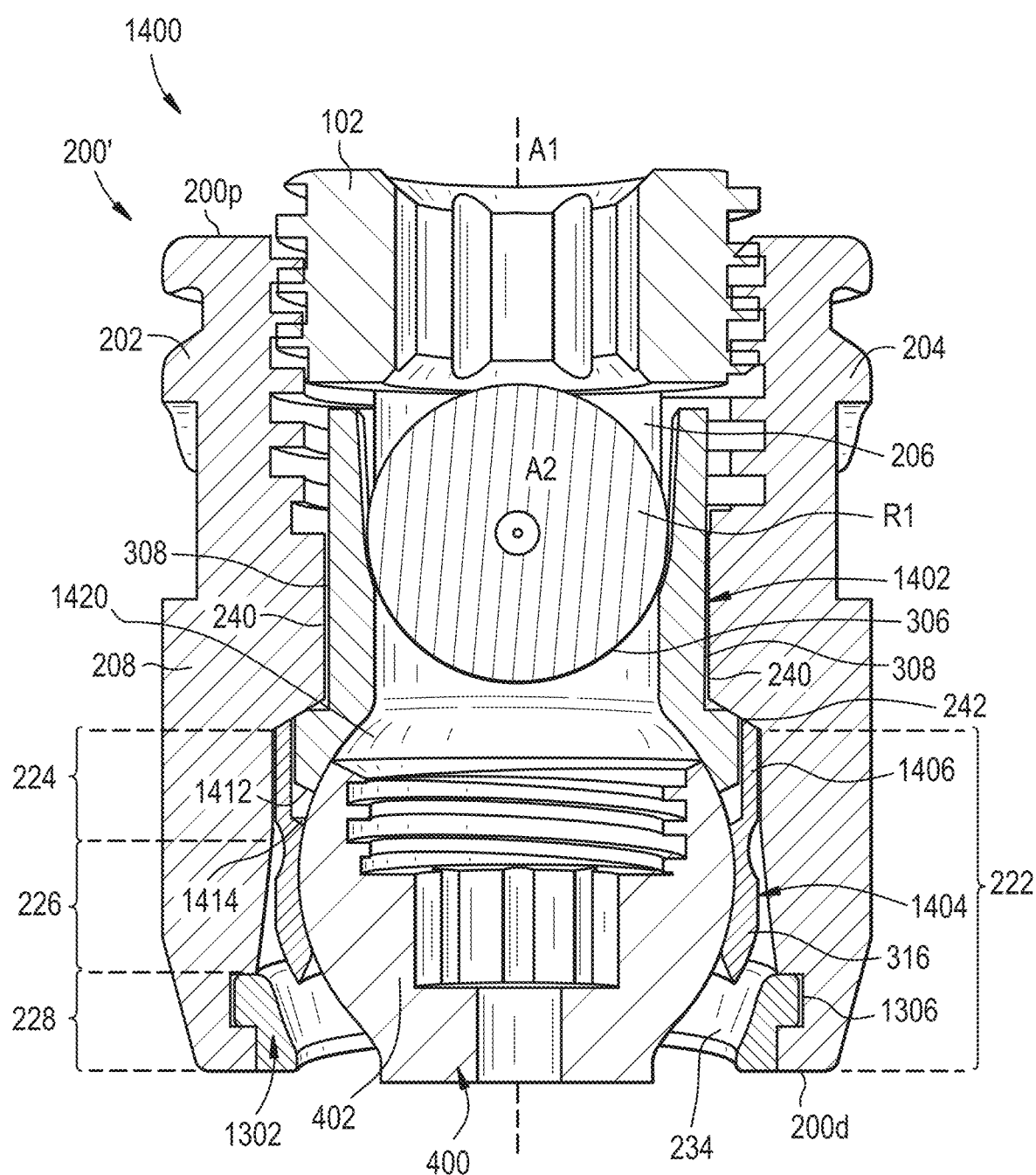
FIG. 14C is a sectional side view of the bone anchor assembly and spinal rod of FIG. 14A.
Figure 14D:
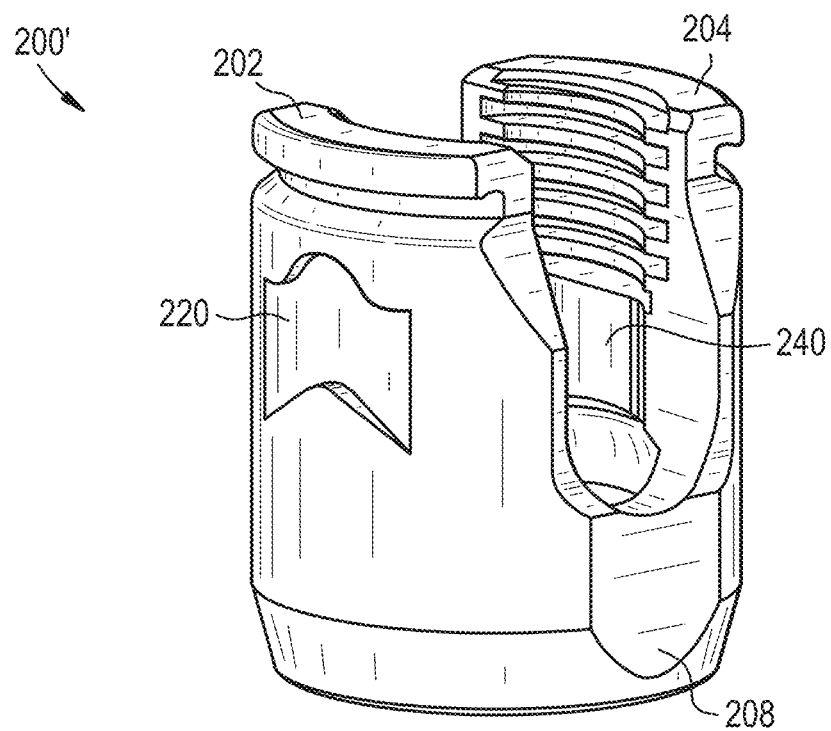
FIG. 14D is a perspective view of a receiver member of the bone anchor assembly of FIG. 14A.
Figure 14E:
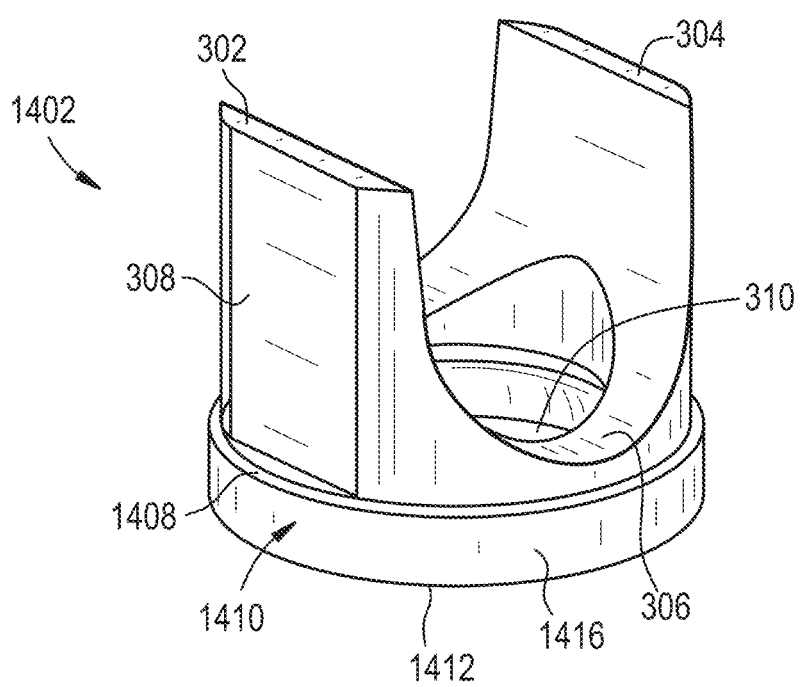
FIG. 14E is a perspective view of a compression cap of the bone anchor assembly of FIG. 14A.

FIGS. 14C and 14D illustrate the head or receiver member 200' in detail. The receiver member 200' can include proximal and distal ends 200p, 200d that define a central proximal-distal axis A1. The proximal end 200p of the receiver member 200' can include a pair of spaced apart arms 202, 204 that define a rod-receiving recess 206 therebetween. The rod-receiving recess 206 can have a central axis A2. The rod-receiving recess 206 can be open in a proximal direction, such that a rod R1 can be inserted into the recess by moving the rod distally with respect to the receiver member 200'. The inner surfaces of each of the arms 202, 204 can be configured to mate with the set screw 102. For example, the inner surfaces of the arms 202, 204 can include threads that correspond to external threads formed on the set screw 102. Accordingly, rotation of the set screw 102 with respect to the receiver member 200' about the axis A1 can be effective to translate the set screw with respect to the receiver member axially along the axis A1. Each of the arms 202, 204 can extend from a base portion 208 of the receiver member 200' to a free end.

The arms 202, 204 can include features, such as recesses, dimples, notches, projections, or the like, to facilitate coupling of the receiver member 200' to various instruments. For example, as described above with respect to the receiver member 200, the receiver member 200' can include a "top notch" feature and/or a unilateral attachment feature. Alternatively, or in addition, the receiver member 200' can include a blind hole, through hole, recess, or opening 220 formed in an exterior sidewall thereof, e.g., for engagement with a corresponding projection of an instrument, such as a rocker fork reduction instrument, to facilitate coupling of the instrument to the receiver member 200'. In the illustrated arrangement, a "bow-tie" type recess 220 is formed in each of the arms 202, 204 of the receiver member 200'.

The base portion 208 of the receiver member 200' can define an interior cavity 222 in which the collet 300' and the head 402 of the bone anchor 400 can be received. While any of a variety of cavity shapes can be used, the illustrated cavity 222 includes an upper, proximal portion 224, a middle portion 226, and a lower, distal portion 228, as shown in FIG. 14C.

The upper portion 224 of the cavity 222 can be cylindrical or substantially cylindrical about the axis A1. The upper portion 224 of the cavity can receive a proximal body portion 1406 of the collet ring 1404 in a snug fit. For example, the upper portion 224 of the cavity can have an inside diameter that is closely matched to the outside diameter of the proximal body portion 1406 of the collet ring 1404, e.g., +/−5%. This can limit or prevent "slop" in the assembly 1400 prior to locking and can help resist toggle or deformation of the collet 300' within the receiver member 200', before, during, or after locking. In some embodiments, a cylinder-to-cylinder contact or constraint can be formed between the collet ring 1404 and the upper portion 224 of the cavity 222. The middle portion 226 of the cavity can be frustoconical or substantially frustoconical about the axis A1. The middle portion 226 of the cavity can provide a relief zone to accommodate radially-outward expansion of the collet fingers 316 when the head 402 of the shank 400 is introduced into the collet ring 1404. The lower portion 228 of the cavity 222 can include a spherical or substantially spherical seat 234 that faces in a proximal direction. The seat 234 can form a bearing surface against which the collet fingers 316 can be wedged when the assembly 1400 is locked. In some embodiments, the seat 234 can be conical and/or tapered. The cavity 222 can be entirely defined by interior surfaces of a unitary or monolithic receiver member or, as shown, at least a portion of the cavity can be defined by a retaining ring or insert 1302 that is separate from the receiver member 200'. In the illustrated arrangement, the spherical seat 234 is defined by the interior surface of the retaining ring 1302.

The receiver member 200' can include features for restricting or preventing motion of the collet 300' with respect to the receiver member. For example, the receiver member 200' can include features for limiting proximal-distal travel of the collet 300', or for limiting or preventing rotation of the collet. In the illustrated embodiment, the receiver member 200' includes diametrically-opposed flats 240 that engage corresponding flats 308 of the compression cap 1402 to prevent rotation of the compression cap relative to the receiver member. This can help ensure that a rod slot 306 of the compression cap 1402 remains aligned with the rod slot 206 of the receiver member 200'. The illustrated anti-rotation feature may be easier to manufacture than the keyway and wing arrangement described above, though in some embodiments the bone anchor assembly 1400 can include a keyway and wing arrangement. The flats 240 can allow the compression cap 1402 to translate along the axis A1 with respect to the receiver member 200' while restricting or preventing rotation of the compression cap about the axis A1 with respect to the receiver member. Proximal travel of the compression cap 1402 within the receiver member 200' can be limited by engagement between a proximal-facing surface 1408 of the compression cap and a distal-facing shoulder 242 formed at the roof of the cavity 222. The shoulder 242 can also limit proximal travel of the collet ring 1404 within the receiver member 200'. The shoulder 242 can be obliquely angled with respect to the central axis A1, which can facilitate manufacturing of the receiver member 200' by allowing the shoulder 242 to be machined with a pointed-tip drill bit. The obliquely-angled shoulder 242 can also allow more material to be retained when manufacturing the receiver member 200', thickening the sidewall of the receiver member in an area that may be important for resisting splaying of the receiver member arms 202, 204 when the set screw 102 is tightened.

Figure 14F:
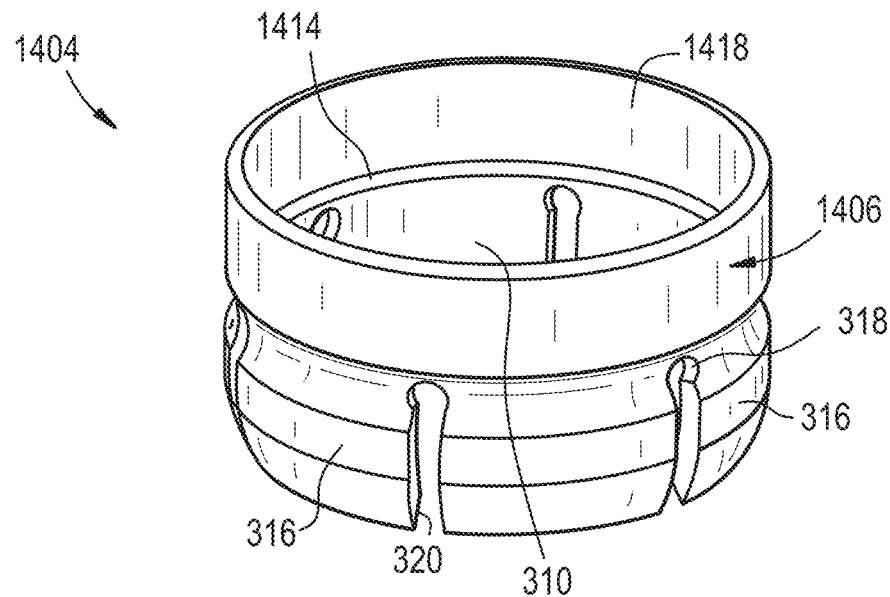
FIG. 14F is a perspective view of a collet ring of the bone anchor assembly of FIG. 14A.

The collet 300' can include a compression cap 1402 (shown in detail in FIG. 14E) and a collet ring 1404 (shown in detail in FIG. 14F). The compression cap 1402 can be movably-coupled to the collet ring 1404. For example, the compression cap 1402 can be telescopically-received within a central opening of the collet ring 1404. The compression cap 1402 and the collet ring 1404 can be positioned within the cavity 222 formed in the receiver member 200'. The compression cap 1402 and the collet ring 1404 can be independently longitudinally translatable within the cavity 222, along the axis A1. The compression cap 1402 can be rotatable relative to the collet ring 1404 about the axis A1. The compression cap 1402 can be limited or prevented from rotating relative to the collet ring 1404 about the axis A1. For example, the compression cap 1402 and the collet ring 1404 can include interlocking ridge and groove features to limit rotation therebetween while still allowing relative axial translation.

The compression cap 1402 can be generally cylindrical with first and second arms 302, 304 extending in a proximal direction to respective free ends of the arms. The first and second arms 302, 304 can be aligned with the first and second arms 202, 204 of the receiver member 200' such that a recess 306 defined therebetween is aligned with the rod-receiving recess 206. Accordingly, the rod R1 can be simultaneously cradled between the arms 302, 304 of the compression cap 1402 and the arms 202, 204 of the receiver member 200' when the rod is disposed in the rod-receiving recess 206.

The compression cap 1402 can include a mating feature configured to limit or prevent certain movement of the compression cap with respect to the receiver member 200'. For example, the compression cap 1402 can include opposed flats 308 formed in the outer surfaces of the arms 302, 304. The flats 308 can be aligned with and can contact the corresponding flats 240 described above to allow the compression cap 1402 to translate within the receiver member 200' but to limit or prevent rotation of the compression cap 1402 relative to the receiver member. While multiple flats 308 are shown, the compression cap 1402 can include only a single flat in some embodiments or can include more than two flats.

The compression cap 1402 can include a radial projection 1410. The projection 1410 can be formed at or adjacent to a distal end of the compression cap 1402. The projection 1410 can define a proximal-facing shoulder 1408 for contacting the shoulder 242 of the receiver member 200' to limit proximal translation of the compression cap 1402 relative to the receiver member along the axis A1. The proximal-facing shoulder 1408 can be obliquely angled with respect to the axis A1. For example, the proximal-facing shoulder 1408 can be conical, spherical, stepped, tapered, etc. The proximal-facing shoulder 1408 can be planar and can extend perpendicular to the axis A1. The projection 1410 can define a distal-facing shoulder 1412 for contacting a proximal-facing shoulder 1414 of the collet ring 1404 to limit distal translation of the compression cap 1402 relative to the collet ring along the axis A1. The distal-facing shoulder 1412 can be obliquely angled with respect to the axis A1. For example, the distal-facing shoulder 1412 can be conical, spherical, stepped, tapered, etc. The distal-facing shoulder 1412 can be planar and can extend perpendicular to the axis A1. The projection 1410 can define a cylindrical outer surface 1416 configured to mate with a cylindrical inner surface 1418 of the collet ring 1404, as described below.

The compression cap 1402 can define a central opening 310 that extends completely through the compression cap along the axis A1. The opening 310 can be sized to receive a guide wire or needle therethrough, or to receive a driver therethrough for engaging the drive interface of the bone anchor 400.

The compression cap 1402 can include a distal-facing bearing surface 1420 configured to contact and bear against the head 402 of the bone anchor 400, e.g., to lock polyaxial movement of the bone anchor relative to the receiver member 200'. The bearing surface 1420 can be spherical or substantially spherical. The bearing surface 1420 can include one or more teeth or ridges, and/or various other surface coatings, treatments, or geometries to enhance grip between the compression cap 1402 and the head 402 of the bone anchor 400. The bearing surface 1420 can be spherical and can have a diameter slightly less than the diameter of the shank head 402 sphere. As a result, when locked, a ring-shaped line contact can be formed between the compression cap 1402 and the head 402, which may enhance the poly-slip performance of the assembly 1400. The bearing surface 1420 can also serve to limit proximal travel of the shank 400 relative to the receiver member 200' during assembly. This can help guard against a situation where the shank 400 is inserted so forcefully into the receiver member 200' as to risk the head 402 passing proximally beyond the collet fingers 316. In such a situation, the head 402 would first contact the bearing surface 1420 and would thereby be prevented from passing proximally beyond the collet fingers 316.

The compression cap 1402 can include features for engaging the compression cap with an instrument to manipulate the compression cap, e.g., as described above with respect to the collet 300.

The collet ring 1404 can include a generally-cylindrical proximal body 1406. The collet ring 1404 can define a central opening 310 that extends completely through the collet ring along the axis A1. The opening 310 can be sized to receive a guide wire or needle therethrough, or to receive a driver therethrough for engaging the drive interface of the bone anchor 400. The opening can further be configured to receive the compression cap 1402 therein, such that the compression cap is coaxial with, and telescopically slidable with respect to, the collet ring 1404. A proximal-facing shoulder 1414 can be defined within the opening 310 to limit distal travel of the compression cap 1402 relative to the collet ring 1404.

The collet ring 1404 can include one or more slits formed therein to define a plurality of distally-extending fingers 316. The fingers 316 can be configured to deform radially-inward and/or radially-outward from a resting position. The fingers 316 can have resilient properties such that, when deformed from their resting position, the fingers are biased towards the resting position.

While the illustrated collet ring 1404 includes six fingers 316, it will be appreciated that the collet ring can include any number of fingers, e.g., zero, one, two, three, four, five, six, seven, eight, or more. Including a larger number of fingers 316 can result in each individual finger being narrower in width for a given size collet ring 1404, making the finger easier to deflect during assembly.

The slits can have an expanded or T-shaped proximal end to provide a relief and allow the fingers 316 to deform to a greater degree with less effort or without breaking. The fingers 316 can include a reduced-thickness region 318 adjacent their proximal end to encourage bending of the fingers at a predetermined bend zone. The distal-most ends of the fingers 316 can include a curved, tapered, angled, or ramped surface 320 to provide a lead in for entry of the head 402 of the bone anchor 400 and for wedging the collet fingers between the head of the bone anchor and the receiver member 200'. The lead-in surface 320 can face substantially radially-inward. The inner surfaces of the fingers 316 can be spherical or substantially spherical. The outer surfaces of the fingers 316 can likewise be spherical or substantially spherical. In some embodiments, the inner surfaces of the fingers 316 each form sections of a common sphere.

The fingers 316 can have a resting diameter greater than that of the opening defined by the retaining ring 1302, such that the collet ring 1404 is retained in the cavity 222. It will be appreciated that the retaining ring 1302 can allow the collet ring 1404 to be retained within the cavity 222 without necessarily requiring swaging. Swaging is a common manufacturing process that involves permanent material deformation to retain one component within another. Deformation of material during the swaging process is less predictable than traditional machining processes and can require special manufacturing controls, which can increase manufacturing cost. The illustrated bone anchor assembly 1400 can thus be easier and less expensive to manufacture than bone anchor assemblies that require swaging. While swaging is not necessarily required, in some embodiments, swaging can be used to retain the collet 300' within the cavity 222 or to augment the retention of the collet.

The fingers 316 can be deformed from their resting position as the head 402 of the shank 400 is loaded into the distal end of the collet ring 1404. The receiver member 200' and the collet ring 1404 can be assembled to the head 402 of the shank 400 by applying a distal axial force to the receiver member over the head of the shank. The head 402 of the shank 400 can bear against the distal lead-in surfaces 320 of the fingers 316 to deform the fingers radially-outward from their resting position. Once the head 402 of the shank 400 is advanced far enough into the collet ring 1404, the fingers 316 can return towards their resting position, capturing the head of the shank therein to retain the shank within the collet 300' and, by extension, within the receiver member 200'. When captured within the collet ring 1404, and before the collet is locked down within the receiver member 200', the shank 400 can still be free to pivot with respect to the collet ring and to rotate about the axis A1 relative to the collet ring. The collet ring 1404 can apply a drag force to the head 402 of the bone anchor 400, e.g., due to a light interference fit between the collet fingers 316 and the head of the bone anchor. The drag force can maintain the relative position between the receiver member 200' and the bone anchor 400 prior to locking the construct, e.g., during provisional positioning of the assembly 1400, to prevent the receiver member from "flopping" over. The drag force can thus prevent unintended movement prior to locking the assembly 1400, while still allowing free movement when intended by the user.

Once assembled to the head 402 of the shank 400, rod insertion and set screw 102 locking can be effective to drive the collet ring 1404 distally with respect to the receiver member 200', wedging the collet fingers 316 between the head of the shank and the seat 234 of the retaining ring 1302, thereby locking movement of the shank with respect to the receiver member.

Figure 14G:
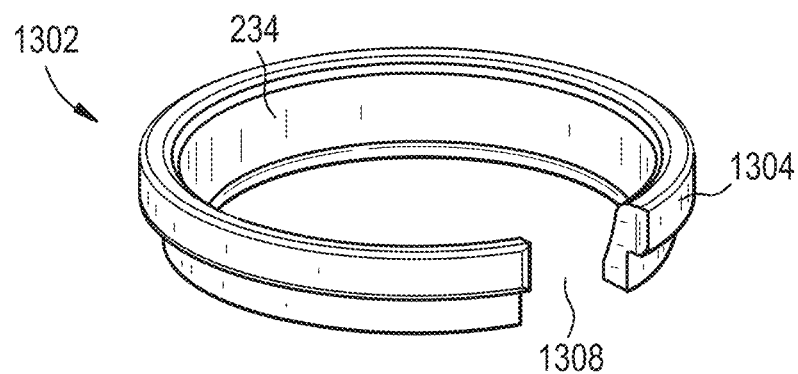
FIG. 14G is a perspective view of a retaining ring of the bone anchor assembly of FIG. 14A.

The insert 1302 is shown in detail in FIGS. 14C and 14G. The insert 1302 can be a ring-shaped body having an inner surface, an outer surface, and a central opening extending therethrough. The central opening can be large enough to allow the head 402 of the shank 400 to pass therethrough along the axis A1, but small enough to prevent the collet 300' from passing distally through the insert 1302. The central opening of the insert 1302 can have a diameter that is less than a resting outer diameter of the fingers 316 of the collet 300'.

The insert 1302 can be secured to the receiver member 200' in various ways, as described in detail above. For example, as shown, the outer surface of the insert 1302 can include a ridge 1304 that extends radially-outward therefrom. An inner surface of the receiver member 200' can include a counterpart groove 1306 in which the ridge 1304 can be received to secure the insert 1302 to the receiver member. When the ridge 1304 is received within the groove 1306, the insert 1302 can be prevented from moving proximally or distally along the axis A1 relative to the receiver member 200'. The insert 1302 can be radially-expandable and/or radially-collapsible to facilitate insertion of the ridge 1304 into the groove 1306 during assembly. For example, the insert 1302 can include a cut 1308 such that the insert forms a C-clip as shown. In other arrangements, the insert 1302 can include one or more slits, webbed portions, or other features for allowing expansion and/or contraction of the insert. It will be appreciated that the positioning of the ridge 1304 and the groove 1306 can be reversed, such that the groove is formed in the insert 1302 and the ridge is formed in the receiver member 200'. While a continuous circumferential ridge 1304 and groove 1306 are shown, in other arrangements the insert 1302 can include one or more discrete projections configured to be received within a corresponding one or more discrete pockets of the receiver member 200' to retain the insert therein.

The set screw 102 can include an exterior thread configured to mate with the interior threads formed on the arms 202, 204 of the receiver member 200'. The threaded engagement can allow the set screw 102 to be advanced or retracted along the axis A1 with respect to the receiver member 200' by rotating the set screw about the axis A1. The set screw 102 can include a driving interface configured to receive a driver for applying a rotational force to the set screw about the axis A1. The distal surface of the set screw 102 can be configured to contact and bear against a rod R1 disposed in the rod-receiving recess 206 to lock the rod to the assembly 1400. When tightened against the rod R1, the set screw 102 can prevent the rod from translating relative to the receiver member 200' along the axis A2 and/or from rotating with respect to the receiver member about the axis A2. While a set screw 102 is shown, it will be appreciated that other locking elements can be used instead or addition, such as a closure cap that advances and locks by quarter-turn rotation, a closure cap that slides in laterally without rotating, a nut that threads onto an exterior of the receiver member 200', and so forth. In some embodiments, a dual set screw can be used. The dual set screw can include an outer set screw that bears against the arms 302, 304 of the compression cap 1402 to lock the polyaxial movement of the shank 400 relative to the receiver member 200'. The dual set screw can also include an inner set screw threadably mounted in an opening formed in the outer set screw. The inner set screw can be tightened to bear against the rod R1 and to lock the rod to the receiver member 200'.

As shown in FIG. 14B, the shank or bone anchor 400 can include a proximal head portion 402 and a distal shaft portion 404 and can define a central longitudinal bone anchor axis A3.

As noted above, the bone anchor assembly 1400 can be assembled by loading the collet 300', including the compression cap 1402 and the collet ring 1404, into the distal end of the receiver member 200' and then attaching the insert 1302 to the receiver member to retain the collet therein. Once assembled, use of the bone anchor assembly 1400 can be substantially the same as that of the bone anchor assemblies 100, 1300 described above. As shown in FIG. 14C, the head 402 of the shank 400 can be loaded into the distal end of the insert 1302 and passed proximally therethrough into the receiver member 200'. An axial force can be applied to the receiver member 200', causing the head 402 of the shank 400 to push the collet fingers 316 into the middle portion 226 of the cavity 222, where the collet fingers are allowed to radially expand and allow passage of the head of the shank into the collet ring 1404. The collet fingers 316 can constrain the shank head 402 within the receiver member 200'. Diametrical interference between the shank head 402 and the collet fingers 316 inner sphere can create drag between the two components, e.g., for provisional positioning of the bone anchor assembly 1400 and to prevent flopping. A rod R1 and a set screw 102 can be installed into the receiver member 200'. Subsequent rotation of the set screw 102 can draw the receiver member 200' upward relative to the rod R1 and the head 402 of the shank 400, which can be implanted in bone. This movement can wedge the collet fingers 316 between the shank head 402 and the insert 1302 and force the compression cap 1402 against the shank head. The insert 1302, the collet fingers 316, and the compression cap 1402 can be configured to constrain the shank head 402 in the receiver member 200', thereby creating a polyaxial locking mechanism. The insert 1302 inner surface can be spherical to accept collet fingers 316 with an outer spherical shape to facilitate remobilization of polyaxial motion upon set screw removal.

FIGS. 14H-14K illustrate the bone anchor assembly 1400 in various exemplary states of component positioning.

Figure 14H:
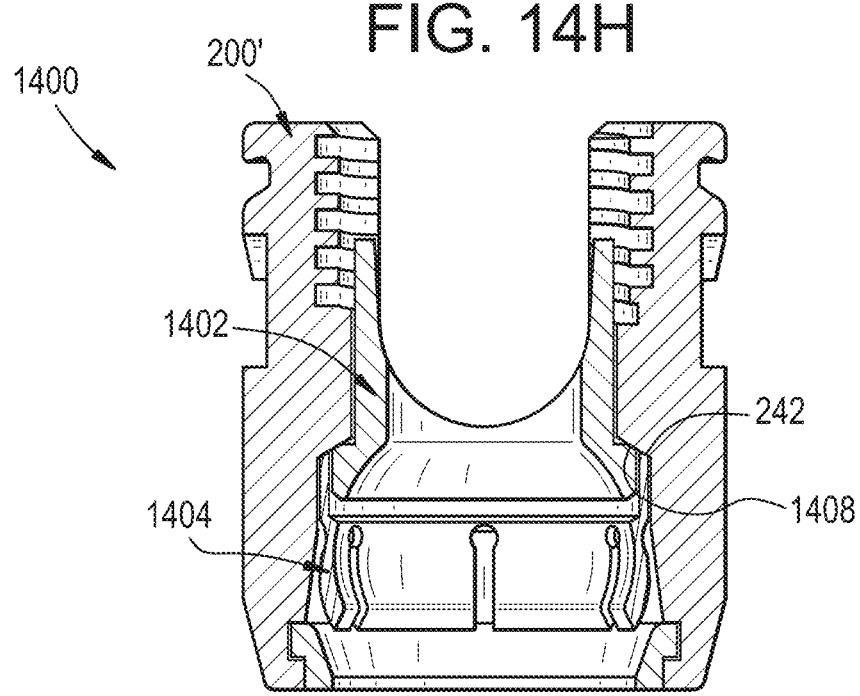
FIG. 14H is a sectional side view of the bone anchor assembly of FIG. 14A in a first configuration.

In FIG. 14H, the compression cap 1402 and the collet ring 1404 are each shown at their respective limits of proximal travel within the receiver member 200' along the axis A1. In this state, the proximal end of the collet ring 1404 and the proximal-facing shoulder 1408 of the compression cap 1402 contact the distal-facing shoulder 242 of the receiver member 200'.

Figure 14I:
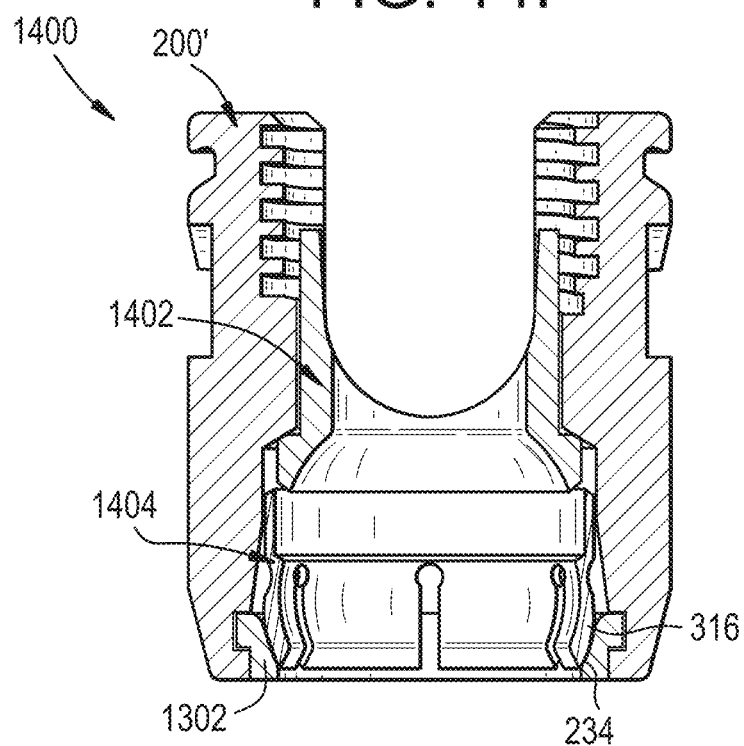
FIG. 14I is a sectional side view of the bone anchor assembly of FIG. 14A in a second configuration.

In FIG. 14I, the compression cap 1402 is shown at its limit of proximal travel within the receiver member 200' along the axis A1 and the collet ring 1404 is shown at its limit of distal travel within the receiver member 200' along the axis A1. In this state, the collet fingers 316 contact the seat 234 of the retaining ring 1302 to prevent the collet ring 1404 from falling distally out of the receiver member 200'. As shown, in this state, the axial spacing between the various shoulders and stop surfaces of the assembly 1400 can be selected such that an axial overlap always exists between the compression cap 1402 and the collet ring 1404, e.g., such that at least a portion of the compression cap remains disposed within the central opening of the collet ring at all times. This can help prevent inadvertent separation, toggling, jamming, etc. of the internal components of the assembly 1400.

Figure 14J:
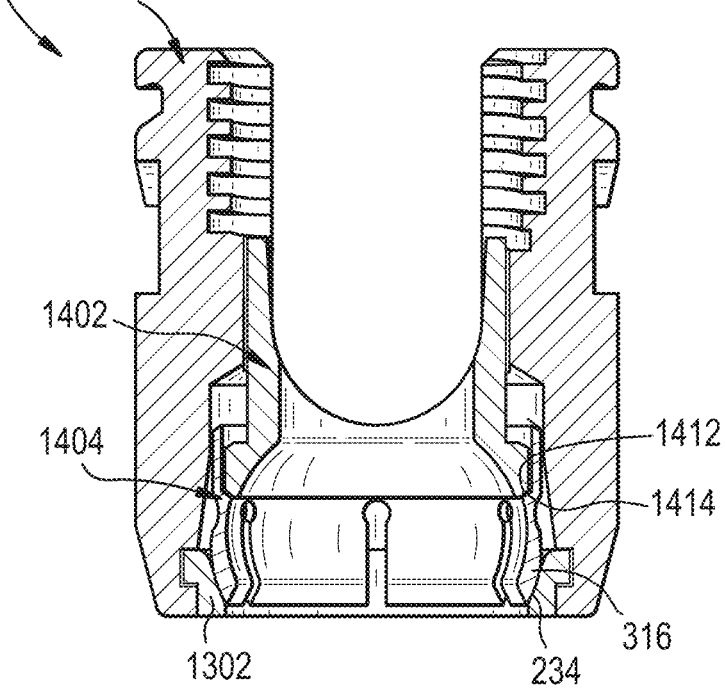
FIG. 14J is a sectional side view of the bone anchor assembly of FIG. 14A in a third configuration.

In FIG. 14J, the compression cap 1402 and the collet ring 1404 are each shown at their respective limits of distal travel within the receiver member 200' along the axis A1. In this state, the collet fingers 316 contact the seat 234 of the retaining ring 1302 to prevent the collet ring 1404 from falling distally out of the receiver member 200'. Also in this state, the distal-facing shoulder 1412 of the compression cap 1402 contacts the proximal-facing shoulder 1414 of the collet ring 1404 to limit distal travel of the compression cap.

Figure 14K:
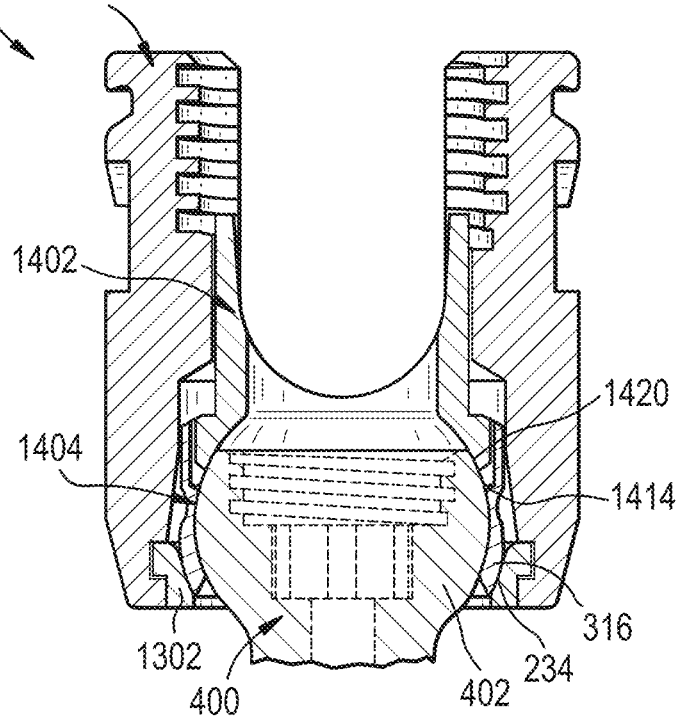
FIG. 14K is a sectional side view of the bone anchor assembly of FIG. 14A in a fourth configuration.
Figure 15A:
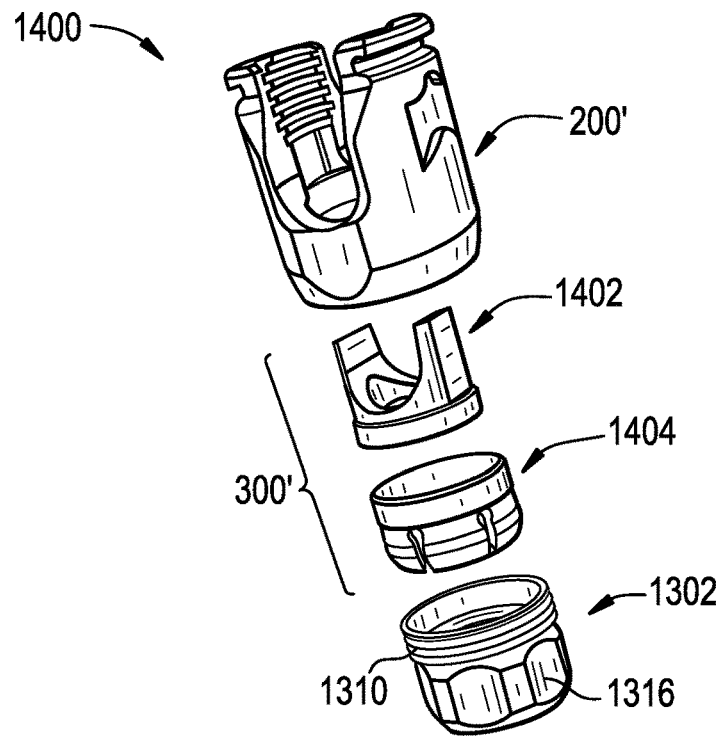
FIG. 15A is an exploded perspective view of a bone anchor assembly.
Figure 15B:
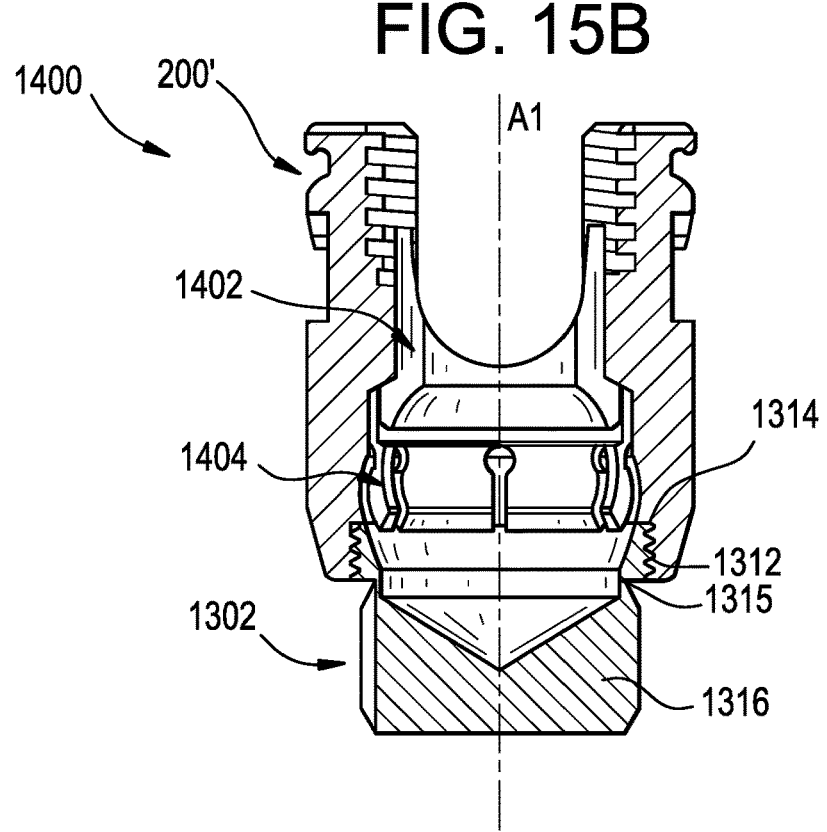
FIG. 15B is a sectional side view of the bone anchor assembly of FIG. 15A.

In FIG. 14K, the compression cap 1402 and the collet ring 1404 are shown in a typical locking position in which the assembly 1400 is locked to prevent polyaxial movement between the shank 400 and the receiver member 200'. In this state, the collet fingers 316 are wedged between the head 402 of the shank 400 and the seat 234 of the retaining ring 1302 to apply a locking force to a distal region of the shank head. Also in this state, the distal-facing bearing surface 1420 of the compression cap 1402 is compressed against the shank head 402 to apply a locking force to a proximal region of the shank head. The proximal-facing shoulder 1414 of the collet ring 1404 can be formed at sufficient depth within the central opening of the collet ring to ensure that the compression cap 1402 contacts the shank head 402 first during locking, before bottoming-out within the collet ring.

As shown in FIGS. 15A-15D, the bone anchor assembly 1400 described above can include a threaded insert 1302. The outer surface of the insert 1302 can include a thread 1310 that engages with a corresponding thread 1312 formed in the inner surface of the receiver member 200'. Accordingly, rotation of the insert 1302 about the axis A1 relative to the receiver member 200' can be effective to advance or retract the insert into the receiver member along the axis A1. In some embodiments, the insert 1302 can be threadably advanced into the receiver member 200' until a proximal end of the insert contacts and bears against a distal-facing shoulder 1314 formed in the receiver member. A distal-facing surface of the insert 1302, e.g., at the terminal distal end of the insert, can include a drive feature 1316 to facilitate application of torque to the insert. The drive feature can be a male drive feature 1316 that projects distally from the insert 1302. The male drive feature 1316 can be configured to break or shear off from the insert 1302 when a pre-determined threshold force, e.g., a predetermined threshold torque, is applied thereto. Accordingly, the insert 1302 can be tightened to the receiver member 200' until the male drive feature 1316 breaks off, indicating to the user that the insert is tightened sufficiently and, optionally, preventing subsequent removal of the insert from the receiver member. The male drive feature can include a generally cylindrical plug 1316. The plug 1316 can include one or more flats, grooves, or other features for transferring torque from a driver instrument to the plug. For example, the plug 1316 can have an outer hex drive feature as shown. The plug 1316 can be connected to or formed integrally with the threaded portion of the insert 1302, e.g., via a frangible portion or shear feature 1315. The shear feature 1315 can be a relatively thin-walled annular section of material at the junction between the plug 1316 and the threaded portion of the insert 1302. At least a portion of the plug 1316 can be hollow to define the section of material. The outer surface of the plug 1316 can be tapered or stepped radially-inward to define the section of material. The shear feature 1315 can be configured to break or shear when the insert 1302 is bottomed out against the shoulder 1314 of the receiver member 200' and sufficient torque is applied to the plug 1316. While a male drive feature 1316 is shown, in other arrangements the insert 1302 can include a female drive feature configured to be sheared off, e.g., in the form of a plug having an internal, female hex drive feature.

An exemplary method of assembling the receiver or head portion of the bone anchor assembly 1400 is shown in FIG. 15D. In step (1), the receiver member 200' can be positioned upside down to allow insertion of the compression cap 1402 and the collet ring 1404 in subsequent steps, with gravity helping to retain the cap and collet ring within the receiver member during assembly. The receiver member 200' can be positioned in an alignment jig to hold and stabilize the receiver member during assembly. In step (2), the compression cap 1402 can be loaded into the open distal end of the receiver member 200' and seated against the shoulder 242 of the receiver member. The alignment jig can include a temporary rod or bar positioned through the rod-receiving recess 206 of the receiver member 200', which can help ensure that the compression cap 1402 is inserted in the correct orientation, e.g., with the arms of the compression cap aligned with the arms of the receiver member. In step (3), the collet ring 1404 can be loaded into the open distal end of the receiver member 200' and seated against the compression cap 1402 and/or the shoulder 242. In step (4) the insert 1302 can be threaded into the open distal end of the receiver member 200', retaining the compression cap 1402 and the collet ring 1404 within the cavity of the receiver member. The insert 1302 can be rotated about the axis A1 to advance the insert into the cavity until the proximal end of the insert abuts the shoulder 1314 of the receiver member 200' to prevent further rotation. Continued application of torque to the drive feature 1316 of the insert 1302 can be effective to shear the drive feature off of the insert. In particular, upon application of a threshold torque to the drive feature 1316, the drive feature can break off from the insert 1302 at the reduced-thickness annular shear portion 1315. In some embodiments, other manufacturing steps such as staking and/or peening can be performed to further secure the remaining portion of the insert 1302 to the receiver member 200' and to prevent the insert from backing out of the receiver member. Any sharp edge that may be left upon shearing the drive feature 1316 can be removed in a deburring step. Step (5) illustrates the finished head assembly. The head assembly can be assembled to a shank 400, spinal rod R1, and/or closure mechanism 102 at this time, or such assembly can occur later, e.g., within the operating room and/or when the assembly is partially or completely implanted in a patient.

The insert 1302 can have a thread direction that is opposite to the thread direction of the shank 400. For example, the shank 400 can have a right-hand bone engaging thread while the insert 1302 has a left-hand thread 1310. This can advantageously prevent the insert 1302 from loosening from the receiver member 200' as the shank 400 is driven into bone, e.g., if the surgeon attempts to lag the receiver member to the bone by continued tightening of the shank after the receiver member is attached.

The head assembly process shown in FIG. 15D can be performed entirely at an off-site manufacturing facility, entirely within the operating room and/or within the patient, or in any combination of said locations. The head assembly can be assembled at a manufacturing facility and then the shank can be attached to the head assembly in the operating room or in the patient. Alternatively, the shank can be attached to the head assembly at the manufacturing facility.

The design of the bone anchors and associated assembly methods described herein can advantageously ensure a secure connection of the retaining insert to the receiver member during initial assembly. For example, they can ensure that a specified torque is applied to the assembly before it leaves the factory, without the need for special in-process torque measurement. The bottom loading nature of these solutions can also enable in situ head assembly, and screw shanks of any bone thread diameter to use the same head assembly method. The above-described embodiments can provide a consistent method of component retention inside of a screw head that employ traditional machining and assembly operations, regardless of shank size, thereby providing manufacturing assembly, portfolio management, and quality control advantages.

Figure 16A:
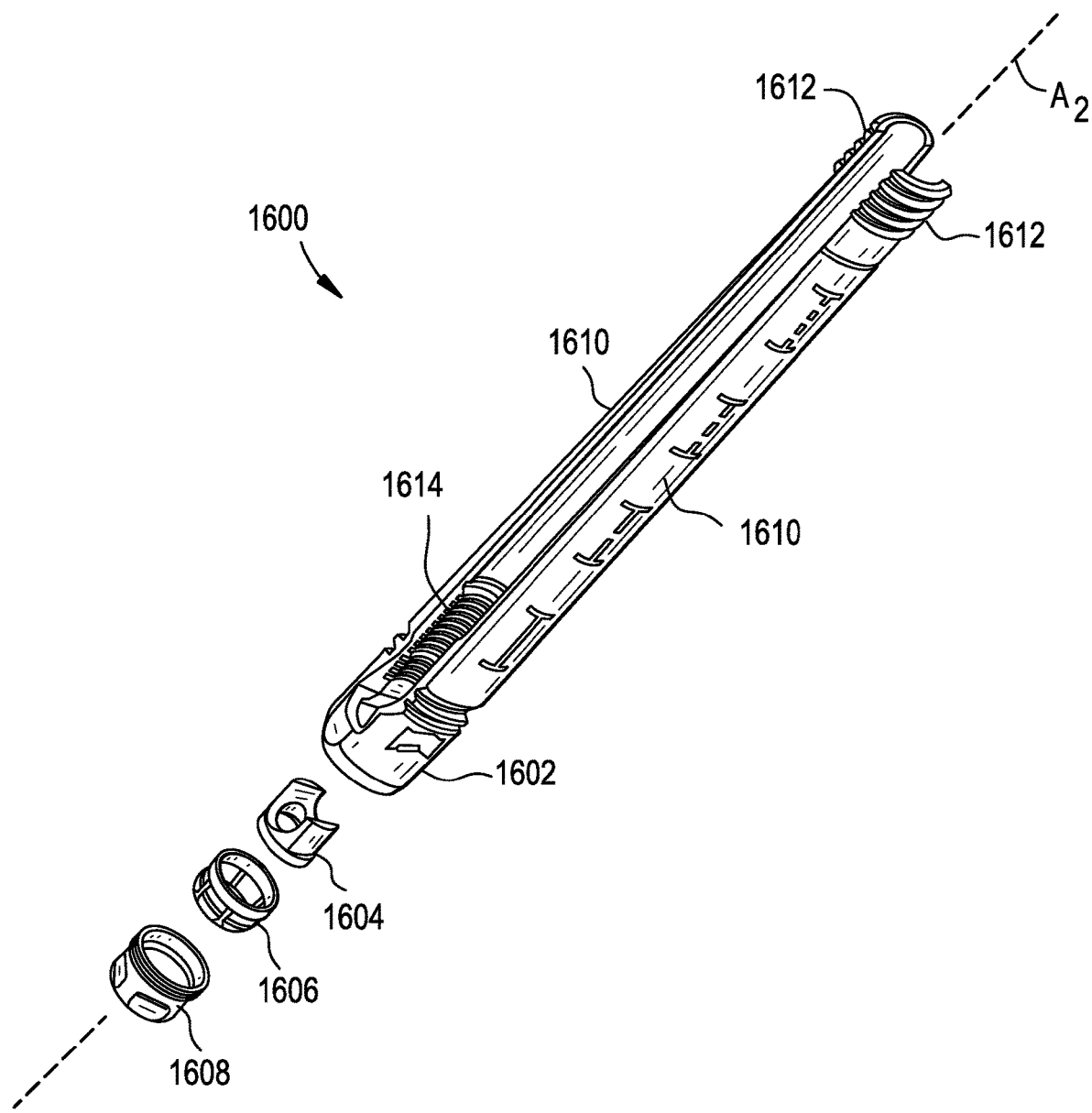
FIG. 16A is an exploded perspective view of another bone anchor assembly.

FIGS. 16A-16E illustrate another embodiment of a bone anchor assembly 1600 according to the present disclosure. As shown in the exploded view of FIG. 16A, the bone anchor assembly 1600 can include components similar to those described above with respect to, e.g., the assembly 1400. Because operation of the various components can be similar to embodiments already described above, detailed description is omitted for brevity below. Turning to FIG. 16A, the bone anchor assembly 1600 can include a receiver member 1602, which can be similar to the receiver members 200, 200' described above, as well as a compression cap 1604, collet ring 1606, and retaining ring or insert 1608. The compression cap 1604 and collet ring 1606 can together form a multipart collet, similar to the multipart collet 300' formed from the compression cap 1402 and collet ring 1404 described above. Finally, the retaining ring or insert 1608 can function in a similar manner to the insert 1302 described above.

Turning to specifics of the embodiments shown in FIGS. 16A-16E, the receiver member 1602 can include extended tabs 1610 that can aid in receiving and reducing a spinal fixation element and set screw distally into the seat formed in the receiver member 1602. The extended tabs 1610 can be similar to the reduction tabs 244 described above and shown in FIG. 5A. Moreover, any of the various embodiments described herein can include extended tabs like those shown in FIGS. 5A and 16A-16D.

The tabs 1610 can have any of a variety of lengths. For example, in some embodiments the tabs can extend about 100 mm. In other embodiments, however, other lengths can be used. The extended tabs 1610 can have a cross-sectional shape that matches that of the arms of the receiver member. Further, the tabs 1610 can include threads 1612 formed on an outer surface thereof (e.g., along a proximal end portion thereof) to facilitate attachment of the tabs to various surgical instruments. Still further, the tabs 1610 can have a threaded interior surface 1614 (e.g., along a distal end portion thereof) such that the tabs 1610 serve as a functional extension of the arms of the receiver member during set screw insertion and rod reduction.

The tabs 1610 can be integrally formed with the receiver member 1602 and, in some embodiments, can be configured to be broken or cut away after use. To this end, in some embodiments the tabs 1610 can include a narrowed portion 1616 near a proximal end of the receiver member arms that can facilitate easier breaking or cutting of the tabs 1610 from the receiver member 1602. In still other embodiments, the tabs 1610 can be separate components that can be selectively coupled to the arms of the receiver member 1602.

Figure 16E:
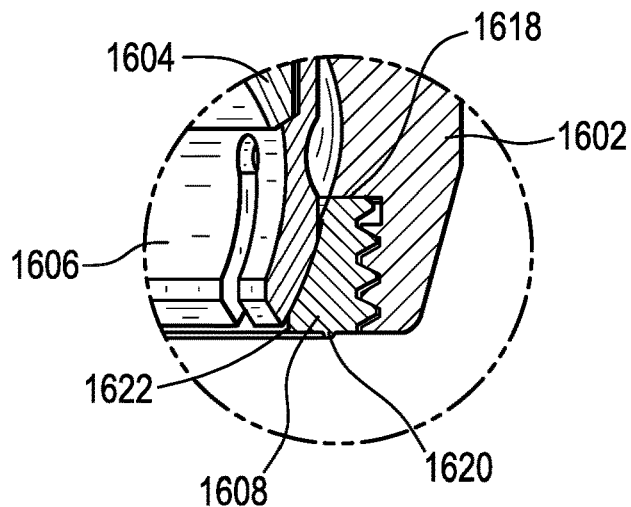

The detail view of FIG. 16E, showing the circled portion labeled B in FIG. 16C, illustrates the interaction of the receiver member 1602, compression cap 1604, collet ring 1606, and retaining ring or insert 1608. Note that in FIG. 16E, the retaining ring or insert 1608 is shown after a drive feature 1902 thereof is broken away. The drive feature 1902, shown in greater detail in FIGS. 19A-19E, can operate similarly to the above described drive feature 1316. Referring back to FIG. 16E, the various components are illustrated in a configuration wherein the retaining ring 1608 is bottomed out, or threaded proximally to a maximum extent within, a threaded portion of a cavity formed in the receiver member 1602. In the illustrated configuration, a proximal end of the retaining ring or insert 1608 can bear against a distal-facing shoulder 1618 formed in the receiver member 1602.

Figure 17:
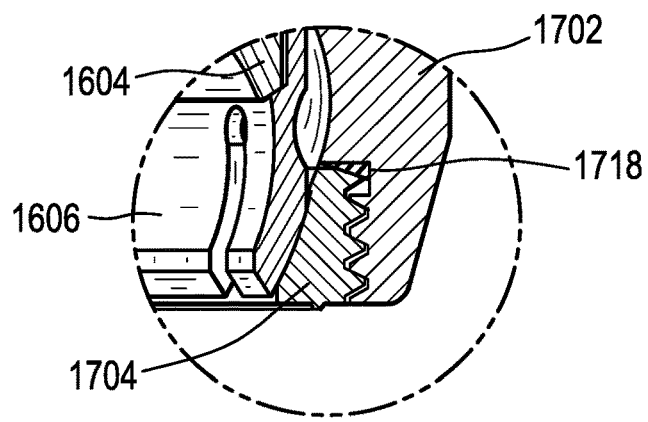
Figure 18:
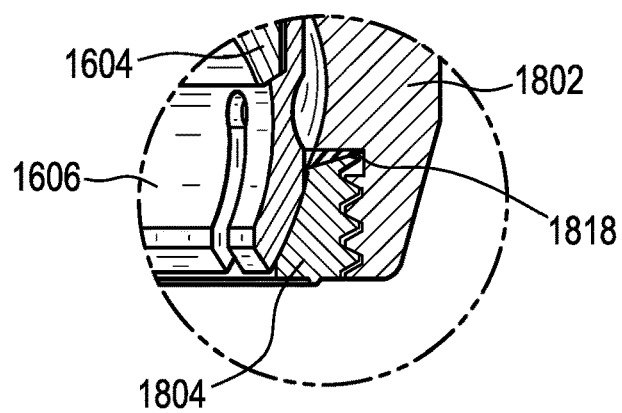

In the illustrated embodiment, the distal-facing shoulder 1618 can be flat, i.e., arranged such that the surface is perpendicular to a longitudinal axis A2 of the receiver member 1602 or assembly 1600, as shown in FIG. 16A. In other embodiments, however, the shoulder can be angled to taper inward or outward, i.e., arranged such that the surface is oblique to the longitudinal axis A2. Examples of such embodiments are shown in FIGS. 17 and 18. In FIG. 17, for example, a receiver member 1702 is shown having a distal-facing shoulder 1718 that tapers radially inward when progressing along the surface from a distal end thereof to a proximal end thereof. When combined with a retaining ring 1704 having a complementary proximal end, such a configuration can create a taper lock that can enhance locking of the retaining ring 1704 within the cavity of the receiver member 1702.

FIG. 18 illustrates another embodiment wherein a receiver member 1802 includes a distal-facing shoulder 1818 that tapers radially outward when progressing along the surface from a distal end thereof to a proximal end thereof. When combined with a retaining ring 1804 having a complementary proximal end, such a configuration can provide additional support against radially-inward buckling of the retaining ring 1804 that can occur when the drive feature 1904 is torqued to break off from the remainder of the retaining ring 1804. That is, the interlocking of the proximal end of the retaining ring 1804 and the tapered distal-facing shoulder 1818 can resist radially inward movement of the retaining ring 1804 under shear loading. Note that is also possible to increase resistance to shear load buckling in the embodiments shown in FIGS. 16E and 17 in alternative manners, e.g., by providing thicker retaining ring sidewalls to increase ring strength, etc.

FIGS. 19A-19E illustrate various views of the retaining ring or insert 1608 that includes a drive feature 1902. As described above, the drive feature 1902 can be configured break off from the retaining ring or insert 1608 when a predetermined threshold force, e.g., a predetermined threshold torque, is applied thereto. Accordingly, the retaining ring or insert 1608 can be tightened to the receiver member 1602 until the drive feature breaks off, indicating to the user that the insert is sufficiently tightened and, optionally, preventing overtightening or subsequent removal of the retaining ring from the receiver member. The drive feature 1902 can have a variety of configurations. In some embodiments, the drive feature 1902 can be one or more female recesses sized to receive a corresponding male drive feature of a driver instrument. In other embodiments, and as shown in FIGS. 19A-19E, the drive feature 1902 can be a male drive feature that projects distally from the retaining ring or insert 1608. In the illustrated embodiment, the drive feature 1902 includes a generally cylindrical plug that includes two pairs of opposed flat surfaces 1904 that can be used to rotate the retaining ring or insert 1608. A variety of other combinations of flats, grooves, or other features can be employed, e.g., such as the hex or six-sided flat arrangement of the drive feature 1316 shown in FIG. 15A.

Figure 19D:
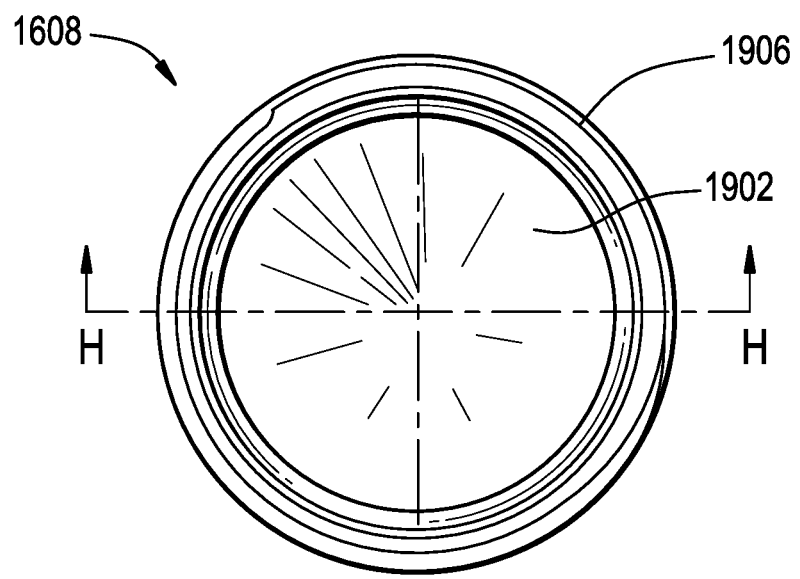
Figure 19E:
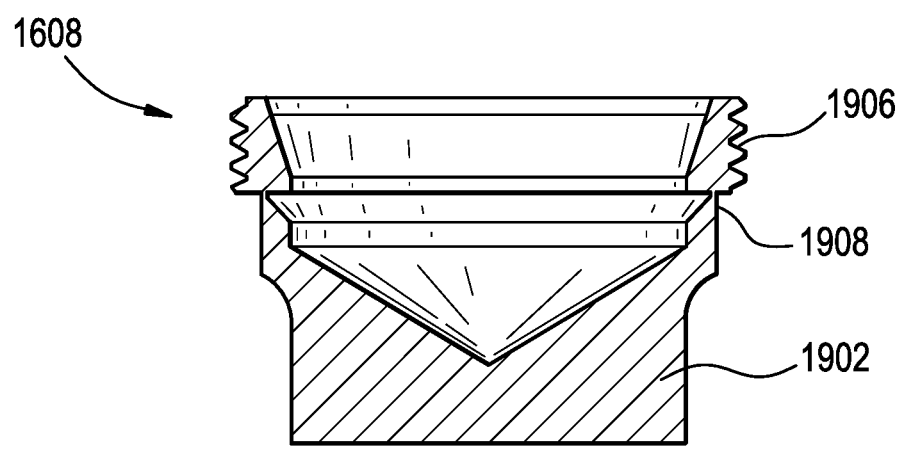

The drive feature 1902 can be connected to or integrally formed with a threaded portion 1906, e.g., via a frangible portion or shear feature 1908 (see FIG. 19E). The shear feature 1908 can be a relatively thin-walled annular section of material at the junction between the drive feature 1902 and the threaded portion of the retaining ring or insert 1608. The shear feature 1908 can be configured to break or shear when the insert 1608 is bottomed out against the shoulder 1618 of the receiver member 1602 and sufficient torque is applied to the drive feature 1902. While a male drive feature 1902 is shown in FIGS. 19A-19E, in other embodiments the insert can include a female drive feature configured to be sheared off, e.g., in the form of a plug having an internal, female hex or square drive feature.

As described above, the shear feature 1908 can be formed by tapering or stepping the material forming the shear feature to create the relatively thin-walled annular section of material. The shear feature 1908, however, is shown as oppositely arranged from the shear feature 1315 described above. More specifically, the shear feature 1908 can be formed by tapering or stepping radially-outward an inner surface of the insert 1608. Forming the shear feature 1908 in this manner can move the location of the connection between the threaded portion of the insert 1608 and the drive feature 1902 radially outward relative to the arrangement shown in FIG. 15C. This can be advantageous because any burr that remains after the drive feature 1902 is broken free from the remainder of the retaining ring or insert 1608 will similarly be positioned radially outward and away from an inner diameter of the insert 1608 that defines a through-hole into which a head portion of a bone anchor can be passed, thereby preventing any unintended interference between the burr and the bone anchor. By way of example, the burr 1620 can be seen in FIG. 16E positioned radially outward from an inner edge 1622 of the retaining ring 1608 that defines the through-hole into which a proximal head portion of a bone anchor can be passed.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

While the methods illustrated and described herein generally involve attaching spinal rods to multiple vertebrae, it will be appreciated that the devices and methods herein can be used with various other types of fixation or stabilization hardware, in any bone, in non-bone tissue, or in non-living or non-tissue objects. The bone anchor assemblies and other implants disclosed herein can be fully implanted, or can be used as part of an external fixation or stabilization system. The devices and methods disclosed herein can be used in minimally-invasive surgery and/or open surgery.

The devices disclosed herein and the various component parts thereof can be constructed from any of a variety of known materials. Exemplary materials include those which are suitable for use in surgical applications, including metals such as stainless steel, titanium, cobalt-chromium, titanium-molybdenum, or alloys thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

Although specific embodiments are described above, it should be understood that numerous changes may be made within the spirit and scope of the concepts described.

The invention claimed is:

1. A method of assembling a bone anchor assembly, comprising:
   inserting a component into a cavity formed in a receiver member of the bone anchor assembly by passing the component through a distal opening of the cavity, the component comprising a compression cap and a collet ring, the collet ring comprising a plurality of fingers, wherein the collet ring is passed through the distal opening of the cavity without deflecting said fingers;
   after inserting the component into the cavity, attaching an insert to the receiver member to prevent the component from moving distally through the distal opening of the cavity;
   wherein attaching the insert comprises applying torque to a drive feature of the insert to advance the insert proximally relative to the receiver member until the insert bottoms out in the cavity and applying further torque to separate the drive feature from the insert at a shear portion; and
   after attaching the insert to the receiver member, inserting a head portion of a bone anchor through a central opening of the insert and into the collet by:
      deflecting the fingers of the collet radially-outward to allow the head portion of the bone anchor to pass through a distal opening defined by the fingers; and
      collapsing the plurality of fingers radially-inward once the head portion is disposed within the collet to retain the head portion within the collet.

2. The method of claim 1, wherein the drive feature comprises a plug extending distally from a threaded portion of the insert, the plug having one or more flats for applying torque thereto.

3. The method of claim 2, wherein the shear portion is disposed between the plug and the threaded portion of the insert.

4. The method of claim 2, wherein the shear portion comprises a thin-walled annular section of material.

5. The method of claim 2, wherein the plug is at least partially hollow to define an annulus of material to serve as the shear portion.

6. The method of claim 1, wherein the insert bottoms out against a distal-facing shoulder formed in the cavity.

7. The method of claim 1, wherein collapsing the plurality of fingers of the collet applies a drag force to the head portion of the bone anchor to prevent unintended movement between the receiver member and the bone anchor.

8. The method of claim 7, further comprising inserting a spinal fixation element and a set screw into the receiver member to drive the receiver member proximally with respect to the collet, wedge the plurality of fingers of the collet between the head portion of the bone anchor and the receiver member, and lock movement of the bone anchor relative to the receiver member.

9. A bone anchor assembly, comprising:
   a receiver member having proximal and distal ends that define a central proximal-distal axis, the receiver member having a cavity formed therein, the cavity being open to the distal end of the receiver member;
a component disposed in the cavity;
an insert attached to the receiver member to retain the component within the receiver member, the insert having a drive feature configured to shear off from the insert when the insert is bottomed out within the cavity and when sufficient torque is applied to the drive feature; and
a shank that extends through the insert, the shank having a head portion retained between a plurality of fingers of the component;
wherein the drive feature comprises a plug having one or more flats for applying torque thereto and wherein the plug is connected to the insert by a reduced thickness annular section of material.

10. The assembly of claim 9, wherein the insert includes an exterior thread mated to an interior thread of the receiver member.

11. The assembly of claim 9, wherein the component comprises at least one of a collet ring and a compression cap.

12. A method of assembling a bone anchor assembly, comprising:
inserting a component into a cavity formed in a receiver member of the bone anchor assembly by passing the component through a distal opening of the cavity; and
after inserting the component into the cavity, attaching an insert to the receiver member to prevent the component from moving distally through the distal opening of the cavity;
wherein attaching the insert comprises applying torque to a drive feature of the insert to advance the insert proximally relative to the receiver member until the insert bottoms out in the cavity and applying further torque to separate the drive feature from the insert at a shear portion, and
wherein the insert bottoms out against a distal-facing shoulder formed in the cavity.

13. The method of claim 12, wherein the distal opening of the cavity is configured to have a shank extend thorough the distal opening and insert when the bone anchor assembly is fully assembled.

14. The method of claim 12, wherein the drive feature comprises a plug extending distally from a threaded portion of the insert, the plug having one or more flats for applying torque thereto.

15. The method of claim 14, wherein the shear portion is disposed between the plug and the threaded portion of the insert.

16. The method of claim 14, wherein the shear portion comprises a thin-walled annular section of material.

17. The method of claim 14, wherein the plug is at least partially hollow to define an annulus of material to serve as the shear portion.

18. The method of claim 12, wherein the component comprises a compression cap and a collet ring.

19. The method of claim 18, wherein the collet ring includes a plurality of fingers and wherein the collet ring is passed through the distal opening of the cavity without deflecting said fingers.

20. The method of claim 19, further comprising, after attaching the insert to the receiver member, inserting a head portion of a bone anchor through a central opening of the insert and into the collet by:
deflecting the fingers of the collet radially-outward to allow the head portion of the bone anchor to pass through a distal opening defined by the fingers; and
collapsing the plurality of fingers radially-inward once the head portion is disposed within the collet to retain the head portion within the collet.

21. The method of claim 20, wherein collapsing the plurality of fingers of the collet applies a drag force to the head portion of the bone anchor to prevent unintended movement between the receiver member and the bone anchor.

22. The method of claim 21, further comprising inserting a spinal fixation element and a set screw into the receiver member to drive the receiver member proximally with respect to the collet, wedge the plurality of fingers of the collet between the head portion of the bone anchor and the receiver member, and lock movement of the bone anchor relative to the receiver member.

* * * * *